US 7,465,574 B2

(12) United States Patent
Jin et al.

(10) Patent No.: US 7,465,574 B2
(45) Date of Patent: Dec. 16, 2008

(54) RECOMBINANT RSV VIRUS EXPRESSION SYSTEMS AND VACCINES

(75) Inventors: Hong Jin, Sunnyvale, CA (US);
Roderick Tang, San Carlos, CA (US);
Shengqiang Li, Cupertino, CA (US);
Martin Bryant, Los Altos, CA (US)

(73) Assignee: MedImmune, LLC, Gaithersburg, MD (US)

( * ) Notice: Subject to any disclaimer, the term of this patent is extended or adjusted under 35 U.S.C. 154(b) by 43 days.

(21) Appl. No.: 11/078,900

(22) Filed: Mar. 11, 2005

(65) Prior Publication Data

US 2005/0164175 A1 Jul. 28, 2005

Related U.S. Application Data

(63) Continuation of application No. 09/724,379, filed on Nov. 28, 2000, now abandoned, which is a continuation of application No. 09/161,122, filed on Sep. 25, 1998, now abandoned.

(60) Provisional application No. 60/089,207, filed on Jun. 12, 1998, provisional application No. 60/084,133, filed on May 1, 1998, provisional application No. 60/060,153, filed on Sep. 26, 1997.

(51) Int. Cl.
*C12N 7/00* (2006.01)
*C12N 7/02* (2006.01)
*C12N 7/04* (2006.01)
*C07H 21/00* (2006.01)

(52) U.S. Cl. .................. 435/236; 435/235.1; 435/239; 536/23.7; 536/23.72

(58) Field of Classification Search .................. None
See application file for complete search history.

(56) References Cited

U.S. PATENT DOCUMENTS

| | | | |
|---|---|---|---|
| 5,166,057 A | 11/1992 | Palese et al. | |
| 5,716,821 A | 2/1998 | Wertz et al. | |
| 5,840,520 A * | 11/1998 | Clarke et al. | 435/69.1 |
| 5,843,451 A | 12/1998 | Compans et al. | |
| 5,993,824 A | 11/1999 | Murphy et al. | |
| 6,033,886 A | 3/2000 | Conzelmann | |
| 6,060,308 A | 5/2000 | Parrington | |
| 6,168,943 B1 | 1/2001 | Rose | |
| 6,264,957 B1 | 7/2001 | Collins | |
| 6,830,748 B1 | 12/2004 | Jin et al. | |
| 6,923,971 B2 * | 8/2005 | Krempl et al. | 424/211.1 |
| 2003/0027321 A1 | 2/2003 | Jin et al. | |
| 2004/0234506 A1 | 11/2004 | Jin et al. | |
| 2005/0084947 A1 | 4/2005 | Jin et al. | |
| 2005/0158340 A1 | 7/2005 | Jin et al. | |

FOREIGN PATENT DOCUMENTS

| | | |
|---|---|---|
| EP | 0 440 219 | 8/1991 |
| EP | 94202089.2 | 7/1994 |
| EP | 0 780 475 B1 | 6/1999 |
| WO | WO 91/03552 | 3/1991 |
| WO | WO 93/06218 | 4/1993 |
| WO | WO 95/08634 | 3/1995 |
| WO | WO 96/10632 | 4/1996 |
| WO | WO 96/40945 | 12/1996 |
| WO | WO 97/12032 | 4/1997 |
| WO | WO 98/02179 | 1/1998 |
| WO | WO 98/02530 | 1/1998 |
| WO | WO 98/50405 | 11/1998 |
| WO | WO 98/53078 | 11/1998 |
| WO | WO 99/15631 | 4/1999 |
| WO | WO 99/57284 | 11/1999 |
| WO | WO 99/63064 | 12/1999 |
| WO | WO 00/18929 | 4/2000 |
| WO | WO 00/53786 | 9/2000 |

OTHER PUBLICATIONS

Tang et al., "Requirement of cysteines and length of the human respiratory syncytial virus M2-1 protein for protein function and virus viability," Journal of Virology, vol. 75 No. 23, pp. 11328-11335 (Dec. 2001).*
U.S. Appl. No. 09/724,388, filed Nov. 28, 2000, Jin et al.
U.S. Appl. No. 09/724,416, filed Nov. 28, 2000, Jin et al.
U.S. Appl. No. 11/389,618, filed Mar. 24, 2006, Jin et al.
Atreya, P. L. et al.,1998, "The NS1 protein of human respiratory syncytial virus is a potent inhibitor of minigenome transcription of RNA replication," J. Virol. 72:1452-1461.
Baer et al., 1990, "Rhabdoviruses," Virology, $2^{nd}$ ed., Fields et al., eds., Raven Press Ltd., New York, pp. 883, 887.
Ballart (Eschle) et al., 1991, "Retraction: Infectious measles virus from cloned cDNA," EMBO J. 10(11):3558.
Ballart et al., 1990, "Infectious measles virus from cloned cDNA," EMBO J. 9(2):379-384.
Baron et al., 1997, "Rescue of rinderpest virus from cloned cDNA," J. virol. 71:1265-1271.
Beeler et al., 1988, "Neutralization epitopes of the F glycoprotein of respiratory syncytial virus: effect of mutation upon fusion function" J. Virol. 63:2941-2950.
Belshe et al., 1992, "Evaluation of a live attenuated, cold-adapted parainfluenza virus type 3 vaccine in children," J. Clin. Microbiol. 30(8):2064-2070.
Brown et al., 1967 , "Infective Virus Substructure from Vesicular Stomatitis Virus," J. Virol. 1:368-373.

(Continued)

*Primary Examiner*—Zachariah Lucas

(57) ABSTRACT

The present invention relates to genetically engineered recombinant RS viruses and viral vectors which contain heterologous genes which for the use as vaccines. In accordance with the present invention, the recombinant RS viral vectors and viruses are engineered to contain heterologous genes, including genes of other viruses, pathogens, cellular genes, tumor antigens, or to encode combinations of genes from different strains of RSV.

8 Claims, 12 Drawing Sheets

OTHER PUBLICATIONS

Figure 1:
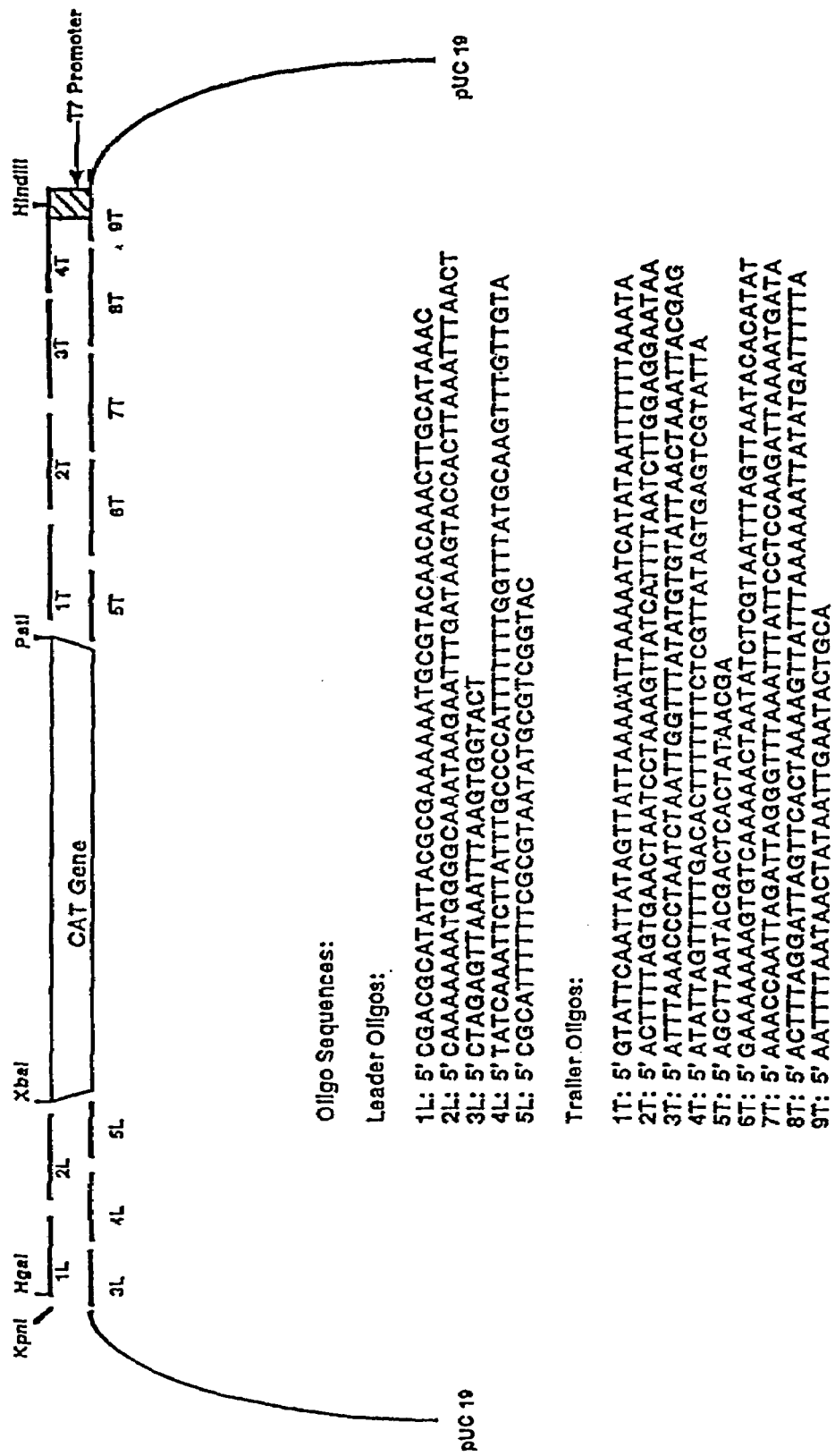

Bucholz et al., 1999, "Generation of bovine respiratory syncytial virus (BRSV) from cDNA: BRSV NS2 is not essential for virus replication in tissue culture, and the human RSV leader region acts as functional BRSV genome promoter," J. Virol. 73(1):251-259.

Bukreyev et al. Recombinant respiratory syncytial virus from which the entire SH gene has been deleted grows efficiently in cell culture and exhibits site-specific attenuation in the respiratory tract of the mouse. J Virol. Dec. 1997;71(12):8973-82.

Bukreyev et al. Recovery of infectious respiratory syncytial virus expressing an additional, foreign gene. J Virol. Oct. 1996;70(10):6634-41.

Calain et al., 1993, "The rule of six, a basic feature for efficient replication of Sendai virus defective interfering RNA," J. Virol. 67(8):4822-4830.

Calain et al., 1992, "Molecular cloning of natural paramyxovirus copy-back defective interfering RNAs and their expression from DNA," Virol. 191:62-71.

Castrucci et al., 1995, "Reverse genetics system for generation of an influenza A virus mutant containing a deletion of the carboxyl-terminal residue of M2 protein," J. Virol. 69(5):2725-2728.

Chin et al., 1969, "Field Evaluation of a Respiratory Syncytial Virus Vaccine and a Trivalent Parainfluenza Virus Vaccine in a Pediatric Population," Am. J. Epidemiol. 89:449-463.

Coates, H.V. et al.,1966, "An antigenic analysis of respiratory syncytial virus isolates by a plaque reduction neutralization test," AM. J. Epid. 83:299-313.

Collins et al., 1984, "Identification of a tenth mRNA of respiratory syncytial virus and assignment of polypeptides to the 10 viral genes," J. Virol. 49:572-578.

Collins et al.,1990, "Evaluation in chimpanzees of vaccinia virus recombinants that express the surface glycoproteins of human respiratory syncytial virus," Vaccine 8:164-168.

Collins, 1991, The paramyxoviruses pp. 103-162. D.W. Kingsbury (ed.) Plenum Press New York.

Collins et al., 1991, "Rescue of synthetic analogs of respiratory syncytial virus genomic RNA and effect of truncations and mutations on the expression of a foreign reporter gene," Proc. Natl. Acad. Sci. USA 88:9663-9667.

Collins et al., 1993, "Rescue of a 7502-nucleotide (49.3% of full-length) synthetic analog of respiratory syncytial virus genomic RNA," Virology 195:252-256.

Collins et al., 1995, "Production of infectious human respiratory syncytial virus from cloned cDNA confirms' an essential role for the transcription elongation factor from the 5' proximal open reading frame of the M2 mRNA in gene expression and provides a capability for vaccine development," Proc. Natl. Acad. Sci. USA 92:11563-11567.

Collins, P.L. et al., "Respiratory Syncytial Virus," pp. 1313-1351 of vol. 1, Fields Virology, et al.,Eds. 3rd ed., Raven Press, 1996.

Collins, P. L. et al., 1996, "Transcription elongation factor of respiratory syncytial virus, a nonsegmented negative-strand RNA virus," Proc. Natl. Acad. Sci. U S A 93, 81-85.

Collins et al. Support plasmids and support proteins required for recovery of recombinant respiratory syncytial virus. Virology. Jul. 5, 1999;259(2):251-5.

Collins et al., 1999, "Rational design of live-attenuated recombinant vaccine virus for human respiratory syncytial virus by reverse genetics," Adv Virus Res. 54:423-51.

Crowe et al., 1994, "Satisfactorily attenuated and protective mutants derived from a partially attenuated cold-passaged respiratory syncytial virus mutant by introduction of additional attenuating mutations during chemical mutagenesis," Vaccine 12:691-699.

Crowe et al. A further attenuated derivative of a cold-passaged temperature-sensitive mutant of human respiratory syncytial virus retains immunogenicity and protective efficacy against wild-type challenge in seronegative chimpanzees. Vaccine. Jul. 1994;12(9):783-790.

Crowe et al.,1995, "Current approaches to the development of vaccines against disease caused by respiratory syncytial virus (RSV) and parainfluenza virus (PIV). A meeting report of the WHO Programme for Vaccine Development," Vaccine 13(4):415-421.

Crowe et al., 1996, "Acquisition of the ts phenotype by a chemically mutagenized cold-passaged human respiratory syncytial virus vaccine candidate results from the acquisition of a single mutation in the polymerase (L) gene," Virus Genes 13(3):269-273.

Current Protocols in Molecular Biology, vol. 1: Chapter 9.6.2, 2005.

Deng et al., 1991, "High-efficiency protein synthesis from T7 RNA polymerase transcripts in 3T3 fibroblasts," Gene 109(2):193-201.

Dimcock and Collins, 1993, "Rescue of synthetic analogs of genomic RNA and replicative-intermediate RNA of human parainfluenza virus type 3," J. Virol. 67(5):2772-2778.

Dudas RA, Karron RA. Respiratory syncytial virus vaccines. Clin Microbiol Rev. Jul. 1998;11(3):430-439.

Durbin et al.,1997, "Recovery of infectious human parainfluenza virus type 3 from cDNA," Virology 235:323-332.

Elango, N. et al.,1989, "mRNA sequence and deduced amino acid sequence of the mumps virus small hydrophobic protein gene," J Virol 63(3):1413-5.

Elroy-Stein et al., 1990, "Cytoplasmic expression system based on constitutive synthesis of bacteriophage T7 RNA polymerase in mammalian cells," Proc. Natl. Acad. Sci. USA 87(17):6743-6747.

Enami et al., 1990, "Introduction of site-specific mutations into the genome of influenza virus," Proc. Natl. Acad. Sci. USA 87:3802-3805.

Fields et al., 1996, Virology 106, 168.

Firestone et al. Nucleotide sequence analysis of the respiratory syncytial virus subgroup A cold-passaged (cp) temperature sensitive (ts) cpts-248/404 live attenuated virus vaccine candidate. Virology. Nov. 15, 1996;225(2):419-22.

Frillingos et al. Cys-scanning mutagenesis: a novel approach to structure function relationships in polytopic membrane proteins. FASEB J. Oct. 1998;12(13):1281-99. Review.

Fuerst et al., 1986, "Eukaryotic transient-expression system based on recombinant vaccinia virus that synthesizes bacteriophage T7 RNA polymerase," Proc. Natl. Acad. Sci. USA 83(21):8122-8126.

Gallione et al., 1985, "A single amino acid substitution in a hydrophobic domain causes temperature-sensitive cell-surface transport of a mutant viral glycoprotein," J. Virol. 54(2):374-382.

Garcia et al., 1993, "Cytoplasmic inclusions of respiratory syncytial virus-infected cells: formation of inclusion bodies in transfected cells that coexpress the nucleoprotein, the phosphoprotein, and the 22K protein," Virology 195:243-247.

Garcin et al., 1995, "A highly recombinogenic system for the recovery of infectious Sendai paramyxovirus from cDNA: generation of a novel copy-back nondefective interfering virus," EMBO J. 14(24):6087-6094.

Gharpure et al., 1969, "Temperature-sensitive mutants of respiratory syncytial virus," J. Virol. 3: 414-421.

Gorman, et al., 1982, "Recombinant genomes which express chloramphenicol acetyltransferase in mammalian cells," Mol. Cell. Biol. 2:1044-1051.

Grosfeld, H. et al., 1995, "RNA replication by respiratory syncytial virus (RSV) is directed by the N, P, and L proteins; transcription also occurs under these conditions but requires RSV superinfection for efficient synthesis of full-length mRNA," J. Virol. 69:5677-5686.

Hardy, R. W. et al., 1998, "The product of the respiratory syncytial virus M2 gene ORF1 enhances readthrough of intergenic junctions during viral transcription," J. Virol. 72, 520-526.

Hardy et al. The Cys(3)-His(1) motif of the respiratory syncytial virus M2-1 protein is essential for protein function. J Virol. Jul. 2000;74(13):5880-5.

He et al., 1997, "Recovery of infectious SV5 from cloned DNA and expression of a foreign gene," Virology 237:249-260.

Hiebert, S. W. et al., 1985, "Identification and predicted sequence of a previously unrecognized small hydrophobic protein, SH, of the paramyxovirus simian virus 5.," J Virol 55(3):744-51.

Hodes et al., 1974, "Genetic alteration in a temperature-sensitive mutant of respiratory syncytial virus after replication in vivo," Proc. Soc. Exp. Biol. Med. 145:1158-1164.

Hoffman et al., 1997, "An infectious clone of human parainfluenza virus type 3," J. Virol. 71:4272-4277.

Howorka et al. Improved protocol for high-throughput cysteine scanning mutagenesis. Biotechniques. Nov. 1998;25(5):764-6, 768, 770 passim.

International Search Report PCT/US98/20230, 1999.

Jin, H. et al., 1997, "Influenza virus hemagglutinin and neuraminidase cytoplasmic tails control particle shape," EMBO J. 16(6):1236-47.

Jin et al. Recombinant human respiratory syncytial virus (RSV) from cDNA and construction of subgroup A and B chimeric RSV. Virology. Nov. 10, 1998;251(1):206-14.

Jin et al., 2000, "Recombinant respiratory syncytial viruses with deletions in the NSI, NS2, SH, and M2-2 genes are attenuated in vitro and in vivo," Virology 273(1):210-8.

Kapikian et al., 1969, "An epidemiologic study of altered clinical reactivity to respiratory syncytial (RS) virus infection in children previously vaccinated with an inactivated RS virus vaccine," Am. J. Epidemiol. 89:405-421.

Karron, R. A. et al.,1997, "Evaluation of two live, cold-passaged, temperature-sensitive respiratory syncytial virus vaccines in chimpanzees and in human adults, infants, and children," J. Infect. Dis. 176:1428-1436.

Kato et al., 1996, "Initiation of Sendai virus multiplication from transfected cDNA or RNA with negative or positive sense," Genes to Cells 1:569-579.

Kim et al., 1973, "Safety and antigenicity of temperature sensitive (TS) mutant respiratory syncytial virus (RSV) in infants and children," Pediatrics 52:56-63.

Kingsbury et al., 1987, "Assembly of influenza ribonucleoprotein in vitro using recombinant nucleoprotein," Virology 156:396-403.

Kingsbury, ed., 1991, "Deletion mutants of paramyxoviruses," in: The Paramyxoviruses, Plenum Press, New York, pp. 275-298.

Kolakofsky et al., 1998, Paramyxovirus RNA synthesis and the requirement for hexamer genome length: The Rule of Six revisited, J. Virol., 72(2):891-899.

Krystal et al., 1986, "Expression of the three influenza virus polymerase proteins in a single cell allows growth complementation of viral mutants," Proc. Natl. Acad. Sci. USA 83: 2709-2713.

Kucera et al., 1985, "Pathways of the early propagation of virulent and avirulent rabies stains from the eye to the brain," J. Virol. 55(1):158-162.

Kunkel, 1985, "Rapid and efficient site-specific mutagenesis without phenotypic selection," Proc. Natl. Acad. Sci. U.S.A. 82:488-492.

Lafay et al., 1994, "Vaccination against rabies: construction and characterization of SAG2, a double avirulent derivative of SADBern," Vaccine 12(4):317-320.

Lawson et al.,1995, "Recombinant vesicular stomatitis viruses from DNA," Proc. Natl. Acad. Sci USA 92:4477-4481.

Li et al., 1988, "Site-specific mutations in vectors that express antigenic and temperature-sensitive phenotypes of the M gene of vesicular stomatitis virus," J. Virol. 62(10):3729-3737.

Lieber et al., 1989, "High level gene expression in mammalian cells by a nuclear T7-phase RNA polymerase," Nucleic Acids Res. 17(21):8485-8493.

Ligas et al., 1988, "A herpes simplex virus mutant in which glycoprotein D sequences are replaced by b-galactosidase sequences binds to but is unable to penetrate into cells," J. Virol. 62(5):1486-1494.

Lodish et al. Molecular Cell Biology, Third Ed. Scientific American Books, 1995.

Luytjes et al., 1989, "Amplification, expression, and packaging of foreign gene by influenza virus," Cell 59:1107-1113.

McIntosh et al., 1990 "Respiratory Syncytial Virus" 2nd ed. Virology (D. M. Knipe et al., Ed.) Raven Press, Ltd., N.Y. 1045-1072.

Mink et al., "Nucleotide sequences of the 3' leader and 5' trailer regions of human respiratory syncytial virus genomic RNA" 1991, Virology 185:615-624.

Morita et al., 1987, "Phenotypic revertants of temperature-sensitive M protein mutants of vesicular stomatitis virus: sequence analysis and functional characterization," J. Virol. 61(2):256-263.

Murphy et al. An update on approaches to the development of respiratory syncytial virus (RSV) and parainfluenza virus type 3 (PIV3) vaccines. Virus Res. Apr. 1994;32(1):13-36, Review.

Nayak et al., 1983, Genetics of Influenza Viruses, P. Palese and D. W. Kingsbury, eds., Springer-Verlag, Vienna, pp. 255-279.

Olmsted et al., 1986, "Expression of the F glycoprotein of respiratory syncytial virus by a recombinant vaccinia virus: comparison of the individual contributions of the F and G glycoproteins to host immunity," Proc. Natl. Acad. Sci. 83:7462-7466.

Owens et al., 1993, "Cytoplasmic domain requirement for incorporation of a foreign envelope protein into vesicular stomatitis virus," J. Virol. 67(1):360-365.

Park et al., 1991, "Rescue of a foreign gene by Sendai virus," Proc. Natl. Acad. Sci. USA 88:5537-5541.

Pattnaik, 1992, "Infectious defective interfering particles of VSV from transcripts of a cDNA clone," Cell 69:1011-1020.

Prince et al. Efficacy and safety studies of a recombinant chimeric respiratory syncytial virus FG glycoprotein vaccine in cotton rats. J Virol. Nov. 2000;74(22):10287-10292.

Radecke et al., 1995, "Rescue of measles viruses from cloned DNA," EMBO J. 14:5773-5784.

Radecke et al., 1997, "Reverse Genetics Meets the Nonsegmented Negative-Strand RNA Viruses," Rev. Med. Virol. 7(1):49-63.

Rauh et al., 1991, "Pseudorablies virus gllycoproteins gII and gp50 are essential for virus penetration," J. Virol. 65(10):5348-5356.

Schnell et al., 1994, "Infectious rabies virus from cloned cDNA," Ninth Int'l Conference on Negative Strand Viruses (Oct. 2-7, 1994) pp. 87, Abstract 90.

Schnell et al., 1994, "Infectious rabies viruses from cloned cDNA," EMBO J. 13:4195-4203.

Schnitzer et al., 1979, "Morphological and biochemical characterization of viral particles produced by the tsO45 mutant of vesicular stomatitis virus at restrictive temperature," J. Virol. 29(1):185-195.

Seif et al., 1985, "Rabies virulence: effect on pathogenicity and sequence characterization of rabies virus mutations affecting antigenic site III of the glycoprotein," J. Virol. 53(3):926-934.

Shioda et al., 1986, "Determination of the complete nucleotide sequence of the Sendai virus genome RNA and the predicted amino acid sequences of the F, HN and L proteins," Nucleic Acids Res. 14(4):1545-1563.

Takeda et al., 2000, "Recovery of pathogenic measles virus from cloned cDNA," J. Virol. 74(14):6643-6647.

Tang et al. Effects of human metapneumovirus and respiratory syncytial virus antigen insertion in two 3' proximal genome positions of bovine/human parainfluenza virus type 3 on virus replication and immunogenicity. J Virol. Oct. 2003;77(20):10819-10828.

Teng et al. Identification of the respiratory syncytial virus proteins required for formation and passage of helper-dependent infectious particles. J Virol. Jul. 1998;72(7):5707-16.

Teng et al. Altered growth characteristics of recombinant respiratory syncytial viruses which do not produce NS2 protein. J Virol. Jan. 1999;73(1):466-73.

Tolley et al. Identification of mutations contributing to the reduced virulence of a modified strain of respiratory syncytial virus. Vaccine. Dec. 1996;14(17-18):1637-46.

Tordo et al., 1992, "Evolution of negative stranded RNA genomes," Seminars in Virol. 3:341-357.

Wang et al.,1989, Proc. Natl. Acad. Sci. "Quantitation of mRNA by the polymerase chain reaction," 86:9717-9721.

Whetter et al., 1994, "Analysis of hepatitis A virus translation in a T7 polymerase-expressing cell line," Arch. Virol. Suppl. 9:291-298.

Whitehead et al. Replacement of the F and G proteins of respiratory syncytial virus (RSV) subgroup A with those of subgroup B generates chimeric live attenuated RSV subgroup B vaccine candidates. J Virol. Dec. 1999;73(12):9773-80.

Whitehead et al., 1999, "Recombinant respiratory syncytial virus bearing a deletion of either the NS2 or SH gene is attenuated in chimpanzees," J Virol. 73(4):3438-42.

Whitt et al., 1990, "A fusion-defective mutant of the vesicular stomatitis virus glycoprotein," J. Virol. 64(190):4907-4913.

Whitt et al., 1989, "Glycoprotein cytoplasmic domain sequences required for rescue of a vesicular stomatitis virus glycoprotein mutant," J. Virol. 63(9):3569-3578.

Worthington et al.,1996, "Metal binding properties and secondary structure of the zinc-binding domain of Nup475," Proc. Natl. Acad. Sci. 93:13754-13759.

Wright et al., 1976, "Evaluation of a live, attenuated respiratory syncytial virus vaccine in infants," J. Pediatrics 88:931-936.

Wyatt et al., 1995, "Replication-deficient vaccinia virus encoding bacteriophage T7 RNA polymerase for transient gene expression in mammalian cells," Virology 210(1):202-205.

Yu et al., 1995, Functional cDNA clones of the human respiratory syncytial (RS) virus N, P, and L proteins support replication of RS virus genomic RNA analogs and define minimal trans-acting requirements for RNA replication, J. Virol. 69:2412-2419.

Bowie et al., 1990, "Deciphering the message in protein sequences: tolerance to amino acid substitutions," Science 247(4948):1306-10.

Sambrook et al., Molecular Cloning—A Laboratory Manual, Cold Spring Harbor laboratory Press, Cold Spring Harbor, NY, 1989.

definition "phenotype," Science and Biotechnology, biotech.icmb.utexas.edu/search/dict-search.html, 2004.

definition "phenotype," The On-line Medical Dictionary, cancerweb.ncl.ac.uk/omd/ , 2003.

Conzelmann et al., 1994, "Rescue of synthetic genomic RNA analogs of rabies virus by plasmid-encoded proteins," J. Virol. 68(2):713-719.

Crowe Jr., James E., 2001, "Respiratory syncytial virus vaccine development," Vaccine 20(Suppl 1):S32-37.

Kahn, 2000, "Respiratory syncytial virus vaccine development," Curr. Opin. Pediatr. 12(3):257-262.

Karron et al., 1997, "Respiratory syncytial virus (RSV) SH and G proteins are not essential for viral replication in vitro: clinical evaluation and molecular characterization of a cold-passaged, attenuated RSV subgroup B mutant," Proc. Natl. Acad. Sci. USA 94(25):13961-13966.

* cited by examiner

```
MDPIINGNSANVYLT  DSYILKGVISFSECNA  LGSYIFNGPYLKNDY  TNLISRQNPLIEHMN  LKKLNITQSLISKYH     75
KGEIKLEEPTYFQSL  LMTYKSMTSSEQIAT   TNLLKKIRRAIEIS   DVKVYAILNKLGLKE  KDKIKSNNGQDEDNS    150
VITTIKDDILSAVK   DNQSHLKADKNHSTK   QKDTKTLLKKLMC    SMQHPPSWLIHWFNL  YTKLNNILTQYRSNE    225
VKNHGFTLIDNQTLS  GFQFILNQYGCIVVH   KELKRITVTTNQFL   TWKDISLSRLNVCLI  TWISNCLNTLNKSLG    300
LRCGFNNVILTQLFL  YGDCILKLPHNEGFY   IIKEVEGFIMSLIIN  ITEEDQFRKRFYNSM  LNNITDAANKAQKNL    375
LSRVCHTLLDKTVSD  NIINGRWIIILSKFL   KLIKLAGDNNLNNLS  ELYFLFRIFGHPMVR  ERQAMDAVKINCNET    450
KFYLLSSLSMLRGAF  IYRIIKGFVNNYNRW   PTLRNAIVLPLRWLT  YYKLNTYPSLLELTE  RDLIVLSGLRFYREF    525
RLPKKVDLEMIINDK  AISPPKNLIWTSFPR   NYMPSHIQNVIEHEK  LKFSESDKSRRVLEY  YLRDNKFNECDLYNC    600
VVNQSYLNNPNHVVS  LTGKERELSVGRMFA   MQPGMFRQVQILAEK  MIAENILQFFPESLT  RYGDLELQKILELKA    675
GISNKSNRYADNIANN YISKCSIITDLSKFN   QAFRYETSCICSDVL  DELHGVQSLFSWLHL  TIPHVTIICTYRHAP    750
PYIGDHIVDLNNVDE  QSGLYRYHMGGIEGW   CQKLWTIEAISLLDL  ISLKGKFSITALING  DNQSIDISKPIRLME    825
GQTHAQADYLLALNS  LKLLYKEYAGIGHKL   KGTETYISRDMQFMS  KTIQHNGVYYPASIK  KVLRVGPWINTILDD    900
FKVSLESIGSLTQEL  EYRGESLLCSLIFRN   VWLYNQIALQLKNHA  LCNNKLYLDILKVLK  HLKTFFNLDNIDTAL    975
TLYMNLPMLFGGDP   NLLYRSFYRRTPDFL   TEAIVHSVFILSYYT  NHDLKDKLQDLSDDR  LNKFLTCIITFDKNP    1050
NAEFVTLMRDPQALG  SERQAKITSEINRLA   VTEVLSTAPNKIFSK  SAQHYTTTEIDLNDI  MQNIEPTYPHGLRVV    1125
YESLPFYKAEKIVNL  ISGTKSITNNILEKTS  AIDLTDIDRATEMNR  KNITLLIRIIPLDCN  FDKREILSMENLSIT    1200
ELSKYVRERSWSLSN  IVGVTSPSIMVTMDI   KYTTSTISSGIIIEK  YNVNSLTRGERGPTK  PWVGSSTQEKTMPV     1275
YNRQVLTKKQRDQID  LLAKLDWVYASIDNK   DEFMEELSIGTLGLT  YEKAKKLFPQYLSVN  YLHRLTVSSRPCEFP    1350
ASIPAYRTTNYHFDT  SPINRLITEKYGDED   IDIVFQNCISFGLSL  MSVVEQFTNVCPNRI  ILIPKLNETHLMKPP    1425
IFTGDVDIHKLKQVI  QKQHMFLPDKCISLTQ  YVELFLSNKTLKSGS  HVNSNLILAHKISDY  FANTYILSTNLAGHW    1500

| | | | | |
|---|---|---|---|---|
| MDPIINGNSANVYLT | DSYLKGVISFSECNA | LGSYIFNGPYLKNDY | TNLISRQNPLIEHMN | LKKLNITQSLISKYH | 75 |
| KGEIKLEEPTYFQSL | LMIYKSMTSSEQIAT | TNLLKKLIRRAIEIS | DVKVYAIINKLGLKE | KDKIKSNNGQDEDNS | 150 |
| VITTIKDDLLSAVK | DNQSHLKADKNHSTK | QKDTIKTLLKKLMC | SMQHPPSWLIHWFNL | YTKLNNILFQYRSNE | 225 |
| VKNHGFTLIDNQTLS | GFQFIINQYGCIVYH | KELKRITVTTNQFL | TWKDISLSRLNVCLI | TWISNCLNTLNKSLG | 300 |
| LRCGFNNVLLTQLFL | YGDCILKLFHNEGFY | IIKEVEGFIMSLIIN | ITEEDQFKRFYNSM | LNNITDAANKAQKNL | 375 |
| LSRVCHTLLDKTVSD | NIINGRWILLSKFL | KLIKLAGDNNLNNLS | ELYFLFRIFGHPMVD | ERQAMDAVKINCNET | 450 |
| KFYLLSSLSMLRGAF | IYRIIKGFVNNYNRW | PTLRNALVLPLRWLT | YYKLNTYPSLLELTE | RDLIVLSGLRFYREF | 525 |
| RLPKKVDLEMIINDK | AISPPKNLIWTSFPR | NYMPSHIQNYIEHEK | LKFSESDKSRRVLEY | YLRDNKFNECDLYNC | 600 |
| VVNQSYLNNPNHVS | LTGKERELSVGRMFA | MQPGMFRQVQILAEK | MIAENILQFFPESLT | RYGDLELQKILELKA | 675 |
| GISNKSNRYNDNYNN | YISKCSIITDLSKFN | QAFRYETSCICSDVL | DELHGVQSLFSWLHL | TIPHVTIICTYRHAP | 750 |
| PYIGDHIVDLNNVDE | QSGLYRYHMGGIEGW | CQKLWTIEAISLLDL | ISLKGKFSITALING | DNQSIDISKPIRLME | 825 |
| GQTHAQADYLLALNS | LKLLYKEYAGIGHKL | KGTETYISRDMQFMS | KTIQHNGVYYPASIK | KVLRVGPWINTILDD | 900 |
| FKVSLESIGSLTQEL | EYRGESLLCSLIFRN | VWLYNQIALQLKNHA | LCNNKLYLDILKVLK | HLKTFFNLDNIDTAL | 975 |
| TLYMNLPMLFGGGDP | NLLYRSFYRRTPDFL | TEAIVHSVFILSYYT | NHDLKDKLQDLSDDR | LNKFLTCIITFDKNP | 1050 |
| NAEFVTLMRDPQALG | SERQAKITSEINRLA | VTFVLSTAPNKIFSK | SAQHYTTEIDLNDI | MQNIEPTYPHGLRVV | 1125 |
| YESLPFYKAEKIVNL | ISGTKSIINILEKTS | AIDLTDIDRATEMMR | KNITLLIRILPLDQN | RDKREILSMENLSIT | 1200 |
| ELSKYVRERSWSLSN | IVGVTSPSIMYTMDI | KYTTSTISSGIIIEK | YNVNSLTRGERGPTK | PWVGSSTQEKKTMPV | 1275 |
| YNRQVLIKKQRDQID | LLAKLDWVYASIDNK | DEFMEELSIGTLGLT | YEKAKKLFPQYLSVN | YLHRLTVSSRPCEFP | 1350 |
| ASIPAYRTTNYHFDT | SPINRILTEKYGDED | IDIVFQNCISFGLSL | MSVVEQFTNVCPNRI | ILIPKLNEIHLMKPP | 1425 |
| IFTGDVDIHKLKQVI | QKQHMFLPDKISLTQ | YVELFLSNKTLKSGS | HVNSNLLIAHKISDY | FNNTYILSTNLAGHW | 1500 |
| ILLIQLMKDSKGIFE | KDWGEGYITDHMFIN | LKVFFNAYKTYLLCF | HKGYGKAKLECDMNT | SDLLCVLELIDSSYW | 1575 |
| KSMSKVFLEQKVIKY | ILSQDASLHRVKGGH | SFKLWFLKRLNVAEP | TVCPWVNIDYHPTH | MKAILTYIDLVRMGL | 1650 |
| INIDRIHKNIKHKFN | DEFYTSNLFYINYNF | SDNTHLLTKHIRIAN | SELENNYANKLYHPTP | ETLENILANPIKSND | 1725 |
| KKTLNDYCIGKNVDS | IMLPLLSNKKLIKSS | AMIRTNYSKQDLYNL | FPMVVIDRIIDHSGN | TAKSNQLYTTTSHQI | 1800 |
| SLVHNSTSLYCMLPW | HHINRFNFVFSSTGC | KISIEYILKDLKIKD | PNCIAFIGEGAGNLL | LRTVVELHPDIRYIY | 1875 |
| RSLKDCNDHSLPIEF | LRLYNGHINIDYGEN | LTIPATDAITNNIHWS | YLHIKPAEPISLFVC | DAELSVTVNWSKIII | 1950 |
| EWSKHVRKCKYCSSV | NKCMLIVKYHAQDDI | DFKLDNITILKTYVC | LGSKLKGSEVYLVLT | IGPANIFPVFNVVQN | 2025 |
| AKLILSRTKNFIMPK | KADKESIDANIKSLI | PFLCYPITKKGINTA | LSKLKSVVSGDILSY | SIAGRNEVFSNKLIN | 2100 |
| HKHMNILKWENHVLN | FRSTELNYNHLYMVE | STYPYLSELLNSLTT | NELKKLKIKITGSLLY | NFHNE | 2165 |

C   Cysteine residues
C   Cysteine residues that were changed to valine or aspartic acid
C   Cysteine residue deleted

FIG. 11

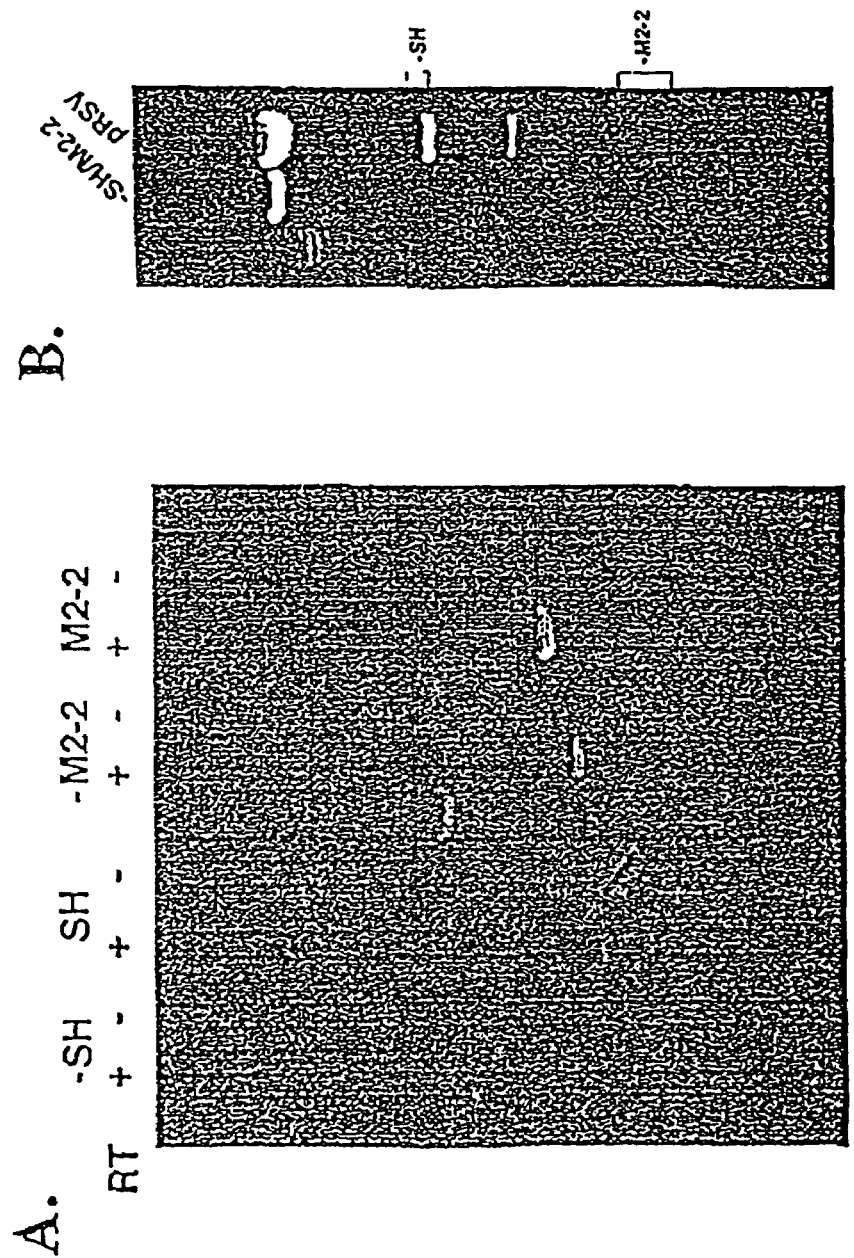
FIGS. 12A-B

RECOMBINANT RSV VIRUS EXPRESSION SYSTEMS AND VACCINES

This application is a continuation application of U.S. application Ser. No. 09/724,379 filed Nov. 28, 2000, abandoned, which is a continuation application of U.S. application Ser. No. 09/161,122 filed Sep. 25, 1998, abandoned. U.S. application Ser. No. 09/161,122 filed Sep. 25, 1998 claims benefit of priority from U.S. Provisional Application Ser. Nos. 60/060,153 filed Sep. 26, 1997; 60/084,133 filed May 1, 1998; and 60/089,207 filed Jun. 12, 1998.

1. INTRODUCTION

The present invention relates to recombinant negative strand virus RNA templates which may be used to express heterologous gene products in appropriate host cell systems and/or to construct recombinant viruses that express, package, and/or present the heterologous gene product. The expression products and chimeric viruses may advantageously be used in vaccine formulations. In particular, the present invention relates to methods of generating recombinant respiratory syncytial viruses and the use of these recombinant viruses as expression vectors and vaccines. The invention is described by way of examples in which recombinant respiratory syncytial viral genomes are used to generate infectious viral particles.

2. BACKGROUND OF THE INVENTION

A number of DNA viruses have been genetically engineered to direct the expression of heterologous proteins in host cell systems (e.g., vaccinia virus, baculovirus, etc.). Recently, similar advances have been made with positive-strand RNA viruses (e.g., poliovirus). The expression products of these constructs, i.e., the heterologous gene product or the chimeric virus which expresses the heterologous gene product, are thought to be potentially useful in vaccine formulations (either subunit or whole virus vaccines). One drawback to the use of viruses such as vaccinia for constructing recombinant or chimeric viruses for use in vaccines is the lack of variation in its major epitopes. This lack of variability in the viral strains places strict limitations on the repeated use of chimeric vaccinia, in that multiple vaccinations will generate host-resistance to the strain so that the inoculated virus cannot infect the host. Inoculation of a resistant individual with chimeric vaccinia will, therefore, not induce immune stimulation.

By contrast, negative-strand RNA viruses such as influenza virus and respiratory syncytial virus, demonstrate a wide variability of their major epitopes. Indeed, thousands of variants of influenza have been identified; each strain evolving by antigenic drift. The negative-strand viruses such as influenza and respiratory syncytial virus would be attractive candidates for constructing chimeric viruses for use in vaccines because its genetic variability allows for the construction of a vast repertoire of vaccine formulations which will stimulate immunity without risk of developing a tolerance.

2.1. Respiratory Syncytial Virus

Virus families containing enveloped single-stranded RNA of the negative-sense genome are classified into groups having non-segmented genomes (Paramyxoviridae, Rhabdoviridae) or those having segmented genomes (Orthomyxoviridae, Bunyaviridae and Arenaviridae). Paramyxoviridae have been classified into three genera: paramyxovirus (sendai virus, parainfluenza viruses types 1-4, mumps, newcastle disease virus); morbillivirus (measles virus, canine distemper virus and rinderpest virus); and pneumovirus (respiratory syncytial virus and bovine respiratory syncytial virus).

Human respiratory syncytial virus (RSV) is the leading cause of severe lower respiratory tract disease in infants and young children and is responsible for considerable morbidity and mortality. Two antigenically diverse RSV subgroups A and B are present in human populations. RSV is also recognized as an important agent of disease in immuno-compromised adults and in the elderly. Due to the incomplete resistance to RSV reinfection induced by natural infection, RSV may infect multiple times during childhood and life. The goal of RSV immunoprophylaxis is to induce sufficient resistance to prevent the serious disease which may be associated with RSV infection. The current strategies for developing RSV vaccines principally revolve around the administration of purified viral antigen or the development of live attenuated RSV for intranasal administration. However, to date there have been no approved vaccines or highly effective antiviral therapy for RSV.

Infection with RSV can range from an unnoticeable infection to severe pneumonia and death. RSV possesses a single-stranded nonsegmented negative-sense RNA genome of 15,221 nucleotides (Collins, 1991, In The paramyxoviruses pp. 103-162, D. W. Kingsbury (ed.) Plenum Press, New York). The genome of RSV encodes 10 mRNAs (Collins et al., 1984, J. Virol. 49: 572-578). The genome contains a 44 nucleotide leader sequence at the 3' termini followed by the NS1-NS2-N-P-M-SH-G-F-M2-L and a 155 nucleotide trailer sequence at the 5' termini (Collins. 1991, supra). Each gene transcription unit contains a short stretch of conserved gene start (GS) sequence and a gene end (GE) sequences.

The viral genomic RNA is not infectious as naked RNA. The RNA genome of RSV is tightly encapsidated with the major nucleocapsid (N) protein and is associated with the phosphoprotein (P) and the large (L) polymerase subunit. These proteins form the nucleoprotein core, which is recognized as the minimum unit of infectivity (Brown et al., 1967, J. Virol. 1: 368-373). The RSV N, P, and L proteins form the viral RNA dependent RNA transcriptase for transcription and replication of the RSV genome (Yu et al., 1995, J. Virol. 69:2412-2419; Grosfeld et al., 1995, J. Virol. 69:5677-86). Recent studies indicate that the M2 gene products (M2-1 and M2-2) are involved and are required for transcription (Collins et al., 1996, Proc. Natl. Acad. Sci. 93:81-5).

The M protein is expressed as a peripheral membrane protein, whereas the F and G proteins are expressed as integral membrane proteins and are involved in virus attachment and viral entry into cells. The G and F proteins are the major antigens that elicit neutralizing antibodies in vivo (as reviewed in McIntosh and Chanock, 1990 "Respiratory Syncytial Virus" 2nd ed. Virology (D. M. Knipe et al., Ed.) Raven Press, Ltd., N.Y.). Antigenic dimorphism between the subgroups of RSV A and B is mainly linked to the G glycoprotein, whereas the F glycoprotein is more closely related between the subgroups.

Despite decades of research, no safe and effective RSV vaccine has been developed for the prevention of severe morbidity and mortality associated with RSV infection. A formalin-inactivated virus vaccine has failed to provide protection against RSV infection and its exacerbated symptoms during subsequent infection by the wild-type virus in infants (Kapikian et al., 1969, Am. J. Epidemiol. 89:405-21; Chin et al., 1969, Am. J. Epidemiol. 89:449-63) Efforts since have focused on developing live attenuated temperature-sensitive mutants by chemical mutagenesis or cold passage of the wild-type RSV (Gharpure et al., 1969, J. Virol. 3: 414-21; Crowe et al., 1994, Vaccine 12: 691-9). However, earlier trials yielded discouraging results with these live attenuated temperature sensitive mutants. Virus candidates were either underattenuated or overattenuated (Kim et al., 1973, Pediatrics 52:56-63; Wright et al., 1976, J. Pediatrics 88:931-6) and some of the vaccine candidates were genetically unstable which resulted in the loss of the attenuated phenotype (Hodes et al., 1974, Proc. Soc. Exp. Biol. Med. 145:1158-64).

Attempts have also been made to engineer recombinant vaccinia vectors which express RSV F or G envelope glycoproteins. However, the use of these vectors as vaccines to protect against RSV infection in animal studies has shown inconsistent results (Olmsted et al. 1986, Proc. Natl. Acad. Sci. 83:7462-7466; Collins et al., 1990, Vaccine 8:164-168).

Thus, efforts have turned to engineering recombinant RSV to generate vaccines. For a long time, negative-sense RNA viruses were refractory to study. Only recently has it been possible to recover negative strand RNA viruses using a recombinant reverse genetics approach (U.S. Pat. No. 5,166,057 to Palese et al.). Although this method was originally applied to engineer influenza viral genomes (Luytjes et al. 1989, Cell 59:1107-1113; Enami et al. 1990, Proc. Natl. Acad. Sci. USA 92: 11563-11567), it has been successfully applied to a wide variety of segmented and nonsegmented negative strand RNA viruses, including rabies (Schnell et al. 1994, EMBO J. 13: 4195-4203); VSV (Lawson et al., 1995, Proc. Natl. Acad. Sci USA 92: 4477-81); measles virus (Radecke et al., 1995, EMBO J. 14:5773-84); rinderpest virus (Baron & Barrett, 1997, J. virol. 71: 1265-71); human parainfluenza virus (Hoffman & Banerjee, 1997, J. Virol. 71:3272-7; Dubin et al., 1997, Virology 235:323-32); SV5 (He et al., 1997, Virology 237:249-60); respiratory syncytial virus (Collins et al. 1991, Proc. Natl. Acad. Sci. USA 88: 9663-9667) and Sendai virus (Park et al. 1991, Proc. Natl. Acad. Sci. USA 88:5537-5541; Kato et al. 1996, Genes to Cells 1:569-579). Although this approach has been used to successfully rescue RSV, a number of groups have reported that RSV is still refractory to study given several properties of RSV which distinguish it from the better characterized paramyxoviruses of the genera *Paramyxovirus, Rubulavirus*, and *Morbillivirus*. These differences include a greater number of RNAs, an unusual gene order at the 3' end of the genome, extensive strain-to-strain sequence diversity, several proteins not found in other nonsegmented negative strand RNA viruses and a requirement for the M2 protein (ORF1) to proceed with full processing of full length transcripts and rescue of a full length genome (Collins et al. PCT WO97/12032; Collins, P. L. et al. pp 1313-1357 of volume 1, *Fields Virology*, et al., Eds. (3rd ed., Raven Press, 1996).

3. SUMMARY OF THE INVENTION

The present invention relates to genetically engineered recombinant RS viruses and viral vectors which contain heterologous genes which for the use as vaccines. In accordance with the present invention, the recombinant RS viral vectors and viruses are engineered to contain heterologous genes, including genes of other viruses, pathogens, cellular genes, tumor antigens, or to encode combinations of genes from different strains of RSV.

Recombinant negative-strand viral RNA templates are described which may be used to transfect transformed cell that express the RNA dependent RNA polymerase and allow for complementation. Alternatively, a plasmid expressing the components of the RNA polymerase from an appropriate promoter can be used to transfect cells to allow for complementation of the negative-strand viral RNA templates. Complementation may also be achieved with the use of a helper virus or wild-type virus to provide the RNA dependent RNA polymerase. The RNA templates are prepared by transcription of appropriate DNA sequences with a DNA-directed RNA polymerase. The resulting RNA templates are of negative-or positive-polarity and contain appropriate terminal sequences which enable the viral RNA-synthesizing apparatus to recognize the template. Bicistronic mRNAs can be constructed to permit internal initiation of translation of viral sequences and allow for the expression of foreign protein coding sequences from the regular terminal initiation site, or vice versa.

As demonstrated by the examples described herein, recombinant RSV genome in the positive-sense or negative-sense orientation is co-transfected with expression vectors encoding the viral nucleocapsid (N) protein, the associated nucleocapsid phosphoprotein (P), the large (L) polymerase subunit protein, with or without the M2/ORF1 protein of RSV to generate infectious viral particles. Vaccinia vectors expressing RSV virus polypeptides are used as the source of proteins which were able to replicate and transcribe synthetically derived RNPs. The minimum subset of RSV proteins needed for specific replication and expression of the viral RNP was found to be the three polymerase complex proteins (N, P and L). This suggests that the M2 gene function is not absolutely required for the replication, expression and rescue of infectious RSV.

The expression products and/or chimeric virions obtained may advantageously be utilized in vaccine formulations. In particular, recombinant RSV genetically engineered to demonstrate an attenuated phenotype may be utilized as a live RSV vaccine. In another embodiment of the invention, recombinant RSV may be engineered to express the antigenic polypeptides of another strain of RSV (e.g., RSV G and F proteins) or another virus (e.g., an immunogenic peptide from gp120 of HIV) to generate a chimeric RSV to serve as a vaccine, that is able to elicit both vertebrate humoral and cell-mediated immune responses. The use of recombinant influenza or recombinant RSV for this purpose is especially attractive since these viruses demonstrate tremendous strain variability allowing for the construction of a vast repertoire of vaccine formulations. The ability to select from thousands of virus variants for constructing chimeric viruses obviates the problem of host resistance encountered when using other viruses such as vaccinia.

3.1.1 Definitions

As used herein, the following terms will have the meanings indicated:

cRNA=anti-genomic RNA
HA=hemagglutinin (envelope glycoprotein)
HIV=human immunodefiency virus
L=large polymerase subunit
M=matrix protein (lines inside of envelope)
MDCK=Madin Darby canine kidney cells
MDBK=Madin Darby bovine kidney cells
moi=multiplicity of infection
N=nucleocapsid protein
NA=neuraminidase (envelope glycoprotein)
NP=nucleoprotein (associated with RNA and required for polymerase activity)
NS=nonstructural protein (function unknown)
nt=nucleotide
P=nucleocapsid phosphoprotein PA, PB1, PB2=RNA-directed RNA polymerase components RNP=ribonucleoprotein (RNA, PB2, PB1, PA and NP)
rRNP=recombinant RNP
RSV=respiratory syncytial virus
vRNA=genomic virus RNA
viral polymerase complex PA, PB1, PB2 and NP
WSN=influenza A/WSN/33 virus
WSN-HK virus: reassortment virus containing seven genes from WSN virus and the NA gene from influenza A/HK/8/68 virus

4. DESCRIPTION OF THE FIGURES

FIG. 1. Schematic representation of the RSV/CAT construct (pRSVA2CAT) used in rescue experiments. The approximate 100 nt long leader and 200 nt long trailer regions of RSV were constructed by the controlled annealing of synthetic oligonucleotides containing partial overlapping complementarity. The overlapping leader oligonucleotides are indicated by the 1L-5L shown in the construct. The overlapping trailer nucleotides are indicated by the 1T-9T shown in the construct. The nucleotide sequences of the leader and trailer DNAs were ligated into purified CAT gene DNA at the indicate XbaI and PstI sites respectively. This entire construct was then ligated into KpnI/HindIII digested pUC19. The inclusion of a T7 promoter sequence and a HgaI site flanking the trailer and leader sequences, respectively, allowed in vitro synthesis of RSV/CAT RNA transcripts containing the precise genomic sequence 3' and 5' ends (SEQ ID NOS 1-14).

Figure 2:
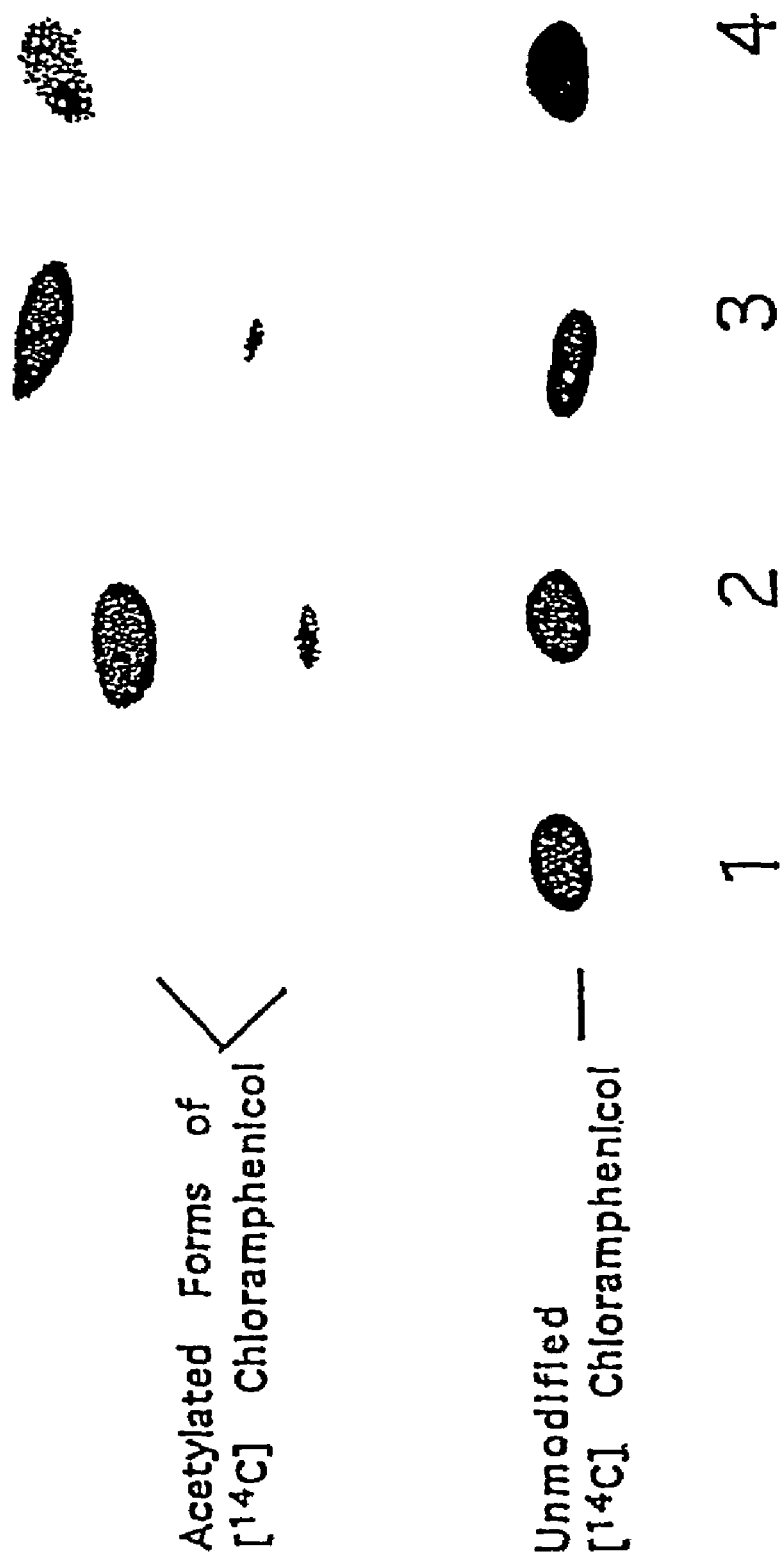

FIG. 2. Thin layer chromatogram (TLC) showing the CAT activity present in 293 cell extracts following infection and transfection with RNA transcribed from the RSV/CAT construct shown in FIG. 11. Confluent monolayers of 293 cells in six-well plates (~$10^6$ cells) were infected with either RSV A2 or B9320 at an m.o.i. of 0.1-1.0 pfu cell. At 1 hour post infection cells were transfected with 5-10 µg of CAT/RSV using the Transfect-Act™ protocol of Life Technologies. At 24 hours post infection the infected/transfected monolayers were harvested and processed for subsequence CAT assay according to Current Protocols in Molecular Biology, Vol. 1, Chapter 9.6.2; Gorman, et al., (1982) Mol. Cell. Biol. 2:1044-1051. Lanes 1, 2, 3 and 4 show the CAT activity present in (1) uninfected 293 cells, transfected with CAT/RSV-A2 infected 293 cells, co-infected with supernatant from (2) above. The CAT activity observed in each lane was produced from ⅕ of the total cellular extract from $10^6$ cells.

Figure 3:
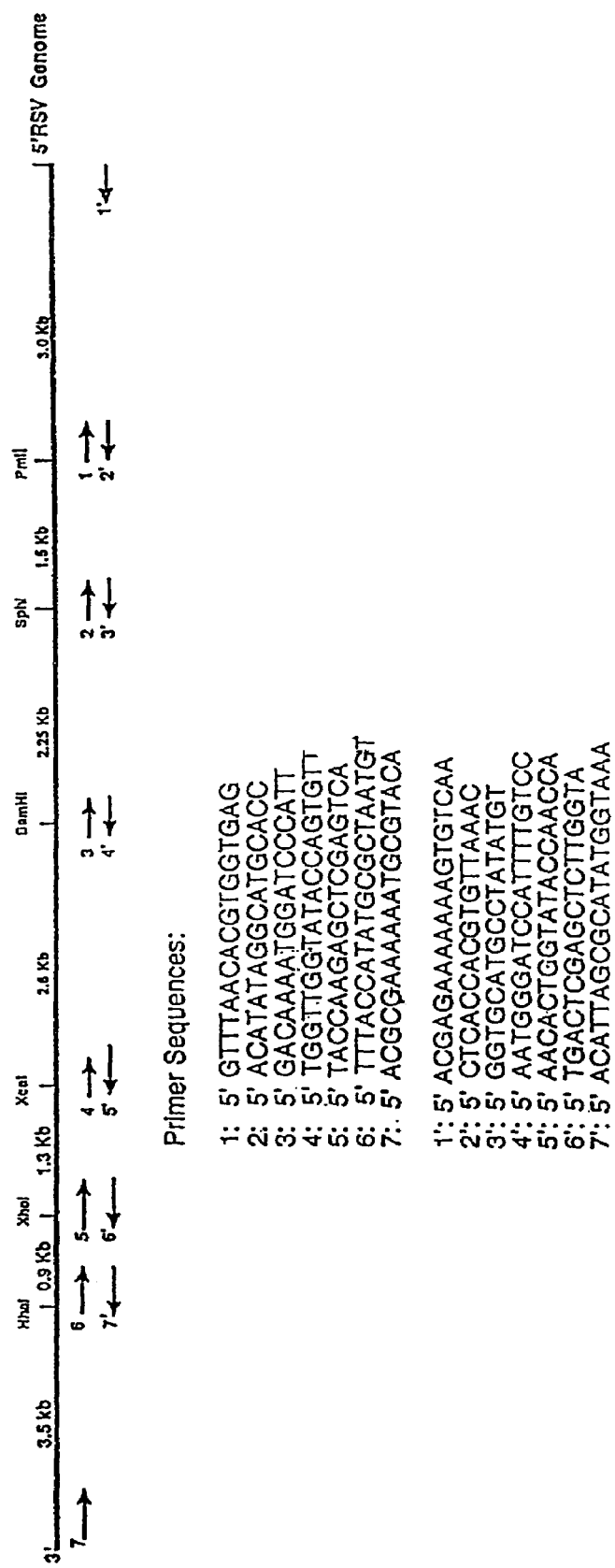

FIG. 3. Schematic representation of the RSV strain A2 genome showing the relative positions of the primer pairs used for the synthesis of cDNAs comprising the entire genome. The endonuclease sites used to splice these clones together are indicated; these sites were present in the native RSV sequence and were included in the primers used for cDNA synthesis. Approximately 100 ng of viral genomic RNA was used in RT/PCR reactions for the separate synthesis of each of the seven cDNAs. The primers for the first and second strand cDNA synthesis from the genomic RNA template are also shown. For each cDNA, the primers for the first strand synthesis are nos. 1-7 and the primers for the second strand synthesis are nos. 1'-7' (SEQ ID NOS 15-19, 21-28, 48).

Figure 4:
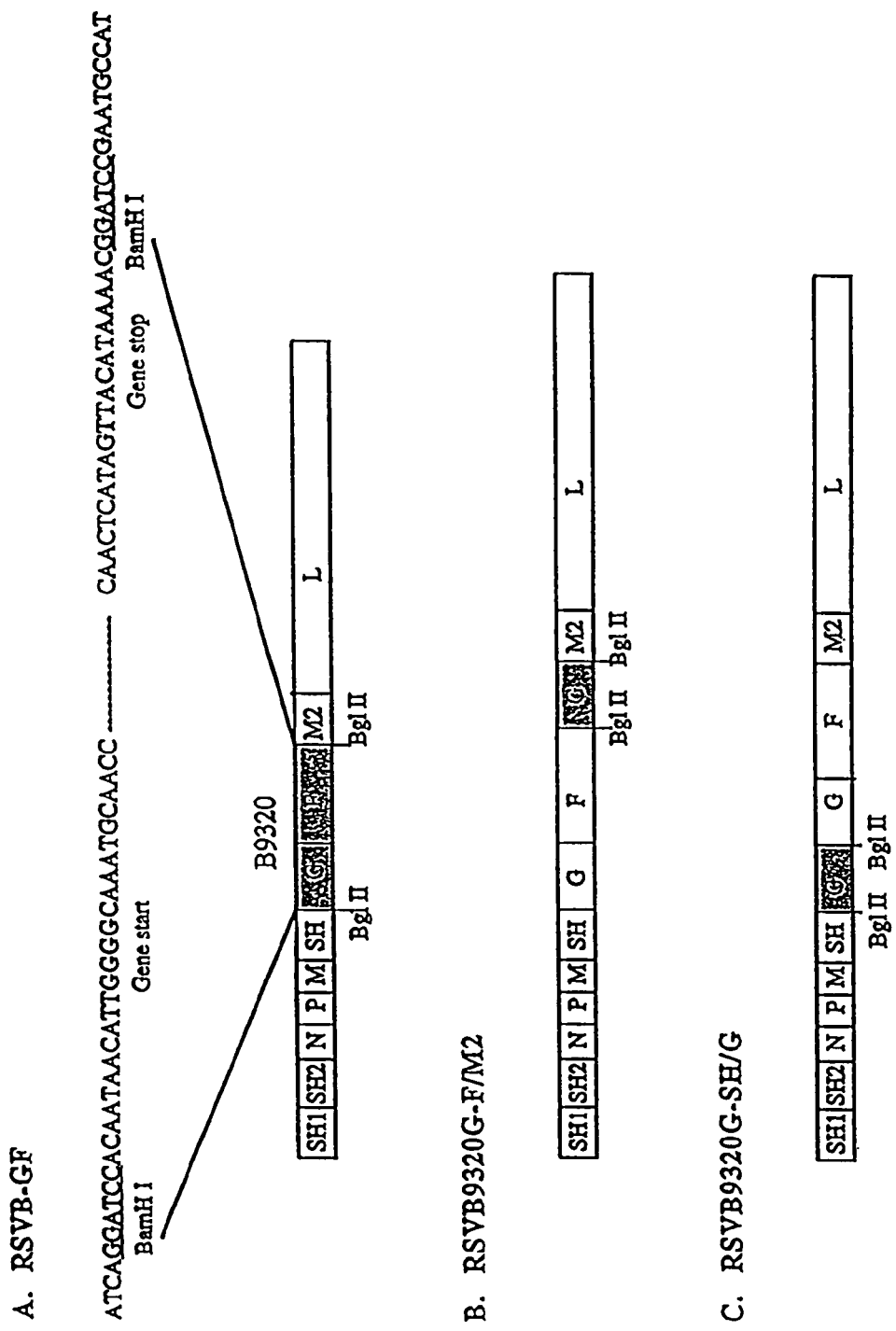

FIG. 4. Schematic representation of the RSV subgroup B strain B9320. BamHl sites were created in the oligonucleotide primers used for RT/PCR in order to clone the G and F genes from the B9320 strain into RSV subgroup A2 antigenomic cDNA (FIG. 4A). A cDNA fragment which contained G and F genes from 4326 nucleotides to 9387 nucleotides of A2 strain was first subcloned into pUC19 (pUCRVH). Bgl II sites were created at positions of 4630 (SH/G intergenic junction) (FIG. 4B) and 7554 (F/M2 intergenic junction (FIG. 4C). B93260 A-G and -F cDNA inserted into pUCR/H which is deleted of the A-G and F genes. The resulting antigenomic cDNA clone was termed as pRSVB-GF and was used to transfect Hep-2 cells to generate infectious RSVB-GF virus (SEQ ID NOS 49-50).

Figure 5:
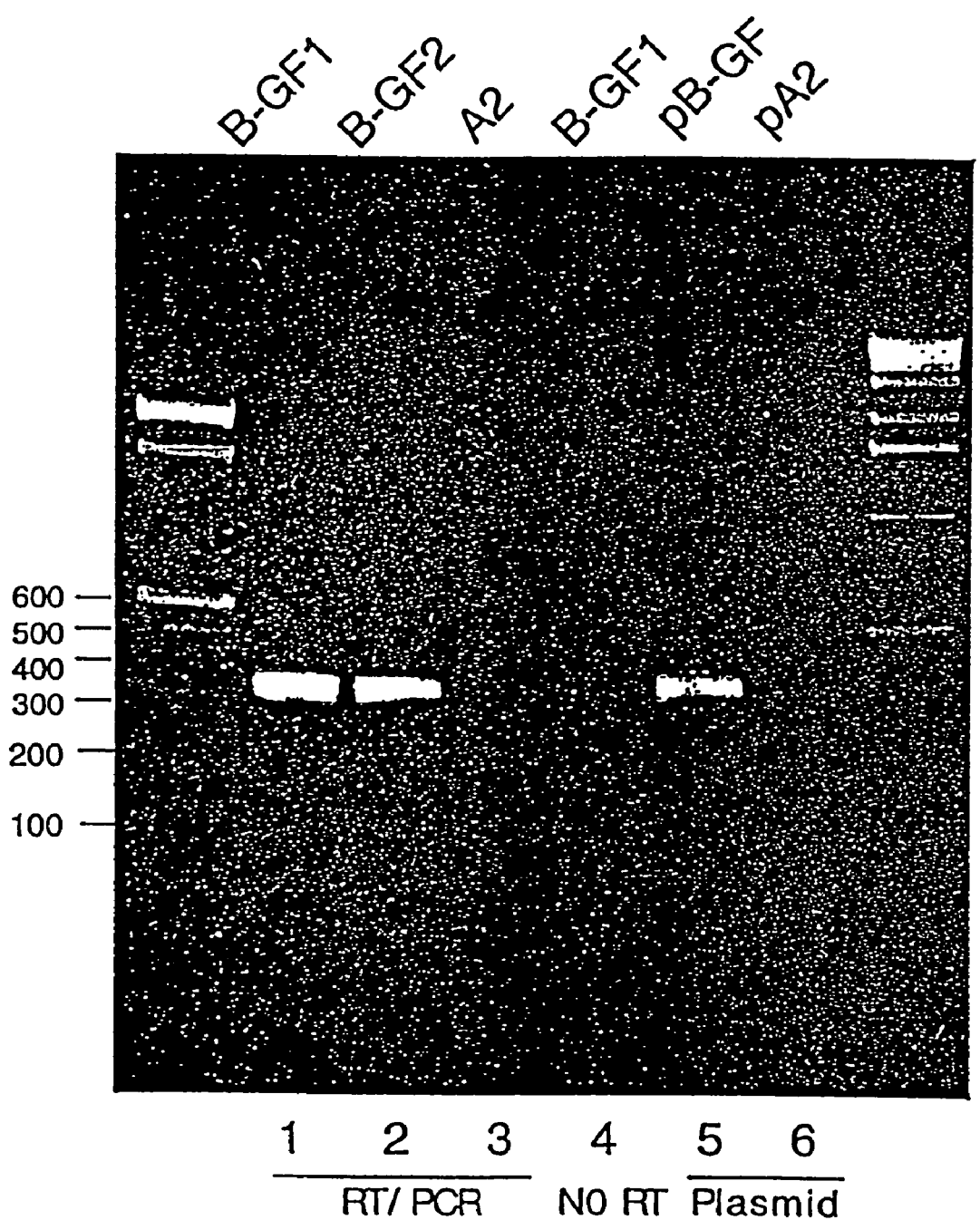

FIG. 5. Recombinant RSVB-GF virus was characterized by RT/PCR using RSV subgroup B specific primers. RSV subgroup B specific primers in the G region were incubated with aliquots of the recombinant RSV viral genomes and subjected to PCR. The PCR products were analyzed by electrophoresis on a 1% agarose gel and visualized by staining with ethidium bromide. As shown, no DNA product was produced in the RT/PCR reaction using RSV A2 as a template. However, a predicted product of 254 base pairs was seen in RT/PCR of RSVB-GF RNA and PCR control of plasmid pRSV-GF DNA as template, indicating the rescued virus contained G and F genes derived from B9320 virus.

Figure 6:
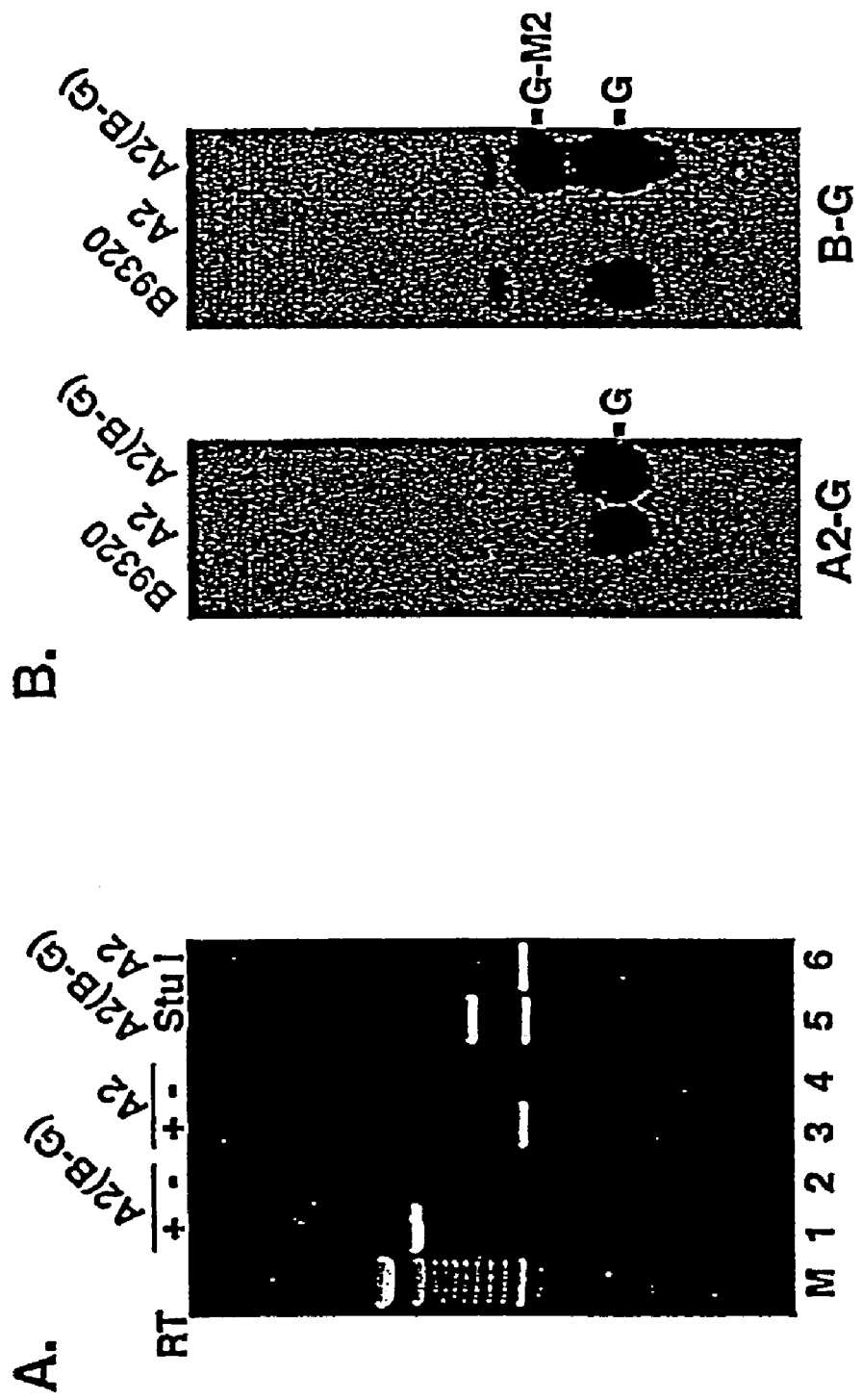

FIG. 6. Identification of chimeric (rRSVA2(B-G) by RT/PCR and Northern blot analysis of RNA expression. FIG. 6A. RT/PCT analysis of chimeric rRSV A2(B-G), A2(B-G), in comparison with wild-type A2(A2). Virion RNA extracted from rRSVA2(B-G) (lanes 1, 2) and rRSVA2 (lanes 3, 4) was reverse transcribed using a primer annealed to (−) sense vRNA in the RSV F gene in the presence (+) or absence (−) of reverse transcriptase (RT), followed by PCR with a primer fair flanking the B-G insertion site. No DNA was detected in RT/PCR when reverse transcriptase (RT) was absent (lanes 2, 4). A cDNA fragment, which is about 1 kb bigger than the cDNA derived from A2, was produced from rRSVA(B-G). This longer PCR DNA product was digested by Stu I restriction enzyme unique to the inserted B-G gene (lane 5). 100 bp DNA size marker is indicated (M). FIG. 6B. Northern blot analysis of G mRNA expression. Hep-2 cells were infected with RSV B9320, rRSV and chimeric rRSV A2 (B-G). At 48 hr postinfection, total cellular RNA was extracted and electrophoresed on a 1.2% agarose gel containing formadehyde. RNA was transferred to Hybond Nylon membrane and the filter was hybridized with a $^{32}$P-labeled oligonucleotide probe specific for A2-G or specific for B9320-G mRNA. Both A2 G specific and B9320 G specific transcripts were detected in the rRSV A2 (B-G) infected cells. The run-off RNA transcript (G-M2) from rRSV A2 (B-G) infected cells is also indicated.

Figure 7:
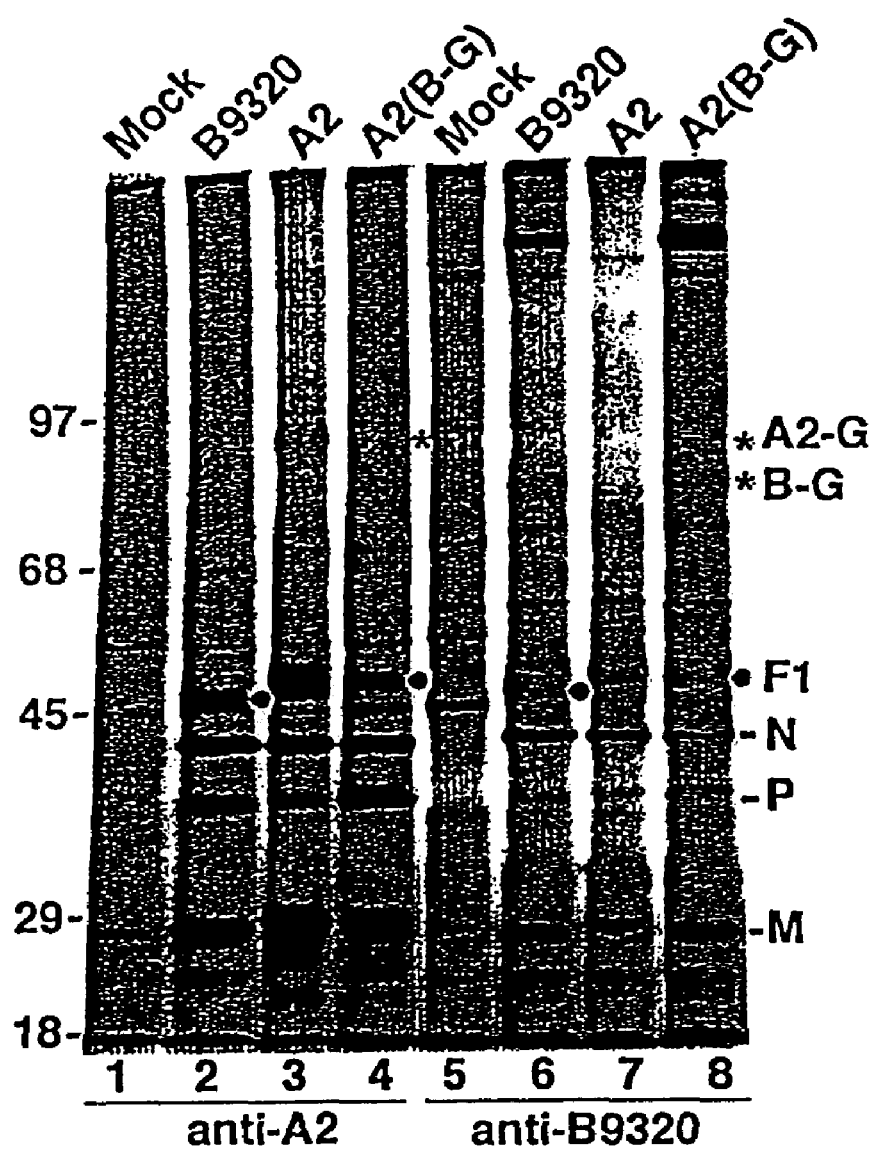

FIG. 7. Analysis of protein expression by rRSV A2 (B-G). Hep-2 cells were mock-infected (lanes 1, 5), infected with RSV B9320 (lanes 2, 6), rRSV (lanes 3, 7) and rRSV A2 (B-G) (lanes 4, 8). At 14-18 hr postinfection, infected cells were labeled with $^{35}$S-promix and polypeptides were immunoprecipitated by goat polyclonal antiserum against RSV A2 strain (lanes 1-5) or by mouse polyclonal antiserum against RSV B9320 strain (lanes 5-8). Immunoprecipitated polypeptides were separated on a 10% polyacrylamide gel. Both RSV A2 specific G protein and RSV B9320 specific G protein were produced in rRSV A2 (B-G) infected cells. The G protein migration is indicated by *. Mobility of the F1 glycoprotein, and N, P, and M is indicated. Molecular sizes are shown on the left in kilodaltons.

Figure 8:
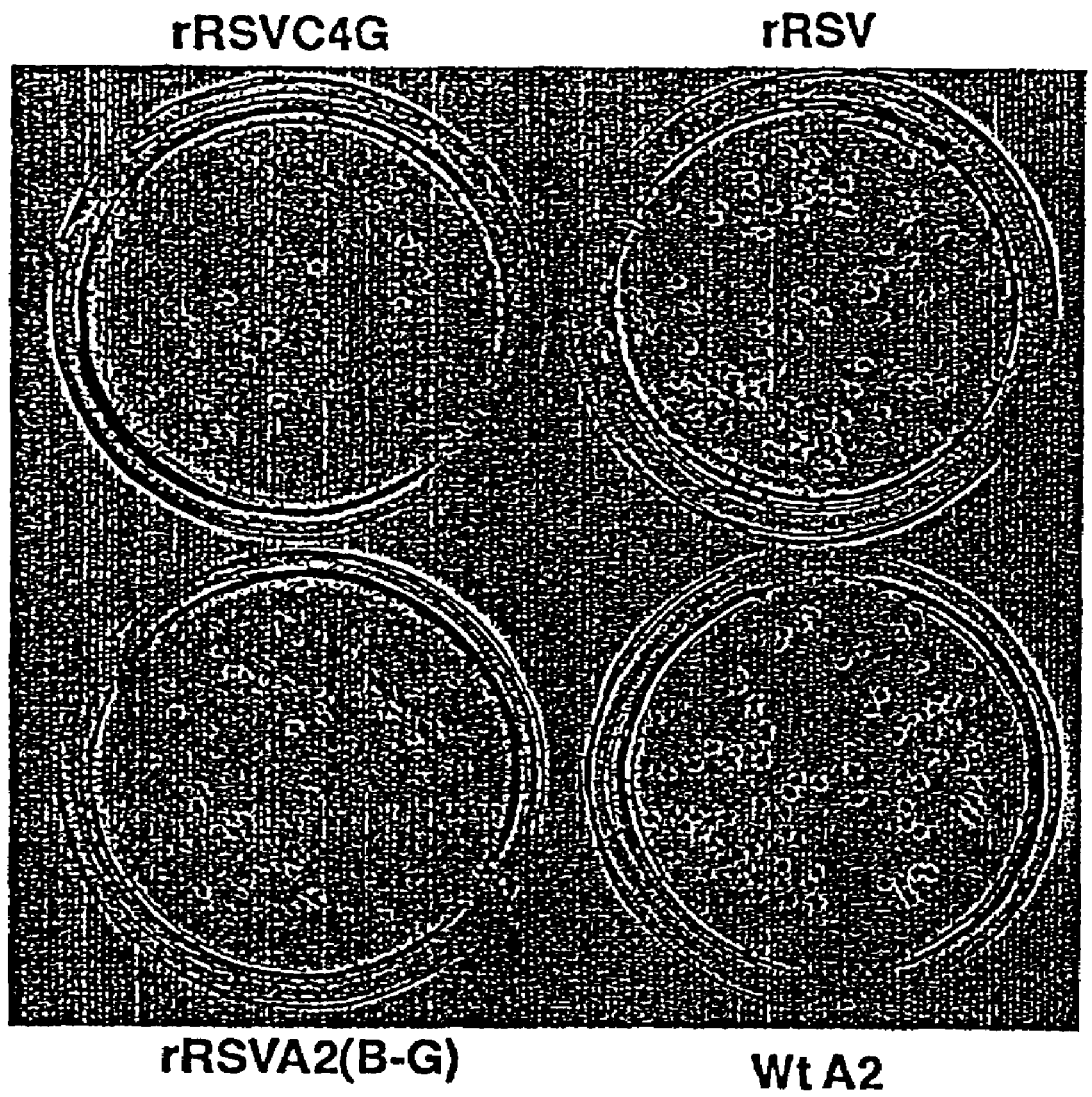

FIG. 8. Plaque morphology of rRSV, rRSVC3G, rRSV A2 (B-G) and wild-type A2 virus (wt A2). Hep-2 cells were infected with each virus and incubated at 35° C. for six days. The cell monolayers were fixed, visualized by immunostaining, and photographed.

FIG. 9. Growth curve of rRSV, rRSVC4G, wild-type A2 RSV (wt A2) and chimeric rRSV A2 (B-G). Hep-2 cells were infected with either virus at a moi of 0.5 and the medium was harvested at 24 hr intervals. The titer of each virus was determined in duplicate by plaque assay on Hep-2 cells and visualized by immunostaining.

FIG. 10. RSV L protein charged residue clusters targeted for site-directed mutagenesis. Contiguous charged amino acid residues in contiguous clusters were converted to alanines by site-directed mutagenesis of the RSV L gene using the QuikChange site-directed mutagenesis kit (Stratagene) (SEQ ID NO 29).

FIG. 11. RSV L protein cysteine residues targeted for site-directed mutagenesis. Cysteine residues were converted to alanine-residues by site-directed mutagenesis of the RSV L gene using the QuikChange site-directed mutagenesis kit (Stratagene)(SEQ ID NO 30).

FIG. 12. Identification RSV M2-2 and SH deletion mutants. Deletions in M2-2 were generated by Hind III digestion of pET(S/B) followed by recloning of a remaining Sac I to BamHI fragment into a full-length clone. Deletions in SH were generated by Sac I digestion of pET(A/S) followed by recloning of a remaining Avr II Sac I fragment into a full-length clone. FIG. 12A. Identification of the recovered rRSVsSH and rRSV M2-2 was performed by RT/PCR using primer pairs specific for the SH gene or M2-2 gene, respectively. FIG. 12B rRSV SH M2-2 was also detected by RT/PCR using primer pairs specific for the M2-2 and SH genes. RT/PCR products were run on an ethidium bromide agarose gel and bands were visualized by ultraviolet (UV) light.

5. DESCRIPTION OF THE INVENTION

The present invention relates to genetically engineered recombinant RS viruses and viral vectors which express heterologous genes or mutated RS viral genes or a combination of viral genes derived from different strains of RS virus. The invention relates to the construction and use of recombinant negative strand RS viral RNA templates which may be used with viral RNA-directed RNA polymerase to express heterologous gene products in appropriate host cells and/or to rescue the heterologous gene in virus particles. The RNA templates of the present invention may be prepared by transcription of appropriate DNA sequences using a DNA-directed RNA polymerase such as bacteriophage T7, T3 or Sp6 polymerase. The recombinant RNA templates may be used to transfect continuous/transfected cell lines that express the RNA-directed RNA polymerase proteins allowing for complementation.

The invention is demonstrated by way of working examples in which infectious RSV is rescued from cDNA containing the RSV genome in the genomic or antigenomic sense introduced into cells expressing the N, P, and L proteins of the RSV polymerase complex. The working examples further demonstrate that expression of M2-1 is not required for recovery of infectious RSV from cDNA which is contrary to what has been reported earlier (Collins et al., 1995, Proc. Natl. Acad. Sci. USA 92:11563-7). Furthermore, the addition of plasmids expressing M2-1 has little effect on the RSV rescue efficiency. M2-deleted-RSV is an excellent vehicle to generate chimeric RSV encoding heterologous gene products in place of the M2 genes, these chimeric viral vectors and rescued virus particles have utility as expression vectors for the expression of heterologous gene products and as live attenuated RSV vaccines expressing either RSV antigenic polypeptides or antigenic polypeptides of other viruses.

The invention is further demonstrated by way of working examples in which a cDNA clone which contained the complete genome of RSV, in addition to a T7 promoter, a hepatitis delta virus ribozyme and a T7 terminator is used to generate an infectious viral particle when co-transfected with expression vectors encoding the N, P, L and M2/orf1 proteins of RSV. In addition, the working examples describe RNA transcripts of cloned DNA containing the coding region—in negative sense orientation—of the chloramphenicol-acetyltransferase (CAT) gene or the green fluorescent protein (GFP) gene flanked by the 5' terminal and 3' terminal nucleotides of the RSV genome. The working examples further demonstrate that an RSV promoter mutated to have increased activity resulted in rescue of infectious RSV particles from a full length RSV cDNA with high efficiency. These results demonstrate the successful use of recombinant viral negative strand templates and RSV polymerase with increased activity to rescue RSV. This system is an excellent tool to engineer RSV viruses with defined biological properties, e.g. live-attenuated vaccines against RSV, and to use recombinant RSV as an expression vector for the expression of heterologous gene products.

This invention relates to the construction and use of recombinant negative strand viral RNA templates which may be used with viral RNA-directed RNA polymerase to express heterologous gene products in appropriate host cells, to rescue the heterologous gene in virus particles and/or express mutated or chimeric recombinant negative strand viral RNA templates (see U.S. Pat. No. 5,166,057 to Palese et al., incorporated herein by reference in its entirety). In a specific embodiment of the invention, the heterologous gene product is a peptide or protein derived from another strain of the virus or another virus. The RNA templates may be in the positive or negative-sense orientation and are prepared by transcription of appropriate DNA sequences using a DNA-directed RNA polymerase such as bacteriophage T7, T3 or the Sp6 polymerase.

The ability to reconstitute RNP's in vitro allows the design of novel chimeric influenza and RSV viruses which express foreign genes. One way to achieve this goal involves modifying existing viral genes. For example, the HA gene of influenza may be modified to contain foreign sequences in its external domains. Where the heterologous sequence are epitopes or antigens of pathogens, these chimeric viruses may be used to induce a protective immune response against the disease agent from which these determinants are derived.

For example, a chimeric RNA may be constructed in which a coding sequence derived from the gp120 coding region of human immunodeficiency virus was inserted into the F or G coding sequence of influenza, and chimeric virus was produced from transfection of this chimeric RNA segment into a host cell infected with wild-type RSV.

In addition to modifying genes coding for surface proteins, genes coding for nonsurface proteins may be altered. The latter genes have been shown to be associated with most of the important cellular immune responses in the RS virus system. Thus, the inclusion of a foreign determinant in the G or F gene of RSV may—following infection—induce an effective cellular immune response against this determinant. Such an approach may be particularly helpful in situations in which protective immunity heavily depends on the induction of cellular immune responses (e.g., malaria, etc.).

The present invention also relates to attenuated recombinant RSV produced by introducing specific mutations in the genome of RSV which results in an amino acid change in an RSV protein, such as a polymerase protein, which results in an attenuated phenotype.

5.1. Construction of the Recombinant RNA Templates

Heterologous gene coding sequences flanked by the complement of the viral polymerase binding site/promoter, e.g., the complement of the 3'-RSV termini or the 3'- and 5'-RSV termini may be constructed using techniques known in the art. Heterologous gene coding sequences may also be flanked by the complement of the RSV polymerase binding site/promoter, e.g., the leader and trailer sequence of RSV using techniques known in the art. Recombinant DNA molecules containing these hybrid sequences can be cloned and transcribed by a DNA-directed RNA polymerase, such as bacteriophage T7, T3 or the Sp6 polymerase and the like, to produce the recombinant RNA templates which possess the appropriate viral sequences that allow for viral polymerase recognition and activity.

In a preferred embodiment of the present invention, the heterologous sequences are derived from the genome of another strain of RSV, e.g., the genome of RSV A strain is engineered to include the nucleotide sequences encoding the antigenic polypeptides G and F of RSV B strain, or fragments thereof. In such an embodiment of the invention, heterologous coding sequences from another strain of RSV can be used to substitute for nucleotide sequences encoding antigenic polypeptides of the starting strain, or be expressed in addition to the antigenic polypeptides of the parent strain, so that a recombinant RSV genome is engineered to express the antigenic polypeptides of one, two or more strains of RSV.

In yet another embodiment of the invention, the heterologous sequences are derived from the genome of any strain of influenza virus. In accordance with the present invention, the heterologous coding sequences of influenza may be inserted within a RSV coding sequence such that a chimeric gene product is expressed which contains the heterologous peptide sequence within the RSV viral protein. In either embodiment, the heterologous sequences derived from the genome of influenza may include, but are not limited to HA, NA, PB1, PB2, PA, NS1 or NS2.

In one specific embodiment of the invention, the heterologous sequences are derived from the genome of human immunodeficiency virus (HIV), preferably human immunodeficiency virus-1 or human immunodeficiency virus-2. In another embodiment of the invention, the heterologous coding sequences may be inserted within an influenza gene coding sequence such that a chimeric gene product is expressed which contains the heterologous peptide sequence within the influenza viral protein. In such an embodiment of the invention, the heterologous sequences may also be derived from the genome of a human immunodeficiency virus, preferably of human immunodeficiency virus-1 or human immunodeficiency virus-2.

In instances whereby the heterologous sequences are HIV-derived, such sequences may include, but are not limited to sequences derived from the env gene (i.e., sequences encoding all or part of gp160, gp120, and/or gp41), the pol gene (i.e., sequences encoding all or part of reverse transcriptase, endonuclease, protease, and/or integrase), the gag gene (i.e., sequences encoding all or part of p7, p6, p55, p17/18, p24/25) tat, rev, nef, vif, vpu, vpr, and/or vpx.

One approach for constructing these hybrid molecules is to insert the heterologous coding sequence into a DNA complement of a RSV genomic RNA so that the heterologous sequence is flanked by the viral sequences required for viral polymerase activity; i.e., the viral polymerase binding site/promoter, hereinafter referred to as the viral polymerase binding site. In an alternative approach, oligonucleotides encoding the viral polymerase binding site, e.g., the complement of the 3'-terminus or both termini of the virus genomic segments can be ligated to the heterologous coding sequence to construct the hybrid molecule. The placement of a foreign gene or segment of a foreign gene within a target sequence was formerly dictated by the presence of appropriate restriction enzyme sites within the target sequence. However, recent advances in molecular biology have lessened this problem greatly. Restriction enzyme sites can readily be placed anywhere within a target sequence through the use of site-directed mutagenesis (e.g., see, for example, the techniques described by Kunkel, 1985, Proc. Natl. Acad. Sci. U.S.A. 82;488). Variations in polymerase chain reaction (PCR) technology, described infra, also allow for the specific insertion of sequences (i.e., restriction enzyme sites) and allow for the facile construction of hybrid molecules. Alternatively, PCR reactions could be used to prepare recombinant templates without the need of cloning. For example, PCR reactions could be used to prepare double-stranded DNA molecules containing a DNA-directed RNA polymerase promoter (eq., bacteriophage T3, T7 or Sp6) and the hybrid sequence containing the heterologous gene and the influenza viral polymerase binding site. RNA templates could then be transcribed directly from this recombinant DNA. In yet another embodiment, the recombinant RNA templates may be prepared by ligating RNAs specifying the negative polarity of the heterologous gene and the viral polymerase binding site using an RNA ligase. Sequence requirements for viral polymerase activity and constructs which may be used in accordance with the invention are described in the subsections below.

5.1.1. Insertion of the Heterologous Genes

The genes coding for the M2 or L proteins contain a single open reading frame. The gene coding for NS contains two open reading frames for NS1 and NS2. The G and F proteins, coded for by separate genes, are the major surface glycoproteins of the virus. Consequently, these proteins are the major targets for the humoral immune response after infection. Insertion of a foreign gene sequence into any of these coding regions could be accomplished by either a complete replacement of the viral coding region with the foreign gene or by a partial replacement. Complete replacement would probably best be accomplished through the use of PCR-directed mutagenesis.

Alternatively, a bicistronic mRNA could be constructed to permit internal initiation of translation of viral sequences and allow for the expression of foreign protein coding sequences from the regular terminal initiation site. Alternatively, a bicistronic mRNA sequence may be constructed wherein the viral sequence is translated from the regular terminal open reading frame, while the foreign sequence is initiated from an internal site. Certain internal ribosome entry site (IRES) sequences may be utilized. The IRES sequences which are chosen should be short enough to not interfere with RS virus packaging limitations. Thus, it is preferable that the IRES chosen for such a bicistronic approach be no more than 500 nucleotides in length, with less than 250 nucleotides being preferred. Further, it is preferable that the IRES utilized not share sequence or structural homology with picornaviral elements. Preferred IRES elements include, but are not limited to the mammalian BiP IRES and the hepatitis C virus IRES.

5.2. Expression of Heterologous Gene Products Using Recombinant RNA Template The recombinant templates prepared as described above can be used in a variety of ways to express the heterologous gene products in appropriate host cells or to create chimeric viruses that express the heterologous gene products. In one embodiment, the recombinant template can be combined with viral polymerase complex purified infra, to produce rRNPs which are infectious. To this end, the recombinant template can be transcribed in the presence of the viral polymerase complex. Alternatively, the recombinant template may be mixed with or transcribed in the presence of viral polymerase complex prepared using recombinant DNA methods (e.g. see Kingsbury et al., 1987, Virology 156:396-403). In yet another embodiment, the recombinant template can be used to transfect appropriate host cells to direct the expression of the heterologous gene product at high levels. Host cell systems which provide for high levels of expression include continuous cell lines that supply viral functions such as cell lines superinfected with RSV, cell lines engineered to complement RSV viral functions, etc.

5.3. Preparation of Chimeric Negative Strand RNA Virus

In order to prepare chimeric virus, reconstituted RNPs containing modified RSV RNAs or RNA coding for foreign proteins may be used to transfect cells which are also infected with a "parent" RSV virus. Alternatively, the reconstituted RNP preparations may be mixed with the RNPs of wild type parent virus and used for transfection directly. Following reassortment, the novel viruses may be isolated and their genomes be identified through hybridization analysis. In additional approaches described herein for the production of infectious chimeric virus, rRNPs may be replicated in host cell systems that express the RSV or influenza viral polymerase proteins (e.g., in virus/host cell expression systems; transformed cell lines engineered to express the polymerase proteins, etc.), so that infectious chimeric virus are rescued; in this instance, helper virus need not be utilized since this function is provided by the viral polymerase proteins expressed. In a particularly desirable approach, cells infected with rRNPs engineered for all eight influenza virus segments may result in the production of infectious chimeric virus which contain the desired genotype; thus eliminating the need for a selection system.

Theoretically, one can replace any one of the genes of RSV, or part of any one of the RSV genes, with the foreign sequence. However, a necessary part of this equation is the ability to propagate the defective virus (defective because a normal viral gene product is missing or altered). A number of possible approaches exist to circumvent this problem.

A third approach to propagating the recombinant virus may involve co-cultivation with wild-type virus. This could be done by simply taking recombinant virus and co-infecting cells with this and another wild-type virus (preferably a vaccine strain). The wild-type virus should complement for the defective virus gene product and allow growth of both the wild-type and recombinant virus. This would be an analogous situation to the propagation of defective-interfering particles of influenza virus (Nayak et al., 1983, In: Genetics of Influenza Viruses, P. Palese and D. W. Kingsbury, eds., Springer-Verlag, Vienna, pp. 255-279). In the case of defective-interfering viruses, conditions can be modified such that the majority of the propagated virus is the defective particle rather than the wild-type virus. Therefore this approach may be useful in generating high titer stocks of recombinant virus. However, these stocks would necessarily contain some wild-type virus.

Alternatively, synthetic RNPs may be replicated in cells co-infected with recombinant viruses that express the RS virus polymerase proteins. In fact, this method may be used to rescue recombinant infectious virus in accordance with the invention. To this end, the RSV virus polymerase proteins may be expressed in any expression vector/host cell system, including but not limited to viral expression vectors (e.g., vaccinia virus, adenovirus, baculovirus, etc.) or cell lines that express the polymerase proteins (e.g., see Krystal et al., 1986, Proc. Natl. Acad. Sci. USA 83: 2709-2713).

5.4. Generation of Chimeric Viruses with an Attenuated Phenotype

The methods of present invention may be used to introduce mutations or heterologous sequences to generate chimeric attenuated viruses which have many applications, including analysis of RSV molecular biology, pathogenesis, and growth and infection properties. In accordance with the present invention, mutations or heterologous sequences may be introduced for example into the F or G protein coding sequences, NS1, NS2, M1ORF, M2ORF, N, P, or L coding sequences. In yet another embodiment of the present invention, a particular viral gene, or the expression thereof, may be eliminated to generate an attenuated phenotype, e.g., the M ORF may be deleted from the RSV genome to generate a recombinant RSV with an attenuated phenotype. In yet another embodiment, the individual internal genes of human RSV can be replaced by another strains counterpart, or their bovine or murine counterpart. This may include part or all of one or more of the NS1, NS2, N, P, M, SH, M2(ORF1), M2(ORF2) and L genes or the G and F genes. The RSV genome contains ten mRNAs encoding three transmembrane proteins, G protein, fusion F protein required for penetration, and the small SH protein; the nucleocapsid proteins N, P and L; transcription elongation factor M2 ORF 1; the matrix M protein and two nonstructural proteins, NS1 and NS2. Any one of the proteins may be targeted to generate and attenuated phenotype. Other mutations which may be utilized to result in an attenuated phenotype are insertional, deletional and site directed mutations of the leader and trailer sequences.

In accordance with the present invention, an attenuated RSV exhibits a substantially lower degree of virulence as compared to a wild-type virus, including a slower growth rate, such that the symptoms of viral infection do not occur in an immunized individual.

In accordance with the present invention attenuated recombinant RSV may be generated by incorporating a broad range of mutations including single nucleotide changes, site-specific mutations, insertions, substitutions, deletions, or rearrangements. These mutations may affect a small segment of the RSV genome, e.g., 15 to 30 nucleotides, or large segments of the RSV genome, e.g., 50 to 1000 nucleotides, depending on the nature of the mutation. In yet another embodiment, mutations are introduced upstream or downstream of an existing cis-acting regulatory element in order to ablate its activity, thus resulting in an attentuated phenotype.

In accordance with the invention, a non-coding regulatory region of a virus can be altered to down-regulate any viral gene, e.g. reduce transcription of its mRNA and/or reduce replication of vRNA (viral RNA), so that an attenuated virus is produced.

Alterations of non-coding regulatory regions of the viral genome which result in down-regulation of replication of a viral gene, and/or down-regulation of transcription of a viral gene will result in the production of defective particles in each round of replication; i.e. particles which package less than the full complement of viral segments required for a fully infectious, pathogenic virus. Therefore, the altered virus will demonstrate attenuated characteristics in that the virus will shed more defective particles than wild type particles in each round of replication. However, since the amount of protein synthesized in each round is similar for both wild type virus and the defective particles, such attenuated viruses are capable of inducing a good immune response.

The foregoing approach is equally applicable to both segmented and non-segmented viruses, where the down regulation of transcription of a viral gene will reduce the production of its mRNA and the encoded gene product. Where the viral gene encodes a structural protein, e.g., a capsid, matrix, surface or envelope protein, the number of particles produced during replication will be reduced so that the altered virus demonstrates attenuated characteristics; e.g., a titer which results in subclinical levels of infection. For example, a decrease in viral capsid expression will reduce the number of nucleocapsids packaged during replication, whereas a decrease in expression of the envelope protein may reduce the number and/or infectivity of progeny virions. Alternatively, a decrease in expression of the viral enzymes required for replication, e.g., the polymerase, replicase, helicase, and the like, should decrease the number of progeny genomes generated during replication. Since the number of infectious particles produced during replication are reduced, the altered viruses demonstrated attenuated characteristics. However, the number of antigenic virus particles produced will be sufficient to induce a vigorous immune response.

An alternative way to engineer attenuated viruses involves the introduction of an alteration, including but not limited to an insertion, deletion or substitution of one or more amino acid residues and/or epitopes into one or more of the viral proteins. This may be readily accomplished by engineering the appropriate alteration into the corresponding viral gene sequence. Any change that alters the activity of the viral protein so that viral replication is modified or reduced may be accomplished in accordance with the invention.

For example, alterations that interfere with but do not completely abolish viral attachment to host cell receptors and ensuing infection can be engineered into viral surface antigens or viral proteases involved in processing to produce an attenuated strain. According to this embodiment, viral surface antigens can be modified to contain insertions, substitution or deletions of one or more amino acids or epitopes that interfere with or reduce the binding affinity of the viral antigen for the host cell receptors. This approach offers an added advantage in that a chimeric virus which expresses a foreign epitope may be produced which also demonstrates attenuated characteristics. Such viruses are ideal candidates for use as live recombinant vaccines. For example, heterologous gene sequences that can be engineered into the chimeric viruses of the invention include, but are not limited to, epitopes of human immunodeficiency virus (HIV) such as gp120; hepatitis B virus surface antigen (HBsAg); the glycoproteins of herpes virus (e.g., gD, gE); VP1 of poliovirus; and antigenic determinants of nonviral pathogens such as bacteria and parasites, to name but a few.

In this regard, RSV is an ideal system in which to engineer foreign epitopes, because the ability to select from thousands of virus variants for constructing chimeric viruses obviates the problem of host resistance or immune tolerance encountered when using other virus vectors such as vaccinia.

In another embodiment, alterations of viral proteases required for processing viral proteins can be engineered to produce attenuation. Alterations which affect enzyme activity and render the enzyme less efficient in processing, should affect viral infectivity, packaging, and/or release to produce an attenuated virus.

In another embodiment, viral enzymes involved in viral replication and transcription of viral genes, e.g., viral polymerases, replicases, helicases, etc. may be altered so that the enzyme is less efficient or active. Reduction in such enzyme activity may result in the production of fewer progeny genomes and/or viral transcripts so that fewer infectious particles are produced during replication.

The alterations engineered into any of the viral enzymes include but are not limited to insertions, deletions and substitutions in the amino acid sequence of the active site of the molecule. For example, the binding site of the enzyme could be altered so that its binding affinity for substrate is reduced, and as a result, the enzyme is less specific and/or efficient. For example, a target of choice is the viral polymerase complex since temperature sensitive mutations exist in all polymerase proteins. Thus, changes introduced into the amino acid positions associated with such temperature sensitivity can be engineered into the viral polymerase gene so that an attenuated strain is produced.

5.4.1. The RSV L Gene as a Target for Attenuatione

In accordance with the present invention, the RSV L gene is an important target to generate recombinant RSV with an attenuated phenotype. The L gene represents 48% of the entire RSV genome. The present invention encompasses generating L gene mutants with defined mutations or random mutations in the RSV L gene. Any number of techniques known to those skilled in the art may be used to generate both defined or random mutations into the RSV L gene. Once the mutations have been introduced, the functionality of the L gene cDNA mutants are screened in vitro using a minigenome replication system and the recovered L gene mutants are then further analyzed in vitro and in vivo.

The following strategies are exemplary of the approaches which may be used to generate mutants with an attenuated phenotype. Further, the following strategies as described below have been applied to the L gene only by way of example and may also be applied to any of the other RSV genes.

One approach to generate mutants with an attenuated phenotype utilizes a scanning mutagenesis approach to mutate clusters of charged amino acids to alanines. This approach is particularly effective in targeting functional domains, since the clusters of charged amino acids generally are not found buried within the protein structure. Replacing the charged amino acids with conservative substitutions, such as neutral amino acids, e.g., alanine, should not grossly alter the structure of the protein but rather, should alter the activity of the functional domain of the protein. Thus, disruption of charged clusters should interfere with the ability of that protein to interact with other proteins, thus making the mutated protein's activity thermosensitive which can yield temperature sensitive mutants.

A cluster of charged amino acids may be arbitrarily defined as a stretch of five amino acids in which at least two or more residues are charged residues. In accordance with the scanning mutagenesis approach all of the charged residues in the cluster are mutated to alanines using site-directed mutagenesis. Due to the large site of the RSV L gene, there are many clustered charged residues. Within the L gene, there are at least two clusters of four contiguous charged residues and at least seventeen clusters of three contiguous charged residues. At least two to four of the charged residues in each cluster may be substituted with a neutral amino acid, e.g., alanine.

In yet another approach to generate mutants with an attenuated phenotype utilizes a scanning mutagenesis approach to mutate cysteines to amino acids, such as glycines or alanines. Such an approach takes advantage of the frequent role of cysteines in intramolecular and intermolecular bond formations, thus by mutating cysteines to another residue, such as a conservative substitution e.g., valine or alanine, or a drastic substitution e.g., aspartic acid, the stability and function of a protein may be altered due to disruption of the protein's tertiary structure. There are approximately thirty-nine cysteine residues present in the RSV L gene.

In yet another approach random mutagenesis of the RSV L gene will cover residues other than charged or cysteines. Since the RSV L gene is very large, such an approach may be accomplished by mutagenizing large cDNA fragments of the L gene by PCR mutagenesis. The functionality of such mutants may be screened by a minigenome replication system and the recovered mutants are then further analyzed in vitro and in vivo.

5.5. Vaccine Formulations Using the Chimeric Viruses

Virtually any heterologous gene sequence may be constructed into the chimeric viruses of the invention for use in vaccines. In a preferred embodiment, the present invention relates to bivalent RSV vaccines which confers protection against RSV-A and RSV-B. To formulate such a vaccine, a chimeric RS virus is used which expresses the antigenic polypeptides of both RSV-A and RSV-B subtypes. In yet another preferred embodiment, the present invention relates to a bivalent vaccine which confers protection against both RSV and influenza. To formulate such a vaccine, a chimeric RS virus is used which expresses the antigenic polypeptides of both RSV and influenza.

Preferably, epitopes that induce a protective immune response to any of a variety of pathogens, or antigens that bind neutralizing antibodies may be expressed by or as part of the chimeric viruses. For example, heterologous gene sequences that can be constructed into the chimeric viruses of the invention for use in vaccines include but are not limited to sequences derived from a human immunodeficiency virus (HIV), preferably type 1 or type 2. In a preferred embodiment, an immunogenic HIV-derived peptide which may be the source of an antigen may be constructed into a chimeric influenza virus that may then be used to elicit a vertebrate immune response.

Such HIV-derived peptides may include, but are not limited to sequences derived from the env gene (i.e., sequences encoding all or part of gp160, gp120, and/or gp41), the pol gene (i.e., sequences encoding all or part of reverse transcriptase, endonuclease, protease, and/or integrase), the gag gene (i.e., sequences encoding all or part of p7, p6, p55, p17/18, p24/25), tat, rev, nef, vif, vpu, vpr, and/or vpx.

Other heterologous sequences may be derived from hepatitis B virus surface antigen (HBsAg); the glycoproteins of herpes virus (e.g. gD, gE); VP1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the chimeric viruses of the invention.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

In this regard, the use of genetically engineered RSV (vectors) for vaccine purposes may require the presence of attenuation characteristics in these strains. Current live virus vaccine candidates for use in humans are either cold adapted, temperature sensitive, or passaged so that they derive several (six) genes from avian viruses, which results in attenuation. The introduction of appropriate mutations (e.g., deletions) into the templates used for transfection may provide the novel viruses with attenuation characteristics. For example, specific missense mutations which are associated with temperature sensitivity or cold adaption can be made into deletion mutations. These mutations should be more stable than the point mutations associated with cold or temperature-sensitive mutants and reversion frequencies should be extremely low.

Alternatively, chimeric viruses with "suicide" characteristics may be constructed. Such viruses would go through only one or a few rounds of replication in the host. When used as a vaccine, the recombinant virus would go through a single replication cycle and induce a sufficient level of immune response but it would not go further in the human host and cause disease. Recombinant viruses lacking one or more of the essential RS virus genes would not be able to undergo successive rounds of replication. Such defective viruses can be produced by co-transfecting reconstituted RNPs lacking a specific gene(s) into cell lines which permanently express this gene(s). Viruses lacking an essential gene(s) will be replicated in these cell lines but when administered to the human host will not be able to complete a round of replication. Such preparations may transcribe and translate—in this abortive cycle—a sufficient number of genes to induce an immune response. Alternatively, larger quantities of the strains could be administered, so that these preparations serve as inactivated (killed) virus vaccines. For inactivated vaccines, it is preferred that the heterologous gene product be expressed as a viral component, so that the gene product is associated with the virion. The advantage of such preparations is that they contain native proteins and do not undergo inactivation by treatment with formalin or other agents used in the manufacturing of killed virus vaccines.

In another embodiment of this aspect of the invention, inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or β-propiolactone, and pooled. The resulting vaccine is usually inoculated intramuscularly.

Inactivated viruses may be formulated with a suitable adjuvant in order to enhance the immunological response. Such adjuvants may include but are not limited to mineral gels, e.g., aluminum hydroxide; surface active substances such as lysolecithin, pluronic polyols, polyanions; peptides; oil emulsions; and potentially useful human adjuvants such as BCG and *Corynebacterium parvum*.

Many methods may be used to introduce the vaccine formulations described above, these include but are not limited to oral, intradermal, intramuscular, intraperitoneal, intravenous, subcutaneous, and intranasal routes. It may be preferable to introduce the chimeric virus vaccine formulation via the natural route of infection of the pathogen for which the vaccine is designed. Where a live chimeric virus vaccine preparation is used, it may be preferable to introduce the formulation via the natural route of infection for influenza virus. The ability of RSV and influenza virus to induce a vigorous secretory and cellular immune response can be used advantageously. For example, infection of the respiratory tract by chimeric RSV or influenza viruses may induce a strong secretory immune response, for example in the urogenital system, with concomitant protection against a particular disease causing agent.

The following sections describe by way of example, and not by limitation, the manipulation of the negative strand RNA viral genomes using RSV as an example to demonstrate the applicability of the methods of the present invention to generate chimeric viruses for the purposes of heterologous gene expression, generating infectious viral particles and attenuated viral particles for the purposes of vaccination.

6. Rescue of Infectious Respiratory Syncytial Viruses (RSV) Using RNA Derived from Specific Recombinant DNAS This example describes a process for the rescue of infectious respiratory syncytial virus (RSV), derived from recombinant cDNAs encoding the entire RSV RNA genome into stable and infectious RSVs, as noted in Section 5 above. The method described may be applied to both segmented and non-segmented RNA viruses, including orthomyxovirus, paramyxovirus, e.g., Sendai virus, parainfluenza virus types 1-4, mumps, newcastle disease virus; morbillivirus, e.g., measles, canine distemper virus, rinderpest virus; pneumovirus, e.g., respiratory syncytial virus; rhabdovirus, e.g., rabies, vesiculovirus, vesicular stomatitis virus; but is described by way of example in terms of RSV. This process can be used in the production of chimeric RSV viruses which can express foreign genes, i.e., genes non-native to RSV, including other viral proteins such as the HIV env protein. Another exemplary way to achieve the production of chimeric RSV involves modifying existing, native RSV genes, as is further described. Accordingly, this example also describes the utility of this process in the directed attenuation of RSV pathogenicity, resulting in production of a vaccine with defined, engineered biological properties for use in humans.

The first step of the rescue process involving the entire RSV RNA genome requires synthesis of a full length copy of the 15 kilobase (Kb) genome of RSV strain A2. This is accomplished by splicing together subgenomic double strand cDNAs (using standard procedures for genetic manipulation) ranging in size from 1 kb-3.5 kb, to form the complete genomic cDNA. Determination of the nucleotide sequence of the genomic cDNA allows identification of errors introduced during the assembly process; errors can be corrected by site directed mutagenesis, or by substitution of the error region with a piece of chemically synthesized double strand DNA. Following assembly, the genomic cDNA is positioned adjacent to a transcriptional promoter (e.g., the T7 promoter) at one end and DNA sequence which allows transcriptional termination at the other end, e.g., a specific endonuclease or a ribozyme, to allow synthesis of a plus or minus sense RNA copy of the complete virus genome in vitro or in cultured cells. The leader or trailer sequences may contain additional sequences as desired, such as flanking ribozyme and tandem T7 transcriptional terminators. The ribozyme can be a hepatitis delta virus ribozyme or a hammerhead ribozyme and functions to yield an exact 3' end free of non-viral nucleotides.

In accordance with this aspect of the invention, mutations, substitutions or deletions can be made to the native RSV genomic sequence which results in an increase in RSV promoter activity. Applicants have demonstrated that even an increase in RSV promoter activity greatly enhances the efficiency of rescue of RSV, allowing for the rescue of infectious RSV particles from a full-length RSV cDNA carrying the mutation. In particular, a point mutation at position 4 of the genome (C to G) results in a several fold increase in promoter activity and the rescue of infectious viral particles from a full-length RSV cDNA clone carrying the mutation.

The rescue process utilizes the interaction of full-length RSV strain A2 genome RNA, which is transcribed from the constructed cDNA, with helper RSV subgroup B virus proteins inside cultured cells. This can be accomplished in a number of ways. For example, full-length virus genomic RNA from RSV strain A2 can be transcribed in vitro and transfected into RSV strain B9320 infected cells, such as 293 cells using standard transfection protocols. In addition, in vitro transcribed genomic RNA from RSV strain A2 can be transfected into a cell line expressing the essential RSV strain A2 proteins (in the absence of helper virus) from stably integrated virus genes.

Alternatively, in vitro transcribed virus genome RNA (RSV strain A2) can also be transfected into cells infected with a heterologous virus (e.g., in particular vaccinia virus) expressing the essential helper RSV strain A2 proteins, specifically the N, P, L and M2/ORF1 proteins. In addition the in vitro transcribed genomic RNA may be transfected into cells infected with a heterologous virus, for example vaccinia virus, expressing T7 polymerase, which enables expression of helper proteins from transfected plasmid DNAs containing the helper N, P, L and M2/ORF1 genes.

As an alternative to transfection of in vitro transcribed genomic RNA, plasmid DNA containing the entire RSV cDNA construct may be transfected into cells infected with a heterologous virus, for example vaccinia virus, expressing the essential helper RSV strain A2 proteins and T7 polymerase, thereby enabling transcription of the entire RSV genomic RNA from the plasmid DNA containing the RSV cDNA construct. The vaccinia virus need not however, supply the helper proteins themselves but only the T7 polymerase; then helper proteins, may be expressed from transfected plasmids containing the RSV N, P, L and M2/ORF1 genes, appropriately positioned adjacent to their own T7 promoters.

When replicating virus is providing the helper function during rescue experiments, the B9320 strain of RSV is used, allowing differentiation of progeny rescue directed against RSV B9320. Rescued RSV strain A2 is positively identified by the presence of specific nucleotide 'marker' sequences inserted in the cDNA copy of the RSV genome prior to rescue.

The establishment of a rescue system for native, i.e., 'wild-type' RSV strain A2 allows modifications to be introduced into the cDNA copy of the RSV genome to construct chimeric RSV containing sequences heterologous in some manner to that of native RSV, such that the resulting rescued virus may be attenuated in pathogenicity to provide a safe and efficacious human vaccine as discussed in Section 5.4 above. The genetic alterations required to cause virus attenuation may be gross (e.g., translocation of whole genes and/or regulatory sequences within the virus genome), or minor (e.g., single or multiple nucleotide substitution(s), addition(s) and/or deletion(s) in key regulatory or functional domains within the virus genome), as further described in detail.

In addition to alteration(s) (including alteration resulting from translocation) of the RSV genetic material to provide heterologous sequence, this process permits the insertion of 'foreign' genes (i.e., genes non-native to RSV) or genetic components thereof exhibiting biological function or antigenicity in such a way as to give expression of these genetic elements; in this way the modified, chimeric RSV can act as an expression system for other heterologous proteins or genetic elements, such as ribozymes, anti-sense RNA, specific oligoribonucleotides, with prophylactic or therapeutic potential, or other viral proteins for vaccine purposes.

6.1. Rescue of the Leader and Trailer Sequences of RSV Strain A2 Using RSV Strain B9320 as Helper Virus

6.1.1. Viruses and Cells

Although RSV strain A2 and RSV strain B9320 were used in this Example, they are exemplary. It is within the skill in the art to use other strains of RSV subgroup A and RSV subgroup B viruses in accordance with the teachings of this Example. Methods which employ such other strains are encompassed by the invention.

RSV strain A2 and RSV strain B9320 were grown in Hep-2 cells and Vero cells respectively, and 293 cells were used as host during transfection/rescue experiments. All three cell lines were obtained from the ATCC (Rockville, Md.).

6.1.2. Construction & Functional Analysis of Reporter Plasmids

Plasmid pRSVA2CAT (FIG. 1) was constructed as described below.

The cDNAs of the 44 nucleotide leader and 155 nucleotide trailer components of RSV strain A2 (see Mink et al., Virology 185:615-624 (1991); Collins et al., Proc. Natl. Acad. Sci. 88:9663-9667 (1991)), the trailer component also including the promoter consensus sequence of bacteriophage T7 polymerase, were separately assembled by controlled annealing of oligonucleotides with partial overlapping complementarity (see FIG. 1). The oligonucleotides used in the annealing were synthesized on an Applied Biosystems DNA synthesizer (Foster City, Calif.). The separate oligonucleotides and their relative positions in the leader and trailer sequences are indicated in FIG. 1. The oligonucleotides used to construct the leader were:

```
1. 5' CGA CGC ATA TTA CGC GAA AAA ATG CGT
   ACA ACA AAC TTG CAT AAA C (SEQ ID NO 1)

2. 5' CAA AAA AAT GGG GCA AAT AAG AAT TTG
   ATA AGT ACC ACT TAA ATT TAA CT (SEQ ID NO 2)

3. 5' CTA GAG TTA AAT TTA AGT GGT ACT (SEQ ID NO 3)

4. 5' TAT CAA ATT CTT ATT TGC CCC ATT TTT
   TTG GTT TAT GCA AGT TTG TTG TA (SEQ ID NO 4)

5. 5' CGC ATT TTT TCG CGT AAT ATG CGT CGG
   TAC (SEQ ID NO 5)
```

The oligonucleotides used to construct the trailer were:

```
1. 5' GTA TTC AAT TAT AGT TAT TAA AAA TTA AAA ATC
   ATA TAA TTT TTT AAA TA (SEQ ID NO 6)

2. 5' ACT TTT AGT GAA CTA ATC CTA AAG TTA TCA TTT
   TAA TCT TGG AGG AAT AA (SEQ ID NO 7)

3. 5' ATT TAA ACC CTA ATC TAA TTG GTT TAT ATG TGT
   ATT AAC TAA ATT ACG AG (SEQ ID NO 8)

4. 5' ATA TTA GTT TTT GAC ACT TTT TTT CTC GTT ATA
   GTG AGT CGT ATT A (SEQ ID NO 9)

5. 5' AGC TTA ATA CGA CTC ACT ATA ACG A
   (SEQ ID NO 10)

6. 5'GAA AAA AAG TGT CAA AAA CTA ATA TCT CGT AAT
   TTA GTT AAT ACA CAT AT (SEQ ID NO 11)

7. 5' AAA CCA ATT AGA TTA GGG TTT AAA TTT ATT CCT
   CCA AGA TTA AAA TGA TA (SEQ ID NO 12)

8. 5' ACT TTA GGA TTA GTT CAC TAA AAG TTA TTT AAA
   AAA TTA TAT GAT TTT TA (SEQ ID NO 13)

9. 5' ATT TTT AAT AAC TAT AAT TGA ATA CTG CA
   (SEQ ID NO 14)
```

The complete leader and trailer cDNAs were then ligated to the chloramphenicol-acetyl-transferase (CAT) reporter gene XbaI and PstI sites respectively to form a linear—1 kb RSV/CAT cDNA construct. This cDNA construct was then ligated into the Kpn I and Hind II sites of pUC19. The integrity of the final pRSVA2CAT construct was checked by gel analysis for the size of the Xba I/Pst I and Kpn I/Hind II digestion products. The complete leader and trailer cDNAs were also ligated to the green fluorescent protein (GFP) gene using appropriate restriction enzyme sites to form a linear cDNA construct. The resulting RSV-GFP-CAT is a bicistronic reporter construct which expresses both CAT and GFP.

In vitro transcription of Hga I linearlized pRSVA2CAT with bacteriophage T7 polymerase was performed according to the T7 supplier protocol (Promega Corporation, Madison, Wis.). Confluent 293 cells in six-well dishes (~1×10$^6$ cells per well) were infected with RSV strain B9320 at 1 plaque forming units (p.f.u.) per cell and 1 hour later were transfected with 5-10 μg of the in vitro transcribed RNA from the pRSVA2CAT construct. The transfection procedure followed the transfection procedure of Collins et al., Virology 195:252-256 (1993) and employed Transect/ACT™ and Opti-MEM reagents according to the manufacturers specifications (Gibco-BRL, Bethesda, Md.). At 24 hours post-infection the 293 cells were assayed for CAT activity using a standard protocol (Current Protocols in Molecular Biology, Vol. 1, Chapter 9.6.2; Gorman, et al., 1982) Mol. Cell Biol. 2: 1044-1051). The detection of high levels of CAT activity indicated that in vitro transcribed negative sense RNA containing the 'leader' and 'trailer' regions of the RSV A2 strain genome and the CAT gene can be encapsidated, replicated and expressed using proteins supplied by RSV strain B9320 (See FIG. 2). The level of CAT activity observed in these experiments was at least as high as that observed in similar rescue experiments where homologous RSV strain A2 was used as helper virus. The ability of an antigenically distinct subgroup B RSV strain B9320 to support the encapsidation, replication and transcription of a subgroup A RSV strain A2 RNA has to our knowledge hitherto not been formally reported.

6.2. Construction of a cDNA Representing the Complete Genome of RSV

To obtain a template for cDNA synthesis, RSV genomic RNA, comprising 15,222 nucleotides, was purified from infected Hep-2 cells according to the method described by Ward et al., J. Gen. Virol. 64:167-1876 (1983). Based on the published nucleotide sequence of RSV, oligonucleotides were synthesized using an Applied Biosystems DNA synthesizer (Applied Biosystems, Foster City, Calif.) to act as primers for first and second strand cDNA synthesis from the genomic RNA template. The nucleotide sequences and the relative positions of the cDNA primers and key endonuclease sites within the RSV genome are indicated in FIG. 3. The production of cDNAs from virus genomic RNA was carried out according to the reverse transcription/polymerase chain reaction (RT/PCR) protocol of Perkin Elmer Corporation, Norwalk, Conn. (see also Wang et al., (1989) Proc. Natl. Acad. Sci. 86:9717-9721); the amplified cDNAs were purified by electroelution of the appropriate DNA band from agarose gels. Purified DNA was ligated directly into the PCRII plasmid vector (Invitrogen Corp. San Diego), and transformed into either 'One Shot E. coli cells (Invitrogen) or 'SURE' E. coli cells (Stratagene, San Diego). The resulting, cloned, virus specific, cDNAs were assembled by standard cloning techniques (Sambrook et al., Molecular Cloning—A Laboratory Manual, Cold Spring Harbor laboratory Press (Cold Spring Harbor, N.Y., 1989) to produce a cDNA spanning the complete RSV genome. The entire cDNA genome was sequenced, and incorrect sequences were replaced by either site-directed mutagenesis or chemically synthesized DNA. Nucleotide substitutions were introduced at bases 7291 and 7294 (with base number 1 being at the start of the genomic RNA 3' end) in the 'F' gene, to produce a novel Stu I endonuclease site, and at positions 7423, 7424, and 7425 (also in the F gene) to produce a novel Pme I site. These changes were designed to act as definitive markers for rescue events. The bacteriophage T7 polymerase and the Hga I endonuclease site were placed at opposite ends of the virus genome cDNA such that either negative or positive sense virus genome RNA can be synthesized in vitro. The cDNAs representing the T7 polymerase promoter sequence and the recognition sequence for Hga I were synthesized on an Applied Biosystems DNA synthesizer and were separately ligated to the ends of the virus genome cDNA, or were added as an integral part of PCR primers during amplification of the terminal portion of the genome cDNA, where appropriate; the latter procedure was used when suitable endonuclease sites near the genome cDNA termini were absent, preventing direct ligation of chemically synthesized T7 promoter/Hga I site cDNA to the genome cDNA. This complete construct (genome cDNA and flanking T7 promoter/Hga I recognition sequence) was then cloned into the Kpn I/Not I sites of the Bluescript II SK phagemid (Stratagene, San Diego) from which the endogenous T7 promoter has been removed by site-directed mutagenesis. RNA transcribed from this complete genome construct may be rescued using RSV subgroup B helper virus to give infectious RSV in accordance with Example 6.1. This basic rescue system for the complete native, i.e., 'wild-type' RSV A2 strain genomic RNA can be employed to introduce a variety of modifications into the cDNA copy of the genome resulting in the introduction of heterologous sequences into the genome. Such changes can be designed to reduce viral pathogenicity without restricting virus replication to a point where rescue becomes impossible or where virus gene expression is insufficient to stimulate adequate immunity.

The following oligonucleotides were used to construct the ribozyme/T7 terminator sequence:

```
                                              (SEQ ID NO 31)
        5' GGT*GGCCGGCATGGTCCCAGC
        3' CCA CCGGCCGTACCAGGGTCG (SEQ ID NO 32)
        CTCGCTGGCGCCGGCTGGGCAACA
        GAGCGACCGCGGCCGACCCGTGTG
```

```
                                              (SEQ ID NO 33)
        TTCCGAGGGGACCGTCCCCTCGGT
        AAGGCTCCCCTGGCAGGGGAGCCA (SEQ ID NO 34)
        AATGGCGAATGGGACGTCGACAGC
        TTACCGCTTACCCTGCAGCTGTCG (SEQ ID NO 35)
        TAACAAAGCCCGAAGGAAGCT
        ATTGTTTCGGGCTTCCTTCGA (SEQ ID NO 36)
        GAGTTGCTGCTGCCACCGTTG
        CTCAACGACGACGGAGGCAAC (SEQ ID NO 37)
        AGCAATAACTAGATAACCTTGGG
        TCGTTATTGATCTATTGGAACCC (SEQ ID NO 38)
        CCTCTAAACGGGTCTTGAGGGTCT
        GGAGATTTGCCCAGAACTCCCAGA (SEQ ID NO 39)
        TTTTGCTGAAAGGAGGAACTA
        AAAACGACTTTCCTCCTTGAT (SEQ ID NO 40)
        TATGCGGCCGCGTCGACGGTA
        ATACGCCGGCGEAGCTGCCAT (SEQ ID NO 41)
        CCGGGCCCGCCTTCGAAG3'
        GGCCCGGGCGGAAGCTTC5'
```

A cDNA clone containing the complete genome of RSV a T7 promoter, a hepatitis delta virus ribozyme and a T7 terminator was generated. This construct can be used to generate antigenomic RNA or RSV in vivo in the presence of T7 polymerase. Sequence analysis indicated that the plasmid contained few mutations in RSV genome.

6.2.1. Modifications of the RSV Genome

Modifications of the RSV RNA genome can comprise gross alterations of the genetic structure of RSV, such as gene shuffling. For example, the RSV M1 gene can be translocated to a position closer to the 5' end of the genome, in order to take advantage of the known 3' to 5' gradient in virus gene expression, resulting in reduced levels of M1 protein expression in infected cells and thereby reducing the rate of virus assembly and maturation. Other genes and/or regulatory regions may also be translocated appropriately, in some cases from other strains of RSV of human or animal origin. For example, the F gene (and possibly the 'G' gene) of the human subgroup B RSV could be inserted into an otherwise RSV strain A genome (in place or, or in addition to the RSV strain A F and G genes).

In another approach, the RNA sequence of the RSV viruses N protein can be translocated from its 3' proximal site to a position closer to the 5' end of the genome, again taking advantage of the 3' to 5' gradient in gene transcription to reduce the level of N protein produced. By reducing the level of N protein produced, there would result a concomitant increase in the relative rates of transcription of genes involved in stimulating host immunity to RSV and a concomitant reduction in the relative rate of genome replication. Thus, by translocating the RSV RNA sequence coding for RSV N protein, a chimeric RS virus having attenuated pathogenicity relative to native RSV will be produced.

Another exemplary translocation modification resulting in the production of attenuated chimeric RSV comprises the translocation of the RSV RNA sequence coding for the L protein of RSV. This sequence of the RS virus is believed responsible for viral polymerase protein production. By translocating the RSV sequence coding for L protein from its native 5' terminal location in the native RSV genome to a location at or near the 3' terminus of the genome, a chimeric RSV virus exhibiting attenuated pathogenicity will be produced. Yet another exemplary translocation comprises the switching the locations of the RSV RNA sequences coding for the RSV G and F proteins (i.e., relative to each other in the genome) to achieve a chimeric RSV having attenuated pathogenicity resulting from the slight modification in the amount of the G and F proteins produced. Such gene shuffling modifications as are exemplified and discussed above are believed to result in a chimeric, modified RSV having attenuated pathogenicity in comparison to the native RSV starting material. The nucleotide sequences for the foregoing encoded proteins are known, as is the nucleotide sequence for the entire RSV genome. See McIntosh, Respiratory Syncytial Virus in Virology, 2d Ed. edited by B. N. Fields, D. M. Knipe et al., Raven Press, Ltd. New York, 1990 Chapter 38, pp 1045-1073, and references cited therein.

These modifications can additionally or alternatively comprise localized, site specific, single or multiple, nucleotide substitutions, deletions or additions within genes and/or regulatory domains of the RSV genome. Such site specific, single or multiple, substitutions, deletions or additions can reduce virus pathogenicity without overly attenuating it, for example, by reducing the number of lysine or arginine residues at the cleavage site in the F protein to reduce efficiency of its cleavage by host cell protease (which cleavage is believed to be an essential step in functional activation of the F protein), and thereby possibly reduce virulence. Site specific modifications in the 3' or 5' regulatory regions of the RSV genome may also be used to increase transcription at the expense of genome replication. In addition, localized manipulation of domains within the N protein, which is believed to control the switch between transcription and replication can be made to reduce genome replication but still allow high levels of transcription. Further, the cytoplasmic domain(s) of the G and F glycoproteins can be altered in order to reduce their rate of migration through the endoplasmic reticulum and golgi of infected cells, thereby slowing virus maturation. In such cases, it may be sufficient to modify the migration of G protein only, which would then allow additional up-regulation of 'F' production, the main antigen involved in stimulating neutralizing antibody production during RSV infections. Such localized substitutions, deletions or additions within genes and/or regulatory domains of the RSV genome are believed to result in chimeric, modified RSV also having reduced pathogenicity relative to the native RSV genome.

6.3. Rescue of a cDNA Representing the Complete Genome of RSV

6.3.1. The Construction and Functional Analysis of Expression Plasmids

The RSV, N, P, and L genes encode the viral polymerase of RSV. The function of the RSV M genes is unknown. The ability of RSV, N, P, M, and L expression plasmids to serve the function of helper RSV strain AZ proteins was assessed as described below. The RSV, N, P, L, and M2-1 genes were cloned into the modified PCITE 2a(+) vector (Novagen, Madison, Wis.) under the control of the T7 promoter and flanked by a T7 terminator at it's 3' end. PCITE-2a(+) was modified by insertion of a T7 terminator sequence from PCITE-3a(+) into the Alwn I and Bgl II sites of pCITE-2a(+). The functionality of the N, P, and L expression plasmids was determined by their ability to replicate the transfected pRSVA2CAT. At approximately 80% confluency, Hep-2 cells in six-well plates were infected with MVA at a moi of 5. After 1 hour, the infected cells were transfected with pRSVA2CAT (0.5 mg), and plasmids encoding the N (0.4 mg), P (0.4 mg), and L (0.2 mg) genes using lipofecTACE (Life Technologies, Gaithersburg, Md.). The transfection proceeded for 5 hours or overnight and then the transfection medium was replaced with fresh MEM containing 2% (fetal bovine serum) FBS. Two days post-infection, the cells were lysed and the lysates were analyzed for CAT activity using Boehringer Mannheim's CAT ELISA kit. CAT activity was detected in cells that had been transfected with N, P, and L plasmids together with PRSVAZCAT. However, no CAT activity was detected when any one of the expression plasmids was omitted. Furthermore, co-transfection of RSV-GFP-CAT with the N, P, and L expression plasmids resulted in expression of both GFP and CAT proteins. The ratios of different expression plasmids and moi of the recombinant vaccina virus were optimized in the reporter gene expression system.

6.3.2. Recovery of Infectious RSV from the Complete RSV cDNA

Hep-2 cells were infected with MVA (recombinant vaccinia virus expressing T7 polymerase) at an moi of one. Fifty minutes later, transfection mixture was added onto the cells. The transfection mixture consisted of 2 μg of N expression vector, 2 μg of P expression vector, 1 μg of L expression vector, 1.25 μg of M2/ORF1 expression vector, 2 μg of RSV genome clone with enhanced promoter, 50 μl of Lipofec-TACE (Life Technologies, Gaithersburg, Md.) and 1 ml OPTI-MEM. One day later, the transfection mixture was replaced by MEM containing 2% FCS. The cells were incubated at 37° C. for 2 days. The transfection supernatant was harvested and used to infect fresh Hep-2 cells in the presence of 40 μg/ml arac (drug against vaccinia virus). The infected Hep2 cells were incubated for 7 days. After harvesting the P1 supernatant, cells were used for immunostaining using antibodies directed against F protein of RSV A2 strain. Six positively stained loci with visible cell-cell-fusion (typical for RSV infection) were identified. The RNA was extracted from P1 supernatant, and used as template for RT-PCR analysis. PCR products corresponding to F and M2 regions were generated. both products contained the introduced markers. In control, PCR products derived from natural RSV virus lacked the markers.

A point mutation was created at position 4 of the leader sequence of the RSV genome clone (C residue to G) and this genome clone was designated pRSVC4GLwt. This clone has been shown in a reporter gene context to increase the promoter activity by several fold compared to wild-type. After introduction of this mutation into the full-length genome, infectious virus was rescued from the cDNA clone. The rescued recombinant RSV virus formed smaller plaques than the wild-type RSV virus (FIG. 8).

This system allows the rescue mutated RSV. Therefore, it may be an excellent tool to engineer live-attenuated vaccines against RSV and to use RSV vector and viruses to achieve heterologous gene expression. It may be possible to express G protein of type B RSV into the type A background, so the vaccine is capable of protect both type A and type B RSV infection. It may also be possible to achieve attenuation and temperature sensitive mutations into the RSV genome, by changing the gene order or by site-directed mutagenesis of the L protein.

6.4. Use of Monoclonal Antibodies to Differentiate Rescued Virus from Helper Virus In order to neutralize the RSV strain B9320 helper virus and facilitate identification of rescued A 2 strain RSV, monoclonal antibodies against RSV strain B9320 were made as follows.

Six BALB/c female mice were infected intranasally (i.n.) with $10^5$ plaque forming units (p.f.u.) of RSV B9320, followed 5 weeks later by intraperitoneal (i.p.) inoculation with $10^6$-$10^7$ pfu of RSV B9320 in a mixture containing 50% complete Freund's adjuvant. Two weeks after i.p. inoculation, a blood sample from each mouse was tested for the presence of RSV specific antibody using a standard neutralization assay (Beeler and Coelingh, J. Virol. 63:2941-2950 (1988)). Mice producing the highest level of neutralizing antibody were then further boosted with $10^6$ p.f.u. of RSV strain B9320 in phosphate buffered saline (PBS), injected intravenously at the base of the tail. Three days later, the mice were sacrificed and their spleens collected as a source of monoclonal antibody producing B-cells. Splenocytes (including B-cells) were teased from the mouse spleen through incisions made in the spleen capsule into 5 ml of Dulbecco's Modified Eagle's Medium (DME). Clumps of cells were allowed to settle out, and the remaining suspended cells were separately collected by centrifugation at 2000×g for 5 minutes at room temperature. These cell pellets were resuspended in 15 ml 0.83 (W/V) $NH_4Cl$, and allowed to stand for 5 minutes to lyse red blood cells. Splenocytes were then collected by centrifugation as before through a 10 ml; cushion of fetal calf serum. The splenocytes were then rinsed in DME, repelleted and finally resuspended in 20 ml of fresh DME. These splenocytes were then mixed with Sp2/0 cells (a mouse myeloma cell line used as fusion partners for the immortalization of splenocytes) in a ratio of 10:1, spleen cells: Sp2/0 cells. Sp2/0 cells were obtained from the ATCC and maintained in DME supplemented with 10% fetal bovine serum. The cell mixture was then centrifuged for 8 minutes at 2000×g at room temperature. The cell pellet was resuspended in 1 ml of 50% polyethylene glycol 1000 mol. wt. (PEG 1000), followed by addition of equal volumes of DME at 1 minute intervals until a final volume of 25 ml was attained. The fused cells were then pelleted as before and resuspended at $3.5\times10^6$ spleen cells $ml^1$ in growth medium (50% conditioned medium from SP2/0 cells, 50% HA medium containing 100 ml RPMI 25 ml F.C.S., 100 µgml gentamicin, 4 ml 50×Hypoxanthine, Thymidine, Aminopterin (HAT) medium supplied as a prepared mixture of Sigma Chem. Co., St. Louis, Mo.). The cell suspension was distributed over well plates (200 µl $well^{-1}$) and incubated at 37° C., 95 humidity and 5% $CO_2$. Colonies of hybridoma cells (fused splenocytes and Sp2/0 cells) were then subcultured into 24 well plates and grown until nearly confluent; the supernatant growth medium was then sampled for the presence of RSV strain B9320 neutralizing monoclonal antibody, using a standard neutralization assay (Beeler and Coelingh, J. Virol. 63:2941-50 (1988)). Hybridoma cells from wells with neutralizing activity were resuspended in growth medium and diluted to give a cell density of 0.5 cells per 100 µl and plated out in 96 well plates, 200 µl per well. This procedure ensured the production of monoclones (i.e. hybridoma cell lines derived from a single cell) which were then reassayed for the production of neutralizing monoclonal antibody. Those hybridoma cell lines which produced monoclonal antibody capable of neutralizing RSV strain B9320 but not RSV strain A2 were subsequently infected into mice, i.p. ($10^6$ cells per mouse). Two weeks after the i.p. injection mouse ascites fluid containing neutralizing monoclonal antibody for RSV strain B9320 was tapped with a 19 gauge needle, and stored at −20° C.

This monoclonal antibody was used to neutralize the RSV strain B9320 helper virus following rescue of RSV strain A2 as described in Section 9.1. This was carried out by diluting neutralizing monoclonal antibody 1 in 50 with molten 0.4% (w/v) agar in Eagle's Minimal Essential Medium (EMEM) containing 1% F.C.S. This mixture was then added to Hep-2 cell monolayers, which had been infected with the progeny of rescue experiments at an m.o.i. of 0.1-0.01 p.f.u. per cell. The monoclonal antibody in the agar overlay inhibited the growth of RSV strain B9320, but allowed the growth of RSV strain A2, resulting in plaque formation by the A2 strain. These plaques were picked using a pasteur pipette to remove a plug a agar above the plaque and the infected cells within the plaque; the cells and agar plug were resuspended in 2 ml of EMEM, 1% FCS, and released virus was plaqued again in the presence of monoclonal antibody on a fresh Hep-2 cell monolayer to further purify from helper virus. The twice plaqued virus was then used to infect Hep-2 cells in 24 well plates, and the progeny from that were used to infect six-well plates at an m.o.i. of 0.1 p.f.u. per cell. Finally, total infected cell RNA from one well of a six-well plates was used in a RT/PCR reaction using first and second strand primers on either side of the 'marker sequences' (introduced into the RSV strain A2 genome to act as a means of recognizing rescue events) as described in Section 6.2 above. The DNA produced from the RT/PCR reaction was subsequently digested with Stu I and Pme I to positively identify the 'marker sequences' introduced into RSV strain A2 cDNA, and hence to establish the validity of the rescue process.

7. Rescue of Infectious RSV Particles in the Absence of M2 Expression

The following experiments were conducted to compare the efficiencies of rescue of RS virions in the presence and absence of the M2/ORF1 gene. If the M2/ORF1 gene function is not required to achieve rescue of RSV infectious particles, it should be possible to rescue RS virions in the absence of the expression of the M2/ORF1 gene function. In the present analysis, Hep-2 cells which are susceptible to RSV replication, were co-transfected with plasmids encoding the 'N', 'P' and 'L' genes of the viral polymerase of RSV and the cDNA corresponding to the full-length antigenome of RSV, in the presence or absence of plasmid DNA encoding the M2/ORF1 gene, and the number of RSV infectious units were measured in order to determine whether or not the M2/ORF1 gene product was required to rescue infectious RSV particles.

The following plasmids were used in the experiments described below: a cDNA clone encoding the full-length antigenome of RSV strain A2, designated pRSVC4GLwt; and plasmids encoding the N, P, and L polymerase proteins, and plasmid encoding the M2/ORF1 elongation factor, each downstream of a T7 RNA promoter, designated by the name of the viral protein encoded.

pRSVC4GLwt was transfected, together with plasmids encoding proteins N, P and L, into Hep-2 cells which had been pre-infected with a recombinant vaccinia virus expressing the T7 RNA polymerase (designated MVA). In another set of Hep-2 cells, pRSVC4GLwt was co-transfected with plasmids encoding the N, P and L polymerase proteins, and in addition a plasmid encoding the M2 function. Transfection and recovery of recombinant RSV were performed as follows: Hep-2 cells were split in six-well dishes (35 mm per well) 5 hours or 24 hours prior to transfection. Each well contained approximately $1 \times 10^6$ cells which were grown in MEM (minimum essential medium) containing 10% FBS (fetal bovine serum). Monolayers of Hep-2 cells at 70%-80% confluence were infected with MVA at a multiplicity of infection (moi) of 5 and incubated at 35° C. for 60 minutes. The cells were then washed once with OPTI-MEM (Life Technologies) and the medium of each dish replaced with 1 ml of OPTI-MEM and 0.2 ml of the transfection mixture. The transfection mixture was prepared by mixing the four plasmids, pRSVC4GLwt, N, P and L plasmids in a final volume of 0.1 ml OPTI-MEM at amounts of 0.5-0.6 µg of pRSVC4GLwt, 0.4 µg of N plasmid, 0.4 µg of P plasmid, and 0.2 µg of L plasmid. A second mixture was prepared which additionally included 0.4 µg M2/ORFI plasmid. The plasmid mixtures of 0.1 ml were combined with 0.1 ml of OPTI-MEM containing 10 µl of lipofecTACE (Life Technologies, Gaithersburg, Md.) to constitute the complete transfection mixture. After a 15 minute incubation at room temperature, the transfection mixture was added to the cells, and one day later this was replaced by MEM containing 2% FBS. Cultures were incubated at 35° C. for 3 days at which time the supernatants were harvested. Cells were incubated at 35° C. since the MVA virus is slightly temperature sensitive and is much more efficient at 35° C.

Three days post-transfection, the transfected cell supernatants were assayed for the presence of RSV infectious units by an immunoassay which would indicate the presence of RSV packaged particles (see Table I). In this assay, 0.3-0.4 ml of the culture supernatants were passaged onto fresh (uninfected) Hep-2 cells and overlaid with 1% methylcellulose and 1×L15 medium containing 2% FBS. After incubation for 6 days, the supernatant was harvested and the cells were fixed and stained by an indirect horseradish peroxidase method, using a goat anti-RSV antibody which recognizes the RSV viral particle (Biogenesis, Sandown, N.H.) followed by a rabbit anti-goat antibody conjugated to horseradish peroxidase. The antibody complexes that bound to RSV-infected cells were detected by the addition of a AEC-(3-amino-9-ethylcarbazole) chromogen substrate (DAKO) according to the manufacturer's instructions. The RSV plaques were indicated by a black-brown coloration resulting from the reaction between the chromogen substrate and the RSV-antibody complexes bound to the plaques. The number of RSV plaques is expressed as the number of plaque forming units (p.f.u.) per 0.5 ml of transfection supernatant (see Table I).

Comparisons of the amount of RS virions recovered from the supernatants of transfection dishes in the presence or absence of M2/ORFI are shown in Table I. The results of four separate experiments demonstrated that the absence of M2/ORF1 from the transfection assay did not diminish the number of infectious units of RSV observed. Thus, the results of these experiments clearly indicate that RSV can be rescued in the absence of the M2/ORF1 from cells transfected only with plasmids encoding the three polymerase proteins, N, P and L, and the cDNA encoding the full-length RSV antigenome. The rescue of true RS virions in the absence of M2/ORF1 was further indicated by the ability to passage the rescued recombinant RSV for up to six passages. Therefore, the production of RSV virions is not dependent on the expression of the M2/ORF1 gene, nor does the inclusion of the M2/ORF1 gene in the transfection assay increase the efficiency of true RSV rescue.

TABLE I

Production of infectious RSV through plasmid transfection is not dependent on expression of M2ORF1

| | Production of infectious RSV (pfu from 0.5 ml transfection supernatants) | |
|---|---|---|
| Expt. | +M2 ORF1 | −M2 ORF1 |
| 1. | 6, 10 (8) | 16, 9 (13) |
| 2. | 120, 46, 428 (198) | 100, 122, 105 (109) |
| 3. | 160, 180 (170) | 150, 133 (142) |
| 4. | 588, 253, 725 (522) | 300, 1000, 110 (470) |

Each experiment was done singly, in duplicates or triplicates. The average number of plaque forming units (pfu) from 0.5 ml transfected cell supernatants is shown in the brackets.

8. EXAMPLE

Expression of RSV Subgroup B-G and -F Proteins by RSV A2 Strain

The following experiments were conducted to generate a chimeric RSV which expresses the antigenic polypeptides of more than one strain of RSV. Two main antigenic subgroups (A and B) of respiratory syncytial virus (RSV) cause human diseases. Glycoproteins F and G are the two major antigenic determinants of RSV. The F glycoproteins of subgroup A and B viruses are estimated to be 50% related, while the relationship of G glycoproteins is considerably less, about 1-5%. Infection of RSV subgroup A induces either partial or no resistance to replication of a subgroup B strain and vice versa. Both subgroup A and subgroup B RSV virus vaccines are needed to protect from RSV infection.

The first approach described herein is to make an infectious chimeric RSV cDNA clone expressing subgroup B antigens by replacing the current infectious RSV A2 cDNA clone G and F region with subgroup B-G and -F genes. The chimeric RSV would be subgroup B antigenic specific. The second approach described herein is to insert subgroup B-G gene in the current A2 cDNA clone so that one virus would express both subgroup A and B specific antigens.

8.1. Substitution of A2 G and F by B9320 G and F Genes

RSV subgroup B strain B9320 G and F genes were amplified from B9320 vRNA by RT/PCR and cloned into pCRII vector for sequence determination. BamH I site was created in the oligonucleotide primers used for RT/PCR in order to clone the G and F genes from B9320 strain into A2 antigenomic cDNA (FIG. 4A). A cDNA fragment which contained G and F genes from 4326 nt to 9387 nt of A2 strain was first subcloned into pUC19 (pUCR/H). Bgl II sites were created at positions of 4630 (SH/G intergenic junction) and 7554 (F/M2 intergenic junction), respectively by Quickchange site-directed mutagenesis kit (Strategene, Lo Jolla, Calif.). B9320 G and F cDNA inserted in pCR.II vector was digested with BamH I restriction enzyme and then subcloned into Bgl II digested pUCR/H which had the A2 G and F genes removed. The cDNA clone with A2 G and F genes replaced by B9320 G and F was used to replace the Xho I to Msc I region of the full-length A2 antigenomic cDNA. The resulting antigenomic cDNA clone was termed pRSVB-GF and was used to transfect Hep-2 cells to generate infectious RSVB-GF virus.

Generation of chimeric RSVB-GF virus was as follows, pRSVB-GF was transfected, together with plasmids encoding proteins N, P, L and M2/ORF1, into Hep-2 cells which had been infected with MVA, a recombinant vaccinia virus which expresses the T7 RNA polymerase. Hep-2 cells were split a day before transfection in six-well dishes. Monolayers of Hep-2 cells at 60%-70% confluence were infected with MVA at moi of 5 and incubated at 35° C. for 60 min. The cells were then washed once with OPTI-MEM (Life Technologies, Gaithersburg, Md.). Each dish was replaced with 1 ml of OPTI-MEM and added with 0.2 ml of transfection medium. The transfection medium was prepared by mixing five plasmids in a final volume of 0.1 ml of OPTI-MEM medium, namely 0.6 µg of RSV antigenome pRSVB-GF, 0.4 µg of N plasmid, 0.4 µg of P plasmid, 0.2 µg of L plasmid and 0.4 µg of M2/ORF1 plasmid. This was combined with 0.1 ml of OPTI-MEM containing 10 µl lipofecTACE (Life Technologies, Gaithersburg, Md. U.S.A.). After a 15 minute incubation at room temperature, the DNA/lipofecTACE was added to the cells and the medium was replaced one day later by MEM containing 2% FBS. Cultures were further incubated at 35° C. for 3 days and the supernatants harvested. Aliquots of culture supernatants (PO) were then used to infect fresh Hep-2 cells. After incubation for 6 days at 35° C., the supernatant was harvested and the cells were fixed and stained by an indirect horseradish peroxidase method using goat anti-RSV antibody (Biogenesis, Sandown, N.H.) followed by a rabbit anti-goat antibody linked to horseradish peroxidase. The virus infected cells were then detected by addition of substrate chromogen (DAKO, Carpinteria, Calif., U.S.A.) according to the manufacturer's instructions. RSV-like plaques were detected in the cells which were infected with the supernatants from cells transfected with pRSVB-GF. The virus was further plaque purified twice and amplified in Hep-2 cells.

Recombinant RSVB-GF virus was characterized by RT/PCR using RSV subgroup B specific primers. Two independently purified recombinant RSVB-GF virus isolates were extracted with an RNA extraction kit (Tel-Test, Friendswood, Tex.) and RNA was precipitated by isopropanol. Virion RNAs were annealed with a primer spanning the RSV region from nt 4468 to 4492 and incubated for 1 hr under standard RT conditions (10 µl reactions) using superscript reverse transcriptase (Life Technologies, Gaithersburg, Md.). Aliquots of each reaction were subjected to PCR (30 cycles at 94° C. for 30 s, 55° C. for 30 s and 72° C. for 2 min) using subgroup B specific primers in region (CACCACCTACCT-TACTCAAGT (SEQ ID NO 42) and TTTGTTTGTGGGTTTGATGGTTGG). (SEQ ID NO 43) The PCR products were analyzed by electrophoresis on 1% agarose gel and visualized by staining with ethidium bromide. As shown in FIG. 5, no DNA product was produced in RT/PCR reactions using RSV A2 strain as template. However, a predicted product of 254 bp was detected in RT/PCR reactions utilizing RSVB-GF RNA or the PCR control plasmid, pRSVB-GF DNA, as template, indicating the rescued virus contained G and F genes derived form B9320 virus.

8.2. Expression of B9320G by RSV A2 Virus

RSV subgroup B strain B9320 G gene was amplified from B9320 vRNA by RT/PCR and cloned into pCRII vector for sequence determination. Two Bgl II sites were incorporated into the PCR primers which also contained gene start and gene end signals (GATATCAAGATCTACAATAACAT-TGGGGCAAATGC (SEQ ID NO 44) and GCTAA-GAGATCTTTTTGAATAACTAAGCATG). (SEQ ID NO 45) B9320G cDNA insert was digested with Bgl II and cloned into the SH/G (4630 nt) or F/M2 (7552 nt) intergenic junction of a A2 cDNA subclone (FIG. 4B and FIG. 4C). The Xho I to Msc I fragment containing B9320G insertion either at SH/G or F/M2 intergenic region was used to replace the corresponding Xho I to Msc I region of the A2 antigenomic cDNA. The resulting RSV antigenomic cDNA clone was termed as pRSVB9320G-SH/G or pRSVB9320G-F/M2.

Generation of RSV A2 virus which had B9320 G gene inserted at F/M2 intergenic region was performed similar to what has described for generation of RSVB-GF virus. Briefly, pRSVB9320G-F/M2 together with plasmids encoding proteins N, P and L were transfected, into Hep-2 cells, infected with a MVA vaccinia virus recombinant, which expresses the T7 RNA polymerase (Life Technologies, Gaithersburg, Md.). The transfected cell medium was replaced by MEM containing 2% fetal bovine serum (FBS) one day after transfection and further incubated for 3 days at 35° C. Aliquots of culture supernatants (PO) were then used to infect fresh Hep-2 cells. After incubation for 6 days at 35° C., the supernatant was harvested and the cells were fixed and stained by an indirect horseradish peroxidase method using goat anti-RSV antibody (Biogenesis) followed by a rabbit anti-goat antibody linked to horseradish peroxidase. The virus infected cells were then detected by addition of substrate chromogen (Dako). RSV-like plaques were detected in the cells which were infected with the supernatants from cells transfected with pRSVB9320G/F/M2.

Characterization of pRSVB9320G-F/M2 virus was performed by RT/PCR using B9320G specific primers. A predicted PCR product of 410 bp was seen in RT/PCR sample using pRSVB9320G-F/M2 RNA as template, indicating the rescued virus contained G gene derived from B9320. (FIG. 6)

Expression of the inserted RSV B9320 G gene was analyzed by Northern blot using a $^{32}$P-labeled oligonucleotide specific to A2-G or B-G mRNA. Total cellular RNA was extracted from Hep-2 cells infected with wild-type RSVB 9320, rRSVA2, or rRSVB9320G-F/M2 48 hours postinfection using an RNA extraction kit (RNA stat-60, Tel-Test). RNA was electrophoresed on a 1.2% agaorse gel containing formaldehyde and transferred to a nylon membrane (Amersham). An oligonucleotide specific to the G gene of the A2 stain (5'TCTTGACTGTTGTGGATTGCAGGGT-TGACTTGACTCCGATCGATCC-3') (SEQ ID NO 46) and an oligonucleotide specific to the B9320 G gene (5'CTTGT-GTTGTTGTTGTATGGTGTGTTTCT-GATTTTGTATTGATCGATCC-3') (SEQ ID NO 47) were labeled with $^{32}$P-ATP by a kinasing reaction known to those of ordinary skill in the art. Hybridization of the membrane with one of the $^{32}$P-labeled G gene specific oligonucletodies was performed at 65° C. and washed according to standard procedure. Both A2-G and B9320-G specific RNA were detected in the rRSVB9320G-F1M2 infected Hep-2 Cells. (FIG. 6B) These results demonstrate subtype specific RNA expression.

Protein expression of the chimeric rRSVA2(B-G) was compared to that of RSV B9320 and rRSV by immunoprecipitation of $^{35}$S-labeled infected Hep-2 cell lysates. Briefly, the virus infected cells were labeled with $^{35}$S-promix (100 µCi/ml $^{35}$S-Cys and $^{35}$S-Met, Amersham, Arlington Heights, Ill.) at 14 hours to 18 hours post-infection according to a protocol known to those of ordinary skill in the art. The cell monolayers were lysed by RIPA buffer and the polypeptides were immunoprecipitated with either polyclonal antiserum raised in goat against detergent disrupted RSV A2 virus (FIG. 7, lanes 1-4) or antiserum raised in mice against undisrupted B9320 virions (FIG. 7, lanes 5-8). The radio labeled immunoprecipitated polypeptides were electrophorsed on 10% polyacrylamide gels containing 0.1% SDS and detected by autoradiography. Anti-RSV A2 serum immunoprecipitated the major polypeptides of the RSV A2 strain, whereas anti-B9320 serum mainly reacted with RSV B9320 G protein and the conserved F protein of both A and B subgroups. As shown in FIG. 7, a protein which is identical to the A2-G protein (lane 3), was immunoprecipitated from the rRSVA2(B-G) infected cells (lane 4) by using an antiserum against RSV A2. The G protein of RSV B9320 strain was not recognized by the anti-A2 antiserum. A protein species, smaller than A2-G protein, was immunoprecipitated from both B9320 (lane 6) and rRSVA2(B-G)(lane 9) infected cells using the antiserum raised in mice against B9320 virions. This polypeptide was not present in the uninfected and RSV A2 infected cells and likely is to represent the G protein specific to the RSV B 9320 strain. Amino acid sequence comparison of both A2 and B9320 RSV G proteins indicated that two additional potential N-glycosylation sites (N-X-S/t) are present in the RSV A2G protein, which may contribute to slower migration of the A2 G protein under the conditions used. The F protein of RSV B9320 also migrated slightly faster than RSV A2 F protein. The P and M proteins also showed mobility differences between the two virus subtypes. The identity of the polypeptide near the top of the protein gel present in FSV B9320 and rRSVA2(B-G) infected cells is not known. Antisera raised in mice ot RSV B9320 virions poorly recognized the N, P and M proteins are compared to the goat antiserum raised against the RSV A2 strain. The data described above clearly indicate that chimeric rRSV A2(B-G) expresses both the RSV A2 and B9320 specific G proteins.

8.2.1 Replication of Recombinant RSV in Tissue Culture

Recombinant RS viruses were plaque purified three times and amplified in Hep-2 cells. Plaque assays were performed in Hep-2 cells in 12-well plates using an overlay of 1% methylcellulose and 1×L15 medium containing 2% fetal bovine serum (FBS). After incubation at 35° C. for 6 days, the monolayers were fixed with methanol and plaques were identified by immunostaining. Plaque size and morphology of rRSV was very similar to that of wild-type A2 RSV (FIG. 8). However, the plaques formed by rRSVC4G were smaller than rRSV and wild-type A2 virus. The only genetic difference between rRSV and rRSVC4 was a single nucleotide substitution in the RSV leader region. Therefore, the smaller plaque size of rRSV A2(B-G) was not distinguishable from that of rRSVC4G.

The growth curves of rRSV, rRSVC4G and rRSV A2 (B-G) were compared to that of the biologically derived wild-type A2 virus. Hep-2 cells were grown in T25 culture flasks and infected with rRSV, rRSVC4G, rRSVA2 (B-G), or wild-type RSV A2 strain at a moi of 0.5. After 1 hour adsorption at 37° C., the cells were washed three times with MEM containing 2% FBS and incubated at 37° C. in 5% $CO_2$. At 4 hour intervals post-infection, 250 µl of the culture supernatant was collected, and stored at −70° C. until virus titration. Each aliquot taken was replaced with an equal amount of fresh medium. The titer of each virus was determined by plaque assay on Hep-2 cells and visualized by immunostaining (vide supra). As shown in FIG. 9, the growth kinetics of rRSV is very similar to that of wild-type A2 virus. Maximum virus titer for all the viruses were achieved between 48 hr to 72 hr. The virus titer of rRSVC4G was about 2.4-fold (at 48 hr) and 6.6-fold (at 72 hr) lower than rRSV and wild-type A2 RSV. The poor growth of rRSVC4G may also be due to the single nucleotide change in the leader region. The chimeric rRSV A2(B-G) showed slower kinetics and lower peak titer (FIG. 9).

9. EXAMPLE

Generation of RSV L Gene Mutants

The strategy for generating L gene mutants is to introduce defined mutations or random mutations into the RSV L gene. The functionality of the L gene cDNA mutants can be screened in vitro by a minigenome replication system. The recovered L gene mutants are then further analyzed in vitro and in vivo.

9.1 Mutagenesis Strategies

9.1.1 Scanning Mutagenesis to Change the Clustered Charged Amino Acids to Alanine This mutagenesis strategy has been shown to be particularly effective in systematically targeting functional domains exposed on protein surfaces. The rationale is that clusters of charged residues generally do not lie buried in the protein structure. Making conservative substitutions of these charged residues with alanines will therefore remove the charges without grossly changing the structure of the protein. Disruption of charged clusters may interfere with the interaction of RSV L protein with other proteins and make its activity thermosensitive, thereby yielding temperature-sensitive mutants.

A cluster was originally defined arbitrarily as a stretch of 5 amino acids in which two or more residues are charged residues. For scanning mutagenesis, all the charged residues in the clusters can be changed to alanines by site directed mutagenesis. Because of the large size of the RSV L gene, there are many clustered charged residues in the L protein. Therefore, only contiguous charged residues of 3 to 5 amino acids throughout the entire L gene were targeted (FIG. 10). The RSV L protein contains 2 clusters of five contiguous charged residues, 2 clusters of four contiguous charged residues and 17 clusters of three contiguous charge residues. Two to four of the charged residues in each cluster were substituted with alanines.

The first step of the invention was to introduce the changes into pCITE-L which contains the entire RSV L-gene, using a QuikChange site-directed mutagenesis kit (Stratagene). The introduced mutations were then confirmed by sequence analysis.

9.1.2. Cysteine Scanning Mutagenesis

Cysteines are good targets for mutagenesis as they are frequently involved in intramolecular and intermolecular bond formations. By changing cysteines to glycines or alanines, the stability and function of a protein may be altered because of disruption of its tertiary structure. Thirty-nine cysteine residues are present in the RSV L protein (FIG. 11). Comparison of the RSV L protein with other members of paramyxoviruses indicates that some of the cysteine residues are conserved.

Five conserved cysteine residues were changed to either valine (conservative change) or to aspartic acids (nonconservative change) using a QuikChange site-directed mutagenesis kit (Stratagene) degenerate mutagenic oligonucleotides. It will be apparent to one skilled in the art that the sequence of the mutagenic oligonucleotides is determined by the protein sequence desired. The introduced mutations were confirmed by sequence analysis.

9.1.3. Random Mutagenesis

Random mutagenesis may change any residue, not simply charged residues or cysteines. Because of the size of the RSV L gene, several L gene cDNA fragments were mutagenized by PCR mutagenesis. This was accomplished by PCR using exo Pfu polymerase obtained from Strategene. Mutagenized PCR fragments were then cloned into a pCITE-L vector. Sequencing analysis of 20 mutagenized cDNA fragments indicated that 80%-90% mutation rates were achieved. The functionality of these mutants was then screened by a minigenome replication system. Any mutants showing altered polymerase function were then further cloned into the full-length RSV cDNA clone and virus recovered from transfected cells.

9.2. Functional Analysis of RSV L Protein Mutants by Minigenome Replication System The functionality of the L-genes mutants were tested by their ability to replicate a RSV minigenome containing a CAT gene in its antisense and flanked by RSV leader and trailer sequences. Hep-2 cells were infected with MVA vaccinia recombinants expressing T7 RNA polymerase. After one hour, the cells were transfected with plasmids expressing mutated L protein together with plasmids expressing N protein and P protein, and pRSV/CAT plasmid containing CAT gene (minigenome). CAT gene expression from the transfected cells was determined by a CAT ELISA assay (Boehringer Mannheim) according to the manufacturer's instruction. The amount of CAT activity produced by the L gene mutant was then compared to that of wild-type L protein.

9.3. Recovery of Mutant Recombinant RSV

To recover or rescue mutant recombinant RSV, mutations in the L-gene were engineered into plasmids encoding the entire RSV genome in the positive sense (antigenome). The L gene cDNA restriction fragments (BamH I and Not I) containing mutations in the L-gene were removed from pCITE vector and cloned into the full-length RSV cDNA clone. The cDNA clones were sequenced to confirm that each contained the introduced mutations.

Each RSV L gene mutant virus was rescued by co-transfection of the following plasmids into subconfluent Hep-2 cells grown in six-well plates. Prior to transfection, the Hep-2 cells were infected with MVA, a recombinant vaccinia virus which expresses T7 RNA polymerase. One hour later, cells were transfected with the following plasmids:
  pCITE-N: encoding wild-type RSV N gene, 0.4 µg
  pCITE-P: encoding wild-type RSV P gene, 0.4 µg
  pCITE-Lmutant: encoding mutant RSV L gene, 0.2 µg
  pRSVL mutant: full-length genomic RSV of the positive sense (antigenome) containing the same L-gene mutations as PCITE-L mutant, 0.6 µg DNA was introduced into cells by lipofecTACE (Life Technologies) in OPTI-MEM. After five hours or overnight transfection, the transfection medium was removed and replaced with 2% MEM. Following incubation at 35° C. for three days, the media supernatants from the transfected cells were used to infect Vero cells. The virus was recovered from the infected Vero cells and the introduced mutations in the recovered recombinant viruses confirmed by sequencing of the RT/PCR DNA derived from viral RNA.

Examples of the L gene mutants obtained by charged to alanine scanning mutagenesis are shown in the Table II. Mutants were assayed by determining the expression of CAT by pRSV/CAT minigenome following co-transfection of plasmids expressing N, P and either wild-type or mutant L. Cells were harvested and lysed 40 hours post-transfection after incubation at 33° C. or 39° C. The CAT activity was monitored by CAT ELISA assay (Boehringer Mannheim). Each sample represents the average of duplicate transfections. The amount of CAT produced for each sample was determined from a linear standard curve.

From the above preliminary studies, different types of mutations have been found.

9.3.1. Detrimental Mutations

Seven L protein mutants displayed a greater than 99% reduction in the amount of CAT produced compared to that of wild-type L protein. These mutations drastically reduced the activity of the RSV polymerase and are not expected to be viable.

9.3.2. Intermediate Mutations

Several L mutants showed an intermediate level of CAT production which ranged from 1% to 50% of that wild-type L protein. A subset of these mutants were introduced into virus and found to be viable. Preliminary data indicated that mutant A2 showed 10- to 20-fold reduction in virus titer when grown at 40° C. compared 33° C. Mutant A25 exhibited a smaller plaque formation phenotype when grown at both 33° C. and 39° C. This mutant also had a 10-fold reduction in virus titer at 40° C. compared to 33° C.

9.3.3. Mutants with L Protein Function Similar or Higher than Wild Type L Protein Some L gene mutants produced CAT gene expression levels similar to or greater than the wild-type L protein in vitro and the recovered virus mutants have phenotypes indistinguishable from wild-type viruses in tissue culture.

Once mutations in L that confer temperature sensitivity and attenuation have been identified, the mutations will be combined to rest for the cumulative effect of multiple temperature-sensitivity markers. The L mutants bearing more than one temperature sensitive marker are expected to have lower permissive temperature and to be genetically more stable than single-marker mutants.

The generated L gene mutants may also be combined with mutations present in other RSV genes and/or with non-essential RSV gene deletion mutants (e.g., SH and M2-2 deletion). This will enable the selection of safe, stable and effective live attenuated RSV vaccine candidates.

10. Generation of Human Respiratory Syncytial Virus Vaccine (RSV) Candidate by Deleting the Viral SH and M2ORF2 Genes

10.1. M2-2 Deletion Mutant

To delete M2-2 genes, two Hind III restriction enzyme sites were introduced at RSV nucleotides 8196 and 8430, respectively, in a cDNA subclone pET(S/B) which contained an RSV restriction fragment from 4478 to 8505. The RSV restriction fragment had been previously prepared by Quikchange site-directed mutagenesis (Strategene, Lo Jolla, Calif.). Digestion of pET (S/B) with Hind III restriction enzyme removed a 234 nucleotide sequence which contained the majority of the M2-2 open reading frame. The nucleotides encoding the first 13 amino acids at the N-terminus of the M2-2 gene product were not removed because this sequence overlaps M2-1. The cDNA fragment which contained M2-2 gene deletion was digested with SacI and BamHI and cloned back into a full-length RSV cDNA clone, designated pRSVΔM2-2

Infectious RSV with this M2-2 deletion was generated by transfecting pRSVΔM2-2 plasmid into MVA-infected Hep-2 cells expressing N, P and L genes. Briefly, pRSVΔM2-2 was transfected, together with plasmids encoding proteins N, P and L, into Hep-2 cells which had been infected with a recombinant vaccinia virus (MVA) expressing the T7 RNA polymerase. Transfection and recovery of recombinant RSV was performed as follows. Hep-2 cells were split five hours or a day before the transfection in six-well dishes. Monolayers of Hep-2 cells at 70%-80% confluence were infected with MVA at a multiplicity of infection (moi) of 5 and incubated at 35° C. for 60 min. The cells were then washed once with OPTI-MEM (Life Technologies, Gaithersburg, Md.). Each dish was replaced with 1 ml of OPTI-MEM and 0.2 ml transfection medium was added. The transfection medium was prepared by mixing 0.5-0.6 μg of RSV antigenome, 0.4 μg of N plasmid, 0.4 μg of P plasmid, and 0.2 μg of L plasmid in a final volume of 0.1 ml OPTI-MEM medium. This was combined with 0.1 ml of OPTI-MEM containing 10 μl lipofecTACE (Life Technologies). After a 15 minute incubation at room temperature, the DNA/lipofecTACE mixture was added to the cells. The medium was replaced one day later with MEM containing 2% FBS. Cultures were further incubated at 35° C. for 3 days and the supernatants harvested. Three days post-transfection, 0.3-0.4 ml culture supernatants were passaged onto fresh Hep-2 cells and incubated with MEM containing 2% FBS. After incubation for six days, the supernatant was harvested and the cells were fixed and stained by an indirect horseradish peroxidase method using goat anti-RSV antibody (Biogenesis) followed by a rabbit anti-goat antibody linked to horseradish peroxidase. The virus infected cells were then detected by addition of substrate chromogen (DAKO) according to the manufacturer's instructions. Recombinant RSV which contained M2-2 gene deletion was recovered from the transfected cells. Identification of rRSVΔM2-2 was performed by RT/PCR using primers flanking the deleted region. As shown in FIG. 12A, a cDNA fragment which is 234 nucleotides shorter than the wild-type RSV was detected in rRSVΔM2-2 infected cells. No cDNA was detected in the RT/PCR reaction which did not contain reverse transcriptase in the RT reaction. This indicated that the DNA product was derived from viral RNA and not from contamination. The properties of the M2-2 deletion RSV are currently being evaluated.

10.2. SH Deletion Mutant

To delete the SH gene from RSV, a Sac I restriction enzyme site was introduced at the gene start signal of SH gene at position of nt 4220. A unique SacI site also exists at the C-terminus of the SH gene. Site-directed mutagenesis was performed in subclone pET(A/S), which contains an AvrII (2129) SacI (4478) restriction fragment. Digestion of pET(A/S) mutant with SacI removed a 258 nucleotide fragment of the SH gene. Digestion of the pET(A/S) subclone containing the SH deletion was digested with Avr II and Sac I and the resulting restriction fragment was then cloned into a full-length RSV cDNA clone. The full-length cDNA clone containing the SH deletion was designated pRSVΔSH.

Generation of the pRSVΔSH mutant was performed as described above (see 10.1). SH-minus RSV (rRSVΔSH) was recovered from MVA-infected cells that had been co-transfected with pRSVΔSH together with N, P and L expression plasmids. Identification of the recovered rRSVΔSH was performed by RT/PCR using a pair of primers which flanked the SH gene. As shown in FIG. 12A, a cDNA band which is about 258 nucleotides shorter than the wild-type virus was detected in the rRSVΔSH infected cells. No DNA was detected in the RT/PCR reaction which did not have reverse transcriptase in the RT reaction. This indicated that the PCR DNA was derived from viral RNA and was not artifact, and that the virus obtained was truly SH-minus RSV.

10.3. Generation of Both SH and M2-2 Deletion Mutant

Both SH and M2-2 genes were deleted from the full-length RSV cDNA construct by cDNA subcloning. A Sac I to Bam HI fragment containing M2-2 deletion removed from cDNA subclone pET(S/B)ΔM2-2RSV was cloned into pRSVΔSH cDNA clone. The double gene deletion plasmid pRSVΔSHΔM2-2 was confirmed by restriction enzyme mapping. As shown in FIG. 12B, the SH/M2-2 double deletion mutant is shorter than the wild-type pRSV cDNA.

Recovery of infectious RSV containing both the SH and M2-2 deletion was performed as described earlier. Infectious virus with both SH and M2-2 deleted was obtained from transfected Hep-2 cells.

TABLE II

CAT Expression levels of Mutant RSV L-gene

| Mut. | Conc. of CAT (ng/mL) 33° C. | Conc. of CAT (ng/mL) 39° C. | Charge Cluster | Charge to Alanine Change | Rescued Virus |
|---|---|---|---|---|---|
| A33 | 0.246 | Bkg | 5 | 135E, 136K | No |
| A73 | 3.700 | 0.318 | 3 | 146D, 147E, 148D | Yes |
| A171 | 3.020 | Bkg | 3 | 157K, 158D | Yes |
| A81 | 1.000 | 0.280 | 3 | 255H, 256K | Yes |
| A185 | Bkg | Bkg | 3 | 348E, 349E | No |
| A91 | Bkg | Bkg | 3 | 353R, 355R | No |
| A101 | Bkg | Bkg | 3 | 435D, 436E, 437R | No |
| A192 | 1.960 | Bkg | 3 | 510E, 511R | Yes |
| A11 | 0.452 | Bkg | 1 | 520R | Yes |
| A111 | 2.320 | 0.267 | 4 | 568H, 569E | Yes |
| A121 | 0.772 | Bkg | 2 | 587L, 588R | No |
| A133 | Bkg | Bkg | 4 | 620E, 621R | No |
| A141 | 2.800 | Bkg | 3 | 1025K, 1026D | Yes |
| A25 | 0.169 | Bkg | 3 | 1033D, 1034D | Yes |
| A45 | 5.640 | 0.478 | 5 | 1187D, 1188K | Yes |
| A153 | 4.080 | 0.254 | 5 | 1187D, 1188K, 1189R, 1190E | Yes |
| A162 | 10.680 | Bkg | 3 | 1208E, 1209R | No |
| A201 | Bkg | Bkg | 3 | 1269E, 1270K | No |
| A211 | 2.440 | 0.047 | 3 | 1306D, 1307E | Yes |
| A221 | 0.321 | Bkg | 3 | 1378D, 1379E | No |
| A231 | Bkg | Bkg | 3 | 1515E, 1516K | No |
| A241 | 1.800 | 0.308 | 3 | 1662H, 1663K | Yes |
| A57 | 5.660 | 0.706 | 3 | 1725D, 1726K | Yes |
| A65 | 3.560 | 0.168 | 2 | 1957R, 1958K | Yes |
| A251 | 0.030 | Bkg. | 3 | 2043D, 2044K | Yes |
| A261 | Bkg | Bkg | 3 | 2102K, 2103H | No |
| AD11 | 2.800 | 0.456 | 5 and 3 | 1187D, 1188K, 1725D, 1726K | No |
| AD21 | 2.640 | 0.226 | 5 and 2 | 1187D, 1188K, 1957R, 1958K | No |
| AD31 | 1.280 | 0.192 | 3 and 2 | 1725D, 1726K, 1957R, 1958K | No |
| F1 | Bkg | Bkg | — | 521 F to L | Yes |
| F13 | 0.13 | Bkg | — | 521 F to L | Yes |
| Lwt | 3.16 | — | — | no amino acid changes | Yes |

The present invention is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, the disclosures of which are incorporated by reference in their entireties.

```

What is claimed is:

1. An isolated infectious Respiratory Syncytial Viral (RSV) particle which comprises an RSV antigenome or genome comprising (i) at least one functional deletion in the M2-2 open reading frame, and (ii) encoding one or more amino acid exchanges in the L protein at the following positions 135, 136, 146, 147, 148, 157, 158, 255, 256, 510, 511, 520, 568, 569, 587, 588, 1025, 1026, 1033, 1034, 1187, 1188, 1189, 1190, 1208, 1209, 1306, 1307, 1378, 1379, 1663, 1725, 1726, 1957, 1958, 2043, and 2044.

2. The isolated RSV particle of claim 1, wherein the particle comprises antigenic polypeptides of both RSV-A and RSV-B.

3. The isolated RSV particle of claim 2 that further comprises a deletion in SH-ORF.

4. The isolated RSV particle of claim 1, wherein the particle comprises G and F polypeptides of both RSV A and RSV B.

5. The isolated RSV particle of claim 4 that further comprises a deletion in SH-ORF.

6. An immunogenic composition comprising the viral particle of claim 1, 2, 3, 4 or 5.

7. The isolated RSV particle of claim 1, 2, 3, or 4, wherein the one or more amino acid exchanges in the L protein is at a position or positions selected from:
   520; or
   146, 147, and 148; or
   157 and 158; or
   255 and 256; or
   510 and 511; or
   568 and 569; or
   1025 and 1026; or
   1033 and 1034; or
   1187 and 1188; or
   1187, 1188, 1189 and 1190; or
   1306 and 1307; or
   1662 and 1663; or
   1725 and 1726; or
   1957 and 1958; or
   2043 and 2044.

8. The isolated RSV particle of claim 7, wherein the amino acid exchange is to alanine.

* * * * *

                        SEQUENCE LISTING

<160> NUMBER OF SEQ ID NOS: 50

<210> SEQ ID NO 1
<211> LENGTH: 46
<212> TYPE: DNA
<213> ORGANISM: Artificial Sequence
<220> FEATURE:
<223> OTHER INFORMATION: Oligonucleotide

<400> SEQUENCE: 1
cgacgcatat tacgcgaaaa aatgcgtaca acaaacttgc ataaac              46

<210> SEQ ID NO 2
<211> LENGTH: 50
<212> TYPE: DNA
<213> ORGANISM: Artificial Sequence
<220> FEATURE:
<223> OTHER INFORMATION: Oligonucleotide

<400> SEQUENCE: 2
caaaaaaatg gggcaaataa gaatttgata agtaccactt aaatttaact          50

<210> SEQ ID NO 3
<211> LENGTH: 24
<212> TYPE: DNA
<213> ORGANISM: Artificial Sequence
<220> FEATURE:
<223> OTHER INFORMATION: Oligonucleotide

<400> SEQUENCE: 3
ctagagttaa atttaagtgg tact                                      24

<210> SEQ ID NO 4
<211> LENGTH: 50
<212> TYPE: DNA
<213> ORGANISM: Artificial Sequence
<220> FEATURE:
<223> OTHER INFORMATION: Oligonucleotide

<400> SEQUENCE: 4
tatcaaattc ttatttgccc cattttttg gtttatgcaa gtttgttgta           50

<210> SEQ ID NO 5
<211> LENGTH: 30
<212> TYPE: DNA
<213> ORGANISM: Artificial Sequence
<220> FEATURE:
<223> OTHER INFORMATION: Oligonucleotide

<400> SEQUENCE: 5
cgcatttttt cgcgtaatat gcgtcggtac                                30

<210> SEQ ID NO 6
<211> LENGTH: 50
<212> TYPE: DNA
<213> ORGANISM: Artificial Sequence
<220> FEATURE:
<223> OTHER INFORMATION: Oligonucleotide
```

```
<400> SEQUENCE: 6
gtattcaatt atagttatta aaaattaaaa atcatataat ttttttaaata          50

<210> SEQ ID NO 7
<211> LENGTH: 50
<212> TYPE: DNA
<213> ORGANISM: Artificial Sequence
<220> FEATURE:
<223> OTHER INFORMATION: Oligonucleotide

<400> SEQUENCE: 7 actttttagtg aactaatcct aaagttatca ttttaatctt ggaggaataa          50

<210> SEQ ID NO 8
<211> LENGTH: 50
<212> TYPE: DNA
<213> ORGANISM: Artificial Sequence
<220> FEATURE:
<223> OTHER INFORMATION: Oligonucleotide

<400> SEQUENCE: 8
atttaaaccc taatctaatt ggtttatatg tgtattaact aaattacgag           50

<210> SEQ ID NO 9
<211> LENGTH: 46
<212> TYPE: DNA
<213> ORGANISM: Artificial Sequence
<220> FEATURE:
<223> OTHER INFORMATION: Oligonucleotide

<400> SEQUENCE: 9
atattagttt ttgacacttt ttttctcgtt atagtgagtc gtatta              46

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide

<400> SEQUENCE: 10
agcttaatac gactcactat aacga                                     25

<210> SEQ ID NO 11
<211> LENGTH: 50
<212> TYPE: DNA
<213> ORGANISM: Artificial Sequence
<220> FEATURE:
<223> OTHER INFORMATION: Oligonucleotide

<400> SEQUENCE: 11
gaaaaaaagt gtcaaaaact aatatctcgt aatttagtta atacacatat          50

<210> SEQ ID NO 12
<211> LENGTH: 50
<212> TYPE: DNA
<213> ORGANISM: Artificial Sequence
<220> FEATURE:
<223> OTHER INFORMATION: Oligonucleotide

<400> SEQUENCE: 12
aaaccaatta gattagggtt taaatttatt cctccaagat taaaatgata          50

<210> SEQ ID NO 13
<211> LENGTH: 50
```

<212> TYPE: DNA
<213> ORGANISM: Artificial Sequence
<220> FEATURE:
<223> OTHER INFORMATION: Oligonucleotide

<400> SEQUENCE: 13
actttaggat tagttcacta aaagttattt aaaaaattat atgatttta              50

<210> SEQ ID NO 14
<211> LENGTH: 29
<212> TYPE: DNA
<213> ORGANISM: Artificial Sequence
<220> FEATURE:
<223> OTHER INFORMATION: Oligonucleotide

<400> SEQUENCE: 14
atttttaata actataattg aatactgca                                    29

<210> SEQ ID NO 15
<211> LENGTH: 17
<212> TYPE: DNA
<213> ORGANISM: Artificial Sequence
<220> FEATURE:
<223> OTHER INFORMATION: Primer

<400> SEQUENCE: 15
gtttaacacg tggtgag                                                 17

<210> SEQ ID NO 16
<211> LENGTH: 17
<212> TYPE: DNA
<213> ORGANISM: Artificial Sequence
<220> FEATURE:
<223> OTHER INFORMATION: Primer

<400> SEQUENCE: 16
acatataggc atgcacc                                                 17

<210> SEQ ID NO 17
<211> LENGTH: 17
<212> TYPE: DNA
<213> ORGANISM: Artificial Sequence
<220> FEATURE:
<223> OTHER INFORMATION: Primer

<400> SEQUENCE: 17
gcaaaatgga tcccatt                                                 17

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
tggttggtat accagtgt                                                18

<210> SEQ ID NO 19
<211> LENGTH: 18
<212> TYPE: DNA
<213> ORGANISM: Artificial Sequence
<220> FEATURE:
<223> OTHER INFORMATION: Primer

<400> SEQUENCE: 19

-continued taccaagagc tcgagtca                                          18

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
ggtggccggc atggtcccag c                                      21

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
tttaccatat gcgctaatgt                                        20

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
acgcgaaaaa atgcgtaca                                         19

<210> SEQ ID NO 23
<211> LENGTH: 18
<212> TYPE: DNA
<213> ORGANISM: Artificial Sequence
<220> FEATURE:
<223> OTHER INFORMATION: Primer

<400> SEQUENCE: 23
acgagaaaaa agtggcaa                                          18

<210> SEQ ID NO 24
<211> LENGTH: 17
<212> TYPE: DNA
<213> ORGANISM: Artificial Sequence
<220> FEATURE:
<223> OTHER INFORMATION: Primer

<400> SEQUENCE: 24
ctcaccacgt gttaaac                                           17

<210> SEQ ID NO 25
<211> LENGTH: 17
<212> TYPE: DNA
<213> ORGANISM: Artificial Sequence
<220> FEATURE:
<223> OTHER INFORMATION: Primer

<400> SEQUENCE: 25
ggtgcatgcc tatatgt                                           17

<210> SEQ ID NO 26
<211> LENGTH: 19
<212> TYPE: DNA
<213> ORGANISM: Artificial Sequence

```
<220> FEATURE:
<223> OTHER INFORMATION: Primer

<400> SEQUENCE: 26
aatgggatcc attttgtcc                                                       19

<210> SEQ ID NO 27
<211> LENGTH: 19
<212> TYPE: DNA
<213> ORGANISM: Artificial Sequence
<220> FEATURE:
<223> OTHER INFORMATION: Primer

<400> SEQUENCE: 27
aacactggta taccaacca                                                       19

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
acattagcgc atatggtaaa                                                      20

<210> SEQ ID NO 29
<211> LENGTH: 2165
<212> TYPE: PRT
<213> ORGANISM: Virus

<400> SEQUENCE: 29
```

Met Asp Pro Ile Ile Asn Gly Asn Ser Ala Asn Val Tyr Leu Thr Asp
 1               5                  10                  15

Ser Tyr Leu Lys Gly Val Ile Ser Phe Ser Glu Cys Asn Ala Leu Gly
                20                  25                  30

Ser Tyr Ile Phe Asn Gly Pro Tyr Leu Lys Asn Asp Tyr Thr Asn Leu
            35                  40                  45

Ile Ser Arg Gln Asn Pro Leu Ile Glu His Met Asn Leu Lys Lys Leu
        50                  55                  60

Asn Ile Thr Gln Ser Leu Ile Ser Lys Tyr His Lys Gly Glu Ile Lys
65                  70                  75                  80

Leu Glu Glu Pro Thr Tyr Phe Gln Ser Leu Leu Met Thr Tyr Lys Ser
                85                  90                  95

Met Thr Ser Ser Glu Gln Ile Ala Thr Thr Asn Leu Leu Lys Lys Ile
                100                 105                 110

Ile Arg Arg Ala Ile Glu Ile Ser Asp Val Lys Val Tyr Ala Ile Leu
            115                 120                 125

Asn Lys Leu Gly Leu Lys Glu Lys Asp Lys Ile Lys Ser Asn Asn Gly
        130                 135                 140

Gln Asp Glu Asp Asn Ser Val Ile Thr Thr Ile Lys Asp Asp Ile
145                 150                 155                 160

Leu Ser Ala Val Lys Asp Asn Gln Ser His Leu Lys Ala Asp Lys Asn
                165                 170                 175

His Ser Thr Lys Gln Lys Asp Thr Ile Lys Thr Thr Leu Leu Lys Lys
                180                 185                 190

Leu Met Cys Ser Met Gln His Pro Pro Ser Trp Leu Ile His Trp Phe
            195                 200                 205

Asn Leu Tyr Thr Lys Leu Asn Asn Ile Leu Thr Gln Tyr Arg Ser Asn

-continued

```
            210                 215                 220
Glu Val Lys Asn His Gly Phe Thr Leu Ile Asp Asn Gln Thr Leu Ser
225                 230                 235                 240

Gly Phe Gln Phe Ile Leu Asn Gln Tyr Gly Cys Ile Val Tyr His Lys
            245                 250                 255

Glu Leu Lys Arg Ile Thr Val Thr Thr Tyr Asn Gln Phe Leu Thr Trp
            260                 265                 270

Lys Asp Ile Ser Leu Ser Arg Leu Asn Val Cys Leu Ile Thr Trp Ile
            275                 280                 285

Ser Asn Cys Leu Asn Thr Leu Asn Lys Ser Leu Gly Leu Arg Cys Gly
290                 295                 300

Phe Asn Asn Val Ile Leu Thr Gln Leu Phe Leu Tyr Gly Asp Cys Ile
305                 310                 315                 320

Leu Lys Leu Phe His Asn Glu Gly Phe Tyr Ile Ile Lys Glu Val Glu
            325                 330                 335

Gly Phe Ile Met Ser Leu Ile Leu Asn Ile Thr Glu Glu Asp Gln Phe
            340                 345                 350

Arg Lys Arg Phe Tyr Asn Ser Met Leu Asn Asn Ile Thr Asp Ala Ala
            355                 360                 365

Asn Lys Ala Gln Lys Asn Leu Leu Ser Arg Val Cys His Thr Leu Leu
            370                 375                 380

Asp Lys Thr Val Ser Asp Asn Ile Ile Asn Gly Arg Trp Ile Ile Leu
385                 390                 395                 400

Leu Ser Lys Phe Leu Lys Leu Ile Lys Leu Ala Gly Asp Asn Asn Leu
            405                 410                 415

Asn Asn Leu Ser Glu Leu Tyr Phe Leu Phe Arg Ile Phe Gly His Pro
            420                 425                 430

Met Val Asp Glu Arg Gln Ala Met Asp Ala Val Lys Ile Asn Cys Asn
            435                 440                 445

Glu Thr Lys Phe Tyr Leu Leu Ser Ser Leu Ser Met Leu Arg Gly Ala
            450                 455                 460

Phe Ile Tyr Arg Ile Ile Lys Gly Phe Val Asn Asn Tyr Asn Arg Trp
465                 470                 475                 480

Pro Thr Leu Arg Asn Ala Ile Val Leu Pro Leu Arg Trp Leu Thr Tyr
            485                 490                 495

Tyr Lys Leu Asn Thr Tyr Pro Ser Leu Leu Glu Leu Thr Glu Arg Asp
            500                 505                 510

Leu Ile Val Leu Ser Gly Leu Arg Phe Tyr Arg Glu Phe Arg Leu Pro
            515                 520                 525

Lys Lys Val Asp Leu Glu Met Ile Ile Asn Asp Lys Ala Ile Ser Pro
530                 535                 540

Pro Lys Asn Leu Ile Trp Thr Ser Phe Pro Arg Asn Tyr Met Pro Ser
545                 550                 555                 560

His Ile Gln Asn Tyr Ile Glu His Glu Lys Leu Lys Phe Ser Glu Ser
            565                 570                 575

Asp Lys Ser Arg Arg Val Leu Glu Tyr Tyr Leu Arg Asp Asn Lys Phe
            580                 585                 590

Asn Glu Cys Asp Leu Tyr Asn Cys Val Val Asn Gln Ser Tyr Leu Asn
            595                 600                 605

Asn Pro Asn His Val Val Ser Leu Thr Gly Lys Glu Arg Glu Leu Ser
            610                 615                 620

Val Gly Arg Met Phe Ala Met Gln Pro Gly Met Phe Arg Gln Val Gln
625                 630                 635                 640
```

-continued

Ile Leu Ala Glu Lys Met Ile Ala Glu Asn Ile Leu Gln Phe Phe Pro
                645                 650                 655

Glu Ser Leu Thr Arg Tyr Gly Asp Leu Glu Leu Gln Lys Ile Leu Glu
                660                 665                 670

Leu Lys Ala Gly Ile Ser Asn Lys Ser Asn Arg Tyr Asn Asp Asn Tyr
                675                 680                 685

Asn Asn Tyr Ile Ser Lys Cys Ser Ile Ile Thr Asp Leu Ser Lys Phe
            690                 695                 700

Asn Gln Ala Phe Arg Tyr Glu Thr Ser Cys Ile Cys Ser Asp Val Leu
705                 710                 715                 720

Asp Glu Leu His Gly Val Gln Ser Leu Phe Ser Trp Leu His Leu Thr
                    725                 730                 735

Ile Pro His Val Thr Ile Ile Cys Thr Tyr Arg His Ala Pro Pro Tyr
                740                 745                 750

Ile Gly Asp His Ile Val Asp Leu Asn Asn Val Asp Glu Gln Ser Gly
                755                 760                 765

Leu Tyr Arg Tyr His Met Gly Gly Ile Glu Gly Trp Cys Gln Lys Leu
                770                 775                 780

Trp Thr Ile Glu Ala Ile Ser Leu Leu Asp Leu Ile Ser Leu Lys Gly
785                 790                 795                 800

Lys Phe Ser Ile Thr Ala Leu Ile Asn Gly Asp Asn Gln Ser Ile Asp
                    805                 810                 815

Ile Ser Lys Pro Ile Arg Leu Met Glu Gly Gln Thr His Ala Gln Ala
                820                 825                 830

Asp Tyr Leu Leu Ala Leu Asn Ser Leu Lys Leu Leu Tyr Lys Glu Tyr
                835                 840                 845

Ala Gly Ile Gly His Lys Leu Lys Gly Thr Glu Thr Tyr Ile Ser Arg
                850                 855                 860

Asp Met Gln Phe Met Ser Lys Thr Ile Gln His Asn Gly Val Tyr Tyr
865                 870                 875                 880

Pro Ala Ser Ile Lys Lys Val Leu Arg Val Gly Pro Trp Ile Asn Thr
                    885                 890                 895

Ile Leu Asp Asp Phe Lys Val Ser Leu Glu Ser Ile Gly Ser Leu Thr
                900                 905                 910

Gln Glu Leu Glu Tyr Arg Gly Glu Ser Leu Leu Cys Ser Leu Ile Phe
                915                 920                 925

Arg Asn Val Trp Leu Tyr Asn Gln Ile Ala Leu Gln Leu Lys Asn His
930                 935                 940

Ala Leu Cys Asn Asn Lys Leu Tyr Leu Asp Ile Leu Lys Val Leu Lys
945                 950                 955                 960

His Leu Lys Thr Phe Phe Asn Leu Asp Asn Ile Asp Thr Ala Leu Thr
                    965                 970                 975

Leu Tyr Met Asn Leu Pro Met Leu Phe Gly Gly Gly Asp Pro Asn Leu
                980                 985                 990

Leu Tyr Arg Ser Phe Tyr Arg Arg Thr Pro Asp Phe Leu Thr Glu Ala
                995                 1000                1005

Ile Val His Ser Val Phe Ile Leu Ser Tyr Tyr Thr Asn His Asp Leu
                1010                1015                1020

Lys Asp Lys Leu Gln Asp Leu Ser Asp Asp Arg Leu Asn Lys Phe Leu
1025                1030                1035                1040

Thr Cys Ile Ile Thr Phe Asp Lys Asn Pro Asn Ala Glu Phe Val Thr
                    1045                1050                1055

-continued

```
Leu Met Arg Asp Pro Gln Ala Leu Gly Ser Glu Arg Gln Ala Lys Ile
            1060                1065                1070

Thr Ser Glu Ile Asn Arg Leu Ala Val Thr Glu Val Leu Ser Thr Ala
        1075                1080                1085

Pro Asn Lys Ile Phe Ser Lys Ser Ala Gln His Tyr Thr Thr Thr Glu
    1090                1095                1100

Ile Asp Leu Asn Asp Ile Met Gln Asn Ile Glu Pro Thr Tyr Pro His
1105                1110                1115                1120

Gly Leu Arg Val Val Tyr Glu Ser Leu Pro Phe Tyr Lys Ala Glu Lys
            1125                1130                1135

Ile Val Asn Leu Ile Ser Gly Thr Lys Ser Ile Thr Asn Ile Leu Glu
        1140                1145                1150

Lys Thr Ser Ala Ile Asp Leu Thr Asp Ile Asp Arg Ala Thr Glu Met
    1155                1160                1165

Met Arg Lys Asn Ile Thr Leu Leu Ile Arg Ile Leu Pro Leu Asp Cys
1170                1175                1180

Asn Arg Asp Lys Arg Glu Ile Leu Ser Met Glu Asn Leu Ser Ile Thr
1185                1190                1195                1200

Glu Leu Ser Lys Tyr Val Arg Glu Arg Ser Trp Ser Leu Ser Asn Ile
            1205                1210                1215

Val Gly Val Thr Ser Pro Ser Ile Met Tyr Thr Met Asp Ile Lys Tyr
        1220                1225                1230

Thr Thr Ser Thr Ile Ser Ser Gly Ile Ile Ile Glu Lys Tyr Asn Val
    1235                1240                1245

Asn Ser Leu Thr Arg Gly Glu Arg Gly Pro Thr Lys Pro Trp Val Gly
1250                1255                1260

Ser Ser Thr Gln Glu Lys Lys Thr Met Pro Val Tyr Asn Arg Gln Val
1265                1270                1275                1280

Leu Thr Lys Lys Gln Arg Asp Gln Ile Asp Leu Leu Ala Lys Leu Asp
            1285                1290                1295

Trp Val Tyr Ala Ser Ile Asp Asn Lys Asp Glu Phe Met Glu Glu Leu
        1300                1305                1310

Ser Ile Gly Thr Leu Gly Leu Thr Tyr Glu Lys Ala Lys Lys Leu Phe
    1315                1320                1325

Pro Gln Tyr Leu Ser Val Asn Tyr Leu His Arg Leu Thr Val Ser Ser
1330                1335                1340

Arg Pro Cys Glu Phe Pro Ala Ser Ile Pro Ala Tyr Arg Thr Thr Asn
1345                1350                1355                1360

Tyr His Phe Asp Thr Ser Pro Ile Asn Arg Ile Leu Thr Glu Lys Tyr
            1365                1370                1375

Gly Asp Glu Asp Ile Asp Ile Val Phe Gln Asn Cys Ile Ser Phe Gly
        1380                1385                1390

Leu Ser Leu Met Ser Val Val Glu Gln Phe Thr Asn Val Cys Pro Asn
    1395                1400                1405

Arg Ile Ile Leu Ile Pro Lys Leu Asn Glu Ile His Leu Met Lys Pro
1410                1415                1420

Pro Ile Phe Thr Gly Asp Val Asp Ile His Lys Leu Lys Gln Val Ile
1425                1430                1435                1440

Gln Lys Gln His Met Phe Leu Pro Asp Lys Ile Ser Leu Thr Gln Tyr
            1445                1450                1455

Val Glu Leu Phe Leu Ser Asn Lys Thr Leu Lys Ser Gly Ser His Val
        1460                1465                1470

Asn Ser Asn Leu Ile Leu Ala His Lys Ile Ser Asp Tyr Phe His Asn
```

-continued

```
                1475                1480                1485
Thr Tyr Ile Leu Ser Thr Asn Leu Ala Gly His Trp Ile Leu Ile Ile
    1490                1495                1500
Gln Leu Met Lys Asp Ser Lys Gly Ile Phe Glu Lys Asp Trp Gly Glu
1505                1510                1515                1520
Gly Tyr Ile Thr Asp His Met Phe Ile Asn Leu Lys Val Phe Phe Asn
            1525                1530                1535
Ala Tyr Lys Thr Tyr Leu Leu Cys Phe His Lys Gly Tyr Gly Lys Ala
        1540                1545                1550
Lys Leu Glu Cys Asp Met Asn Thr Ser Asp Leu Leu Cys Val Leu Glu
1555                1560                1565
Leu Ile Asp Ser Ser Tyr Trp Lys Ser Met Ser Lys Val Phe Leu Glu
    1570                1575                1580
Gln Lys Val Ile Lys Tyr Ile Leu Ser Gln Asp Ala Ser Leu His Arg
1585                1590                1595                1600
Val Lys Gly Cys His Ser Phe Lys Leu Trp Phe Leu Lys Arg Leu Asn
            1605                1610                1615
Val Ala Glu Phe Thr Val Cys Pro Trp Val Val Asn Ile Asp Tyr His
        1620                1625                1630
Pro Thr His Met Lys Ala Ile Leu Thr Tyr Ile Asp Leu Val Arg Met
        1635                1640                1645
Gly Leu Ile Asn Ile Asp Arg Ile His Ile Lys Asn Lys His Lys Phe
    1650                1655                1660
Asn Asp Glu Phe Tyr Thr Ser Asn Leu Phe Tyr Ile Asn Tyr Asn Phe
1665                1670                1675                1680
Ser Asp Asn Thr His Leu Leu Thr Lys His Ile Arg Ile Ala Asn Ser
            1685                1690                1695
Glu Leu Glu Asn Asn Tyr Asn Lys Leu Tyr His Pro Thr Pro Glu Thr
        1700                1705                1710
Leu Glu Asn Ile Leu Ala Asn Pro Ile Lys Ser Asn Asp Lys Lys Thr
        1715                1720                1725
Leu Asn Asp Tyr Cys Ile Gly Lys Asn Val Asp Ser Ile Met Leu Pro
    1730                1735                1740
Leu Leu Ser Asn Lys Lys Leu Ile Lys Ser Ser Ala Met Ile Arg Thr
1745                1750                1755                1760
Asn Tyr Ser Lys Gln Asp Leu Tyr Asn Leu Phe Pro Met Val Val Ile
            1765                1770                1775
Asp Arg Ile Ile Asp His Ser Gly Asn Thr Ala Lys Ser Asn Gln Leu
        1780                1785                1790
Tyr Thr Thr Thr Ser His Gln Ile Ser Leu Val His Asn Ser Thr Ser
        1795                1800                1805
Leu Tyr Cys Met Leu Pro Trp His His Ile Asn Arg Phe Asn Phe Val
    1810                1815                1820
Phe Ser Ser Thr Gly Cys Lys Ile Ser Ile Glu Tyr Ile Leu Lys Asp
1825                1830                1835                1840
Leu Lys Ile Lys Asp Pro Asn Cys Ile Ala Phe Ile Gly Glu Gly Ala
            1845                1850                1855
Gly Asn Leu Leu Leu Arg Thr Val Val Glu Leu His Pro Asp Ile Arg
        1860                1865                1870
Tyr Ile Tyr Arg Ser Leu Lys Asp Cys Asn Asp His Ser Leu Pro Ile
        1875                1880                1885
Glu Phe Leu Arg Leu Tyr Asn Gly His Ile Asn Ile Asp Tyr Gly Glu
    1890                1895                1900
```

```
Asn Leu Thr Ile Pro Ala Thr Asp Ala Thr Asn Asn Ile His Trp Ser
1905                1910                1915                1920

Tyr Leu His Ile Lys Phe Ala Glu Pro Ile Ser Leu Phe Val Cys Asp
            1925                1930                1935

Ala Glu Leu Ser Val Thr Val Asn Trp Ser Lys Ile Ile Glu Trp
        1940                1945                1950

Ser Lys His Val Arg Lys Cys Lys Tyr Cys Ser Ser Val Asn Lys Cys
        1955                1960                1965

Met Leu Ile Val Lys Tyr His Ala Gln Asp Asp Ile Asp Phe Lys Leu
    1970                1975                1980

Asp Asn Ile Thr Ile Leu Lys Thr Tyr Val Cys Leu Gly Ser Lys Leu
1985                1990                1995                2000

Lys Gly Ser Glu Val Tyr Leu Val Leu Thr Ile Gly Pro Ala Asn Ile
            2005                2010                2015

Phe Pro Val Phe Asn Val Val Gln Asn Ala Lys Leu Ile Leu Ser Arg
        2020                2025                2030

Thr Lys Asn Phe Ile Met Pro Lys Lys Ala Asp Lys Glu Ser Ile Asp
        2035                2040                2045

Ala Asn Ile Lys Ser Leu Ile Pro Phe Leu Cys Tyr Pro Ile Thr Lys
    2050                2055                2060

Lys Gly Ile Asn Thr Ala Leu Ser Lys Leu Lys Ser Val Val Ser Gly
2065                2070                2075                2080

Asp Ile Leu Ser Tyr Ser Ile Ala Gly Arg Asn Glu Val Phe Ser Asn
            2085                2090                2095

Lys Leu Ile Asn His Lys His Met Asn Ile Leu Lys Trp Phe Asn His
        2100                2105                2110

Val Leu Asn Phe Arg Ser Thr Glu Leu Asn Tyr Asn His Leu Tyr Met
        2115                2120                2125

Val Glu Ser Thr Tyr Pro Tyr Leu Ser Glu Leu Leu Asn Ser Leu Thr
    2130                2135                2140

Thr Asn Glu Leu Lys Lys Leu Ile Lys Ile Thr Gly Ser Leu Leu Tyr
2145                2150                2155                2160

Asn Phe His Asn Glu
            2165

<210> SEQ ID NO 30
<211> LENGTH: 2165
<212> TYPE: PRT
<213> ORGANISM: Virus

<400> SEQUENCE: 30

Met Asp Pro Ile Ile Asn Gly Asn Ser Ala Asn Val Tyr Leu Thr Asp
 1               5                  10                  15

Ser Tyr Leu Lys Gly Val Ile Ser Phe Ser Glu Cys Asn Ala Leu Gly
            20                  25                  30

Ser Tyr Ile Phe Asn Gly Pro Tyr Leu Lys Asn Asp Tyr Thr Asn Leu
        35                  40                  45

Ile Ser Arg Gln Asn Pro Leu Ile Glu His Met Asn Leu Lys Lys Leu
    50                  55                  60

Asn Ile Thr Gln Ser Leu Ile Ser Lys Tyr His Lys Gly Glu Ile Lys
65                  70                  75                  80

Leu Glu Glu Pro Thr Tyr Phe Gln Ser Leu Leu Met Thr Tyr Lys Ser
            85                  90                  95

Met Thr Ser Ser Glu Gln Ile Ala Thr Thr Asn Leu Leu Lys Lys Ile
```

-continued

```
              100                 105                 110
Ile Arg Arg Ala Ile Glu Ile Ser Asp Val Lys Val Tyr Ala Ile Leu
        115                 120                 125
Asn Lys Leu Gly Leu Lys Glu Lys Asp Lys Ile Lys Ser Asn Asn Gly
        130                 135                 140
Gln Asp Glu Asp Asn Ser Val Ile Thr Thr Ile Ile Lys Asp Asp Ile
145                 150                 155                 160
Leu Ser Ala Val Lys Asp Asn Gln Ser His Leu Lys Ala Asp Lys Asn
                165                 170                 175
His Ser Thr Lys Gln Lys Asp Thr Ile Lys Thr Thr Leu Leu Lys Lys
                180                 185                 190
Leu Met Cys Ser Met Gln His Pro Pro Ser Trp Leu Ile His Trp Phe
            195                 200                 205
Asn Leu Tyr Thr Lys Leu Asn Asn Ile Leu Thr Gln Tyr Arg Ser Asn
        210                 215                 220
Glu Val Lys Asn His Gly Phe Thr Leu Ile Asp Asn Gln Thr Leu Ser
225                 230                 235                 240
Gly Phe Gln Phe Ile Leu Asn Gln Tyr Gly Cys Ile Val Tyr His Lys
                245                 250                 255
Glu Leu Lys Arg Ile Thr Val Thr Thr Tyr Asn Gln Phe Leu Thr Trp
            260                 265                 270
Lys Asp Ile Ser Leu Ser Arg Leu Asn Val Cys Leu Ile Thr Trp Ile
        275                 280                 285
Ser Asn Cys Leu Asn Thr Leu Asn Lys Ser Leu Gly Leu Arg Cys Gly
        290                 295                 300
Phe Asn Asn Val Ile Leu Thr Gln Leu Phe Leu Tyr Gly Asp Cys Ile
305                 310                 315                 320
Leu Lys Leu Phe His Asn Glu Gly Phe Tyr Ile Ile Lys Glu Val Glu
                325                 330                 335
Gly Phe Ile Met Ser Leu Ile Leu Asn Ile Thr Glu Glu Asp Gln Phe
                340                 345                 350
Arg Lys Arg Phe Tyr Asn Ser Met Leu Asn Asn Ile Thr Asp Ala Ala
            355                 360                 365
Asn Lys Ala Gln Lys Asn Leu Leu Ser Arg Val Cys His Thr Leu Leu
        370                 375                 380
Asp Lys Thr Val Ser Asp Asn Ile Ile Asn Gly Arg Trp Ile Ile Leu
385                 390                 395                 400
Leu Ser Lys Phe Leu Lys Leu Ile Lys Leu Ala Gly Asp Asn Asn Leu
                405                 410                 415
Asn Asn Leu Ser Glu Leu Tyr Phe Leu Phe Arg Ile Phe Gly His Pro
                420                 425                 430
Met Val Asp Glu Arg Gln Ala Met Asp Ala Val Lys Ile Asn Cys Asn
            435                 440                 445
Glu Thr Lys Phe Tyr Leu Leu Ser Ser Leu Ser Met Leu Arg Gly Ala
        450                 455                 460
Phe Ile Tyr Arg Ile Ile Lys Gly Phe Val Asn Asn Tyr Asn Arg Trp
465                 470                 475                 480
Pro Thr Leu Arg Asn Ala Ile Val Leu Pro Leu Arg Trp Leu Thr Tyr
                485                 490                 495
Tyr Lys Leu Asn Thr Tyr Pro Ser Leu Leu Glu Leu Thr Glu Arg Asp
                500                 505                 510
Leu Ile Val Leu Ser Gly Leu Arg Phe Tyr Arg Glu Phe Arg Leu Pro
            515                 520                 525
```

-continued

```
Lys Lys Val Asp Leu Glu Met Ile Ile Asn Asp Lys Ala Ile Ser Pro
    530                 535                 540
Pro Lys Asn Leu Ile Trp Thr Ser Phe Pro Arg Asn Tyr Met Pro Ser
545                 550                 555                 560
His Ile Gln Asn Tyr Ile Glu His Glu Lys Leu Lys Phe Ser Glu Ser
                565                 570                 575
Asp Lys Ser Arg Arg Val Leu Glu Tyr Tyr Leu Arg Asp Asn Lys Phe
            580                 585                 590
Asn Glu Cys Asp Leu Tyr Asn Cys Val Val Asn Gln Ser Tyr Leu Asn
        595                 600                 605
Asn Pro Asn His Val Val Ser Leu Thr Gly Lys Glu Arg Glu Leu Ser
    610                 615                 620
Val Gly Arg Met Phe Ala Met Gln Pro Gly Met Phe Arg Gln Val Gln
625                 630                 635                 640
Ile Leu Ala Glu Lys Met Ile Ala Glu Asn Ile Leu Gln Phe Phe Pro
                645                 650                 655
Glu Ser Leu Thr Arg Tyr Gly Asp Leu Glu Leu Gln Lys Ile Leu Glu
            660                 665                 670
Leu Lys Ala Gly Ile Ser Asn Lys Ser Asn Arg Tyr Asn Asp Asn Tyr
        675                 680                 685
Asn Asn Tyr Ile Ser Lys Cys Ser Ile Ile Thr Asp Leu Ser Lys Phe
    690                 695                 700
Asn Gln Ala Phe Arg Tyr Glu Thr Ser Cys Ile Cys Ser Asp Val Leu
705                 710                 715                 720
Asp Glu Leu His Gly Val Gln Ser Leu Phe Ser Trp Leu His Leu Thr
                725                 730                 735
Ile Pro His Val Thr Ile Ile Cys Thr Tyr Arg His Ala Pro Pro Tyr
            740                 745                 750
Ile Gly Asp His Ile Val Asp Leu Asn Asn Val Asp Glu Gln Ser Gly
        755                 760                 765
Leu Tyr Arg Tyr His Met Gly Gly Ile Glu Gly Trp Cys Gln Lys Leu
    770                 775                 780
Trp Thr Ile Glu Ala Ile Ser Leu Leu Asp Leu Ile Ser Leu Lys Gly
785                 790                 795                 800
Lys Phe Ser Ile Thr Ala Leu Ile Asn Gly Asp Asn Gln Ser Ile Asp
                805                 810                 815
Ile Ser Lys Pro Ile Arg Leu Met Glu Gly Gln Thr His Ala Gln Ala
            820                 825                 830
Asp Tyr Leu Leu Ala Leu Asn Ser Leu Lys Leu Leu Tyr Lys Glu Tyr
        835                 840                 845
Ala Gly Ile Gly His Lys Leu Lys Gly Thr Glu Thr Tyr Ile Ser Arg
    850                 855                 860
Asp Met Gln Phe Met Ser Lys Thr Ile Gln His Asn Gly Val Tyr Tyr
865                 870                 875                 880
Pro Ala Ser Ile Lys Lys Val Leu Arg Val Gly Pro Trp Ile Asn Thr
                885                 890                 895
Ile Leu Asp Asp Phe Lys Val Ser Leu Glu Ser Ile Gly Ser Leu Thr
            900                 905                 910
Gln Glu Leu Glu Tyr Arg Gly Glu Ser Leu Leu Cys Ser Leu Ile Phe
        915                 920                 925
Arg Asn Val Trp Leu Tyr Asn Gln Ile Ala Leu Gln Leu Lys Asn His
    930                 935                 940
```

-continued

```
Ala Leu Cys Asn Asn Lys Leu Tyr Leu Asp Ile Leu Lys Val Leu Lys
945                 950                 955                 960

His Leu Lys Thr Phe Phe Asn Leu Asp Asn Ile Asp Thr Ala Leu Thr
                965                 970                 975

Leu Tyr Met Asn Leu Pro Met Leu Phe Gly Gly Gly Asp Pro Asn Leu
            980                 985                 990

Leu Tyr Arg Ser Phe Tyr Arg Arg Thr Pro Asp Phe Leu Thr Glu Ala
        995                 1000                1005

Ile Val His Ser Val Phe Ile Leu Ser Tyr Tyr Thr Asn His Asp Leu
    1010                1015                1020

Lys Asp Lys Leu Gln Asp Leu Ser Asp Asp Arg Leu Asn Lys Phe Leu
1025                1030                1035                1040

Thr Cys Ile Ile Thr Phe Asp Lys Asn Pro Asn Ala Glu Phe Val Thr
                1045                1050                1055

Leu Met Arg Asp Pro Gln Ala Leu Gly Ser Glu Arg Gln Ala Lys Ile
            1060                1065                1070

Thr Ser Glu Ile Asn Arg Leu Ala Val Thr Glu Val Leu Ser Thr Ala
        1075                1080                1085

Pro Asn Lys Ile Phe Ser Lys Ser Ala Gln His Tyr Thr Thr Thr Glu
    1090                1095                1100

Ile Asp Leu Asn Asp Ile Met Gln Asn Ile Glu Pro Thr Tyr Pro His
1105                1110                1115                1120

Gly Leu Arg Val Val Tyr Glu Ser Leu Pro Phe Tyr Lys Ala Glu Lys
                1125                1130                1135

Ile Val Asn Leu Ile Ser Gly Thr Lys Ser Ile Thr Asn Ile Leu Glu
            1140                1145                1150

Lys Thr Ser Ala Ile Asp Leu Thr Asp Ile Asp Arg Ala Thr Glu Met
        1155                1160                1165

Met Arg Lys Asn Ile Thr Leu Leu Ile Arg Ile Leu Pro Leu Asp Cys
    1170                1175                1180

Asn Arg Asp Lys Arg Glu Ile Leu Ser Met Glu Asn Leu Ser Ile Thr
1185                1190                1195                1200

Glu Leu Ser Lys Tyr Val Arg Glu Arg Ser Trp Ser Leu Ser Asn Ile
                1205                1210                1215

Val Gly Val Thr Ser Pro Ser Ile Met Tyr Thr Met Asp Ile Lys Tyr
            1220                1225                1230

Thr Thr Ser Thr Ile Ser Ser Gly Ile Ile Glu Lys Tyr Asn Val
        1235                1240                1245

Asn Ser Leu Thr Arg Gly Glu Arg Gly Pro Thr Lys Pro Trp Val Gly
    1250                1255                1260

Ser Ser Thr Gln Glu Lys Lys Thr Met Pro Val Tyr Asn Arg Gln Val
1265                1270                1275                1280

Leu Thr Lys Lys Gln Arg Asp Gln Ile Asp Leu Leu Ala Lys Leu Asp
                1285                1290                1295

Trp Val Tyr Ala Ser Ile Asp Asn Lys Asp Glu Phe Met Glu Glu Leu
            1300                1305                1310

Ser Ile Gly Thr Leu Gly Leu Thr Tyr Glu Lys Ala Lys Lys Leu Phe
        1315                1320                1325

Pro Gln Tyr Leu Ser Val Asn Tyr Leu His Arg Leu Thr Val Ser Ser
    1330                1335                1340

Arg Pro Cys Glu Phe Pro Ala Ser Ile Pro Ala Tyr Arg Thr Thr Asn
1345                1350                1355                1360

Tyr His Phe Asp Thr Ser Pro Ile Asn Arg Ile Leu Thr Glu Lys Tyr
```

-continued

```
                1365                1370                1375
Gly Asp Glu Asp Ile Asp Ile Val Phe Gln Asn Cys Ile Ser Phe Gly
            1380                1385                1390
Leu Ser Leu Met Ser Val Val Glu Gln Phe Thr Asn Val Cys Pro Asn
            1395                1400                1405
Arg Ile Ile Leu Ile Pro Lys Leu Asn Glu Ile His Leu Met Lys Pro
            1410                1415                1420
Pro Ile Phe Thr Gly Asp Val Asp Ile His Lys Leu Lys Gln Val Ile
1425                1430                1435                1440
Gln Lys Gln His Met Phe Leu Pro Asp Lys Ile Ser Leu Thr Gln Tyr
            1445                1450                1455
Val Glu Leu Phe Leu Ser Asn Lys Thr Leu Lys Ser Gly Ser His Val
            1460                1465                1470
Asn Ser Asn Leu Ile Leu Ala His Lys Ile Ser Asp Tyr Phe His Asn
            1475                1480                1485
Thr Tyr Ile Leu Ser Thr Asn Leu Ala Gly His Trp Ile Leu Ile Ile
            1490                1495                1500
Gln Leu Met Lys Asp Ser Lys Gly Ile Phe Glu Lys Asp Trp Gly Glu
1505                1510                1515                1520
Gly Tyr Ile Thr Asp His Met Phe Ile Asn Leu Lys Val Phe Phe Asn
            1525                1530                1535
Ala Tyr Lys Thr Tyr Leu Leu Cys Phe His Lys Gly Tyr Gly Lys Ala
            1540                1545                1550
Lys Leu Glu Cys Asp Met Asn Thr Ser Asp Leu Leu Cys Val Leu Glu
            1555                1560                1565
Leu Ile Asp Ser Ser Tyr Trp Lys Ser Met Ser Lys Val Phe Leu Glu
            1570                1575                1580
Gln Lys Val Ile Lys Tyr Ile Leu Ser Gln Asp Ala Ser Leu His Arg
1585                1590                1595                1600
Val Lys Gly Cys His Ser Phe Lys Leu Trp Phe Leu Lys Arg Leu Asn
            1605                1610                1615
Val Ala Glu Phe Thr Val Cys Pro Trp Val Val Asn Ile Asp Tyr His
            1620                1625                1630
Pro Thr His Met Lys Ala Ile Leu Thr Tyr Ile Asp Leu Val Arg Met
            1635                1640                1645
Gly Leu Ile Asn Ile Asp Arg Ile His Ile Lys Asn Lys His Lys Phe
            1650                1655                1660
Asn Asp Glu Phe Tyr Thr Ser Asn Leu Phe Tyr Ile Asn Tyr Asn Phe
1665                1670                1675                1680
Ser Asp Asn Thr His Leu Leu Thr Lys His Ile Arg Ile Ala Asn Ser
            1685                1690                1695
Glu Leu Glu Asn Asn Tyr Asn Lys Leu Tyr His Pro Thr Pro Glu Thr
            1700                1705                1710
Leu Glu Asn Ile Leu Ala Asn Pro Ile Lys Ser Asn Asp Lys Lys Thr
            1715                1720                1725
Leu Asn Asp Tyr Cys Ile Gly Lys Asn Val Asp Ser Ile Met Leu Pro
            1730                1735                1740
Leu Leu Ser Asn Lys Lys Leu Ile Lys Ser Ser Ala Met Ile Arg Thr
1745                1750                1755                1760
Asn Tyr Ser Lys Gln Asp Leu Tyr Asn Leu Phe Pro Met Val Val Ile
            1765                1770                1775
Asp Arg Ile Ile Asp His Ser Gly Asn Thr Ala Lys Ser Asn Gln Leu
            1780                1785                1790
```

-continued

Tyr Thr Thr Thr Ser His Gln Ile Ser Leu Val His Asn Ser Thr Ser
        1795                1800                1805

Leu Tyr Cys Met Leu Pro Trp His His Ile Asn Arg Phe Asn Phe Val
    1810                1815                1820

Phe Ser Ser Thr Gly Cys Lys Ile Ser Ile Glu Tyr Ile Leu Lys Asp
1825                1830                1835                1840

Leu Lys Ile Lys Asp Pro Asn Cys Ile Ala Phe Ile Gly Glu Gly Ala
            1845                1850                1855

Gly Asn Leu Leu Leu Arg Thr Val Val Glu Leu His Pro Asp Ile Arg
        1860                1865                1870

Tyr Ile Tyr Arg Ser Leu Lys Asp Cys Asn Asp His Ser Leu Pro Ile
    1875                1880                1885

Glu Phe Leu Arg Leu Tyr Asn Gly His Ile Asn Ile Asp Tyr Gly Glu
        1890                1895                1900

Asn Leu Thr Ile Pro Ala Thr Asp Ala Thr Asn Asn Ile His Trp Ser
1905                1910                1915                1920

Tyr Leu His Ile Lys Phe Ala Glu Pro Ile Ser Leu Phe Val Cys Asp
            1925                1930                1935

Ala Glu Leu Ser Val Thr Val Asn Trp Ser Lys Ile Ile Glu Trp
        1940                1945                1950

Ser Lys His Val Arg Lys Cys Lys Tyr Cys Ser Ser Val Asn Lys Cys
    1955                1960                1965

Met Leu Ile Val Lys Tyr His Ala Gln Asp Asp Ile Asp Phe Lys Leu
        1970                1975                1980

Asp Asn Ile Thr Ile Leu Lys Thr Tyr Val Cys Leu Gly Ser Lys Leu
1985                1990                1995                2000

Lys Gly Ser Glu Val Tyr Leu Val Leu Thr Ile Gly Pro Ala Asn Ile
            2005                2010                2015

Phe Pro Val Phe Asn Val Val Gln Asn Ala Lys Leu Ile Leu Ser Arg
        2020                2025                2030

Thr Lys Asn Phe Ile Met Pro Lys Lys Ala Asp Lys Glu Ser Ile Asp
    2035                2040                2045

Ala Asn Ile Lys Ser Leu Ile Pro Phe Leu Cys Tyr Pro Ile Thr Lys
        2050                2055                2060

Lys Gly Ile Asn Thr Ala Leu Ser Lys Leu Lys Ser Val Val Ser Gly
2065                2070                2075                2080

Asp Ile Leu Ser Tyr Ser Ile Ala Gly Arg Asn Glu Val Phe Ser Asn
            2085                2090                2095

Lys Leu Ile Asn His Lys His Met Asn Ile Leu Lys Trp Phe Asn His
        2100                2105                2110

Val Leu Asn Phe Arg Ser Thr Glu Leu Asn Tyr Asn His Leu Tyr Met
    2115                2120                2125

Val Glu Ser Thr Tyr Pro Tyr Leu Ser Glu Leu Leu Asn Ser Leu Thr
        2130                2135                2140

Thr Asn Glu Leu Lys Lys Leu Ile Lys Ile Thr Gly Ser Leu Leu Tyr
2145                2150                2155                2160

Asn Phe His Asn Glu
            2165

<210> SEQ ID NO 31
<211> LENGTH: 21
<212> TYPE: DNA
<213> ORGANISM: Artificial Sequence
<220> FEATURE:

```
<223> OTHER INFORMATION: Oligonucleotide

<400> SEQUENCE: 31
ggtggccggc atggtcccag c                                              21

<210> SEQ ID NO 32
<211> LENGTH: 24
<212> TYPE: DNA
<213> ORGANISM: Artificial Sequence
<220> FEATURE:
<223> OTHER INFORMATION: Oligonucleotide

<400> SEQUENCE: 32
ctcgctggcg ccggctgggc aaca                                           24

<210> SEQ ID NO 33
<211> LENGTH: 24
<212> TYPE: DNA
<213> ORGANISM: Artificial Sequence
<220> FEATURE:
<223> OTHER INFORMATION: Oligonucleotide

<400> SEQUENCE: 33
ttccgagggg accgtcccct cggt                                           24

<210> SEQ ID NO 34
<211> LENGTH: 24
<212> TYPE: DNA
<213> ORGANISM: Artificial Sequence
<220> FEATURE:
<223> OTHER INFORMATION: Oligonucleotide

<400> SEQUENCE: 34
aatggcgaat gggacgtcga cagc                                           24

<210> SEQ ID NO 35
<211> LENGTH: 21
<212> TYPE: DNA
<213> ORGANISM: Artificial Sequence
<220> FEATURE:
<223> OTHER INFORMATION: Oligonucleotide

<400> SEQUENCE: 35
taacaaagcc cgaaggaagc t                                              21

<210> SEQ ID NO 36
<211> LENGTH: 21
<212> TYPE: DNA
<213> ORGANISM: Artificial Sequence
<220> FEATURE:
<223> OTHER INFORMATION: Oligonucleotide

<400> SEQUENCE: 36
gagttgctgc tgccaccgtt g                                              21

<210> SEQ ID NO 37
<211> LENGTH: 23
<212> TYPE: DNA
<213> ORGANISM: Artificial Sequence
<220> FEATURE:
<223> OTHER INFORMATION: Oligonucleotide

<400> SEQUENCE: 37
agcaataact agataacctt ggg                                            23
```

```
<210> SEQ ID NO 38
<211> LENGTH: 24
<212> TYPE: DNA
<213> ORGANISM: Artificial Sequence
<220> FEATURE:
<223> OTHER INFORMATION: Oligonucleotide

<400> SEQUENCE: 38
cctctaaacg ggtcttgagg gtct                                          24

<210> SEQ ID NO 39
<211> LENGTH: 21
<212> TYPE: DNA
<213> ORGANISM: Artificial Sequence
<220> FEATURE:
<223> OTHER INFORMATION: Oligonucleotide

<400> SEQUENCE: 39
ttttgctgaa aggaggaact a                                             21

<210> SEQ ID NO 40
<211> LENGTH: 21
<212> TYPE: DNA
<213> ORGANISM: Artificial Sequence
<220> FEATURE:
<223> OTHER INFORMATION: Oligonucleotide

<400> SEQUENCE: 40
tatgcggccg cgtcgacggt a                                             21

<210> SEQ ID NO 41
<211> LENGTH: 18
<212> TYPE: DNA
<213> ORGANISM: Artificial Sequence
<220> FEATURE:
<223> OTHER INFORMATION: Oligonucleotide

<400> SEQUENCE: 41
ccgggcccgc cttcgaag                                                 18

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
caccacctac cttactcaag t                                             21

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
tttgtttgtg ggtttgatgg ttgg                                          24

<210> SEQ ID NO 44
<211> LENGTH: 35
<212> TYPE: DNA
<213> ORGANISM: Artificial Sequence
<220> FEATURE:
<223> OTHER INFORMATION: Primer
```

```
<400> SEQUENCE: 44
gatatcaaga tctacaataa cattggggca aatgc                              35

<210> SEQ ID NO 45
<211> LENGTH: 31
<212> TYPE: DNA
<213> ORGANISM: Artificial Sequence
<220> FEATURE:
<223> OTHER INFORMATION: Primer

<400> SEQUENCE: 45
gctaagagat ctttttgaat aactaagcat g                                  31

<210> SEQ ID NO 46
<211> LENGTH: 46
<212> TYPE: DNA
<213> ORGANISM: Artificial Sequence
<220> FEATURE:
<223> OTHER INFORMATION: Oligonucleotide

<400> SEQUENCE: 46
tcttgactgt tgtggattgc agggttgact tgactccgat cgatcc                  46

<210> SEQ ID NO 47
<211> LENGTH: 49
<212> TYPE: DNA
<213> ORGANISM: Artificial Sequence
<220> FEATURE:
<223> OTHER INFORMATION: Oligonucleotide

<400> SEQUENCE: 47
cttgtgttgt tgttgtatgg tgtgtttctg attttgtatt gatcgatcc               49

<210> SEQ ID NO 48
<211> LENGTH: 18
<212> TYPE: DNA
<213> ORGANISM: artificial sequence
<220> FEATURE:
<223> OTHER INFORMATION: Primer

<400> SEQUENCE: 48
tgactcgagc tcttggta                                                 18

<210> SEQ ID NO 49
<211> LENGTH: 36
<212> TYPE: DNA
<213> ORGANISM: artificial sequence
<220> FEATURE:
<223> OTHER INFORMATION: Primer

<400> SEQUENCE: 49
atcaggatcc acaataacat tggggcaaat gcaacc                             36

<210> SEQ ID NO 50
<211> LENGTH: 36
<212> TYPE: DNA
<213> ORGANISM: artificial sequence
<220> FEATURE:
<223> OTHER INFORMATION: Primer

<400> SEQUENCE: 50
caactcatag ttacataaaa cggatccgaa tgccat                             36
```